(12) United States Patent
Gradinaru et al.

(10) Patent No.: US 9,778,155 B2
(45) Date of Patent: Oct. 3, 2017

(54) METHODS FOR PHENOTYPING OF INTACT WHOLE TISSUES

(71) Applicant: California Institute of Technology, Pasadena, CA (US)

(72) Inventors: Viviana Gradinaru, La Canada Flintridge, CA (US); Bin Yang, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 14/932,819

(22) Filed: Nov. 4, 2015

(65) Prior Publication Data

US 2016/0123854 A1    May 5, 2016

Related U.S. Application Data

(62) Division of application No. 14/447,607, filed on Jul. 30, 2014.

(60) Provisional application No. 61/880,401, filed on Sep. 20, 2013, provisional application No. 61/992,103, filed on May 12, 2014.

(51) Int. Cl.
*A61L 27/26* (2006.01)
*A61L 27/52* (2006.01)
*G01N 1/30* (2006.01)
*G01N 33/574* (2006.01)

(52) U.S. Cl.
CPC ......... *G01N 1/30* (2013.01); *G01N 33/57492* (2013.01); *G01N 2001/302* (2013.01); *G01N 2001/305* (2013.01)

(58) Field of Classification Search
None
See application file for complete search history.

(56) References Cited

U.S. PATENT DOCUMENTS

| | | | |
|---|---|---|---|
| 6,007,833 A * | 12/1999 | Chudzik | A61K 9/1647 156/275.5 |
| 6,232,092 B1 | 5/2001 | Rogers | |
| 6,465,208 B1 | 10/2002 | Rogers | |
| 6,472,216 B1 | 10/2002 | Chiang | |
| 8,399,207 B2 | 3/2013 | Liaw et al. | |
| 2014/0357526 A1 | 12/2014 | Caprioli et al. | |
| 2015/0087001 A1 | 3/2015 | Gradinaru et al. | |
| 2015/0144490 A1 * | 5/2015 | Deisseroth | G01N 1/30 204/461 |

FOREIGN PATENT DOCUMENTS

| | | |
|---|---|---|
| CN | 103169988 A | 6/2013 |
| EP | 3047271 | 7/2016 |
| JP | 200348928 | 2/2003 |
| JP | 2005535752 | 11/2005 |
| KR | 10-2016-0058900 A | 5/2016 |
| WO | 2012161143 A1 | 11/2012 |
| WO | 2014025392 A1 | 2/2014 |
| WO | 2015041755 A1 | 3/2015 |
| WO | 2016073941 A1 | 5/2016 |
| WO | 2017032149 A1 | 2/2017 |

OTHER PUBLICATIONS

Chung et al. ("Chung", Nature, May 16, 2013, 497, 332-337).*
Ott et al. ("Ott", Nature Medicine, 2008, 14, 213-221).*
PCT/US2015/059600 International Search Report and Written Opinion dated Feb. 19, 2016; 8 pages.
PCT/US2016/047430 International Search Report and Written Opinion dated Nov. 22, 2016; 12 pages.
Genina et al. Optical Clearing of Cranial Bone. Advances in Optical Technologies (2008); 9 pages.
Greenberg et al. Perilipin, a Major Hormonally Regulated Adipocyte-specific Phosphoprotein Associated with the Peripehery of Lipid Storage Droplets. The Journal of Biological Chemistry (1991). 266(17):11341-11346.
Hoffman, A.S. Hydrogels for biomedical applications. Advanced Drug Delivery Reviews (2002). 54:3-12.
Leica HCX PL APO 63X/1.3 Glyc Corr CS (21(degrees)C). Leica technical bulletin for glycerol microscope objectives. (2004) 8 pages.
Lund et al. Lipid composition of normal human bone marrow as determined by column chromatography. Journal of Lipid Research (1962). 3(1):95-98.
O'Brien et al. Lipid composition of the normal human brain: gray matter, white matter, and myelin. Journal of Lipid Research (1965). 6:537-544.
Tainaka et al. Whole-Body Imaging with Single-Cell Resolution by Tissue Decoloization. Cell (2014). 159:911-924.
Tomer et al. Advanced Clarity for rapid and high-resolution imaging of intact tissues. Nature Protocols (2014). 9 (7):1682-1697.
Treweek et al. Whole-body tissue stabilization and selective extractions via tissue-hydrogel hybrids for high-resolution intact circuit mapping and phenotyping. Nature Protocols (2015). 10(11):1860-1896.
Wang et al. Long-term outcome of cryopreserved bone-derived osteoblasts for bone regeneration in vivo. Biomaterials (2011). 32:4546-4555.

(Continued)

*Primary Examiner* — Misook Yu
*Assistant Examiner* — Kauser Akhoon
(74) *Attorney, Agent, or Firm* — Stephen W. Chen; Nixon Peabody LLP

(57) ABSTRACT

In various embodiments, the present application teaches methods and compositions for tissue clearing in which whole organs and bodies are rendered macromolecule-permeable and optically-transparent, thereby exposing their cellular structure with intact connectivity. In some embodiments, the present application teaches PACT, a protocol for passive tissue clearing and immunostaining of intact organs. In other embodiments, the present application teaches RIMS, a refractive index matching media for imaging thick tissue. In yet other embodiments, the application teaches PARS, a method for whole-body clearing and immunolabeling.

22 Claims, 27 Drawing Sheets
(26 of 27 Drawing Sheet(s) Filed in Color)

(56) References Cited

OTHER PUBLICATIONS

Washington et al. Frontal Polymerization Synthesis of Temperature-Sensitive Hydrogels. Journal of American Chemical Society (2001). 123(32):7933-7934.
Yang et al. Single-Cell Phenotyping within Transparent Intact Tissue Through Whole-Body Clearing. Cell (2014). 158 (4):945-958.
EP 14845995.1 Extended Search Report dated May 3, 2017, 9 pages.
Oosthuysen, A et al., Bioprosthetic tissue preservation by filling with a poly(acrylamide) hydrogel. Biomaterials. Dated Mar. 2006; 27(9):2123-30. EPUB Nov. 2, 2005.
Albrecht, Dr et al. Photo—and electropatterning of hydrogel-encapsulated living cell arrays. Lab Chip. Jan. 2005; 5 (1)111-8. EPUB Nov. 24, 2004.
Kiviranta et al. The Rate of Calcium Extraction During EDTA Decalcification from Thin Bone Slices as Assessed with Atomic Absorption Spectrophotometry. Histochemistry (1980) 68, pp. 119-127.

\* cited by examiner

B

A

US 9,778,155 B2

METHODS FOR PHENOTYPING OF INTACT WHOLE TISSUES

CROSS REFERENCE TO RELATED APPLICATIONS

This application is a divisional of U.S. application Ser. No. 14/447,607, filed Jul. 30, 2014, which claims priority under 35 U.S.C. §119(e) from U.S. Provisional Application No. 61/880,401, filed Sep. 20, 2013, and U.S. Provisional Application No. 61/992,103, filed May 12, 2014, the contents of all of which are hereby incorporated herein by reference in their entirety.

FIELD OF THE INVENTION

The present invention generally relates to the field of tissue preparation and characterization.

BACKGROUND

The following description includes information that may be useful in understanding the present invention. It is not an admission that any of the information provided herein is prior art or relevant to the presently claimed invention.

Understanding the structure-function relationships at cellular, circuit, and organ-wide scale requires 3D anatomical and phenotypical maps, currently unavailable for many organs across species. At the root of this knowledge gap is the absence of a method that enables whole-organ imaging. To that end, the technique of tissue clearing holds great potential. There is a need in the art for compositions and methods that can be used to render whole-organs and bodies macromolecule-permeable and optically-transparent, thereby exposing their cellular structure with intact connectivity.

SUMMARY OF THE INVENTION

In various embodiments, the invention teaches a method for modifying the structural and/or optical characteristics of a tissue. In some embodiments, the method includes applying a fixing solution comprising paraformaldehyde (PFA) to the tissue, thereby forming fixed tissue, and applying a hydrogel monomer solution comprising acrylamide and phosphate buffered saline (PBS) to the fixed tissue, thereby forming hydrogel treated tissue. In certain embodiments, the method further includes applying a photoinitiator solution including 2,2'-Azobis[2-(2-imidazolin-2-yl)propane]dihydrochloride to the fixed tissue. In some embodiments, the hydrogel monomer solution includes from 1% to 20% acrylamide. In certain embodiments, the method further includes placing the hydrogel treated tissue into a substantially air tight chamber, and introducing nitrogen into the substantially air tight chamber, thereby forming a de-gassed tissue. In some embodiments, the method further includes incubating the de-gassed tissue at from 15° C. to 60° C., thereby forming incubated tissue. In some embodiments, the method further includes washing the incubated tissue with PBS, thereby forming washed and incubated tissue. In certain embodiments, the method further includes applying a detergent solution that includes sodium dodecyl sulfate (SDS) to the washed and incubated tissue, thereby forming a cleared tissue. In certain embodiments, the detergent solution includes from 1% to 30% SDS in from 0.01 M to 1 M PBS. In some embodiments, the method further includes applying PBS to the cleared tissue, thereby forming cleared and washed tissue. In certain embodiments, the method further includes applying imaging media to the cleared and washed tissue, wherein the imaging media includes: (1) 1-N,3-N-bis(2,3-dihydroxypropyl)-5-[N-(2,3-dihydroxypropyl)acetamido]-2,4,6-triiodobenzene-1,3-dicarboxamide or 5-(N-2,3-Dihydroxypropylacetamido)-2,4,6-triiodo-N,N'-bis(2,3-dihydroxypropyl)isophthalamide, (2) phosphate buffer; (3) tween-20; (4) sodium azide; and optionally (5) sodium hydroxide. In some embodiments, the concentration of 1-N,3-N-bis(2,3-dihydroxypropyl)-5-[N-(2,3-dihydroxypropyl)acetamido]-2,4,6-triiodobenzene-1,3-dicarboxamide or 5-(N-2,3-Dihydroxypropylacetamido)-2,4,6-triiodo-N,N'-bis(2,3-dihydroxypropyl)isophthalamide is from 10 to 100% w/v. In some embodiments, the tissue is obtained from a biopsy. In certain embodiments, the tissue is cancerous or precancerous.

In various embodiments, the invention teaches a method for immunostaining tissue. In some embodiments, the method includes applying a solution that includes a primary antibody to the cleared and washed tissue, thereby forming an antibody-bound tissue. In some embodiments, the method further includes rinsing the antibody-bound tissue with a buffer solution. In certain embodiments, the method further includes applying a solution that includes a secondary antibody to the antibody-bound tissue that has been washed with said buffer solution, wherein the secondary antibody is labeled with a visualizable marker. In certain embodiments, the visualizable marker is fluorescent. In some embodiments, the primary antibody is labeled with a visualizable marker. In some embodiments, that visualizable marker is fluorescent. In certain embodiments, the tissue in the methods described herein is obtained from a biopsy.

In various embodiments, the invention teaches a method for visualizing immunostained tissue. In some embodiments, the method includes utilizing a microscope to visualize immunostained tissue prepared according to the methods described herein. In certain embodiments, the microscope is utilized to implement a form of microscopy selected from the group consisting of confocal microscopy, spinning disk microscopy, epi-fluorescence microscopy, light field microscopy, light-sheet microscopy, multiphoton microscopy.

In various embodiments, the invention teaches a method for modifying the structural and/or optical characteristics of tissue in situ. In some embodiments, the method includes introducing a fixing solution that includes paraformaldehyde (PFA) into the circulatory system of a subject, thereby forming fixed tissue within the subject; and introducing a hydrogel monomer solution that includes acrylamide and phosphate buffered saline (PBS) into the circulatory system of the subject, thereby forming hydrogel-treated tissue within the subject. In certain embodiments, the hydrogel monomer solution includes from 1% to 20% acrylamide. In various embodiments, the method further includes introducing a solution that includes PBS into the circulatory system of the subject, thereby forming PBS-washed tissue. In some embodiments, the method further includes placing the subject into a substantially air tight chamber, and introducing nitrogen into the chamber, thereby forming a de-gassed subject. In some embodiments, the method further includes introducing a photoinitiator solution comprising 2,2'-Azobis[2-(2-imidazolin-2-yl)propane]dihydrochloride into the circulatory system of the degassed subject. In certain embodiments, the method further includes introducing a detergent solution that includes sodium dodecyl sulfate (SDS) into the circulatory system of the subject, thereby forming cleared tissue within the subject. In certain embodiments, the detergent solution includes approximately 1% to 30% SDS in from 0.01M to 1M PBS. In certain embodiments, the method further includes introducing PBS into the circulatory system of the subject, thereby forming cleared and washed tissue within the subject. In certain embodiments, the invention method further includes introducing imaging media into the subject's circulatory system, wherein the imaging media comprises: (1) 1-N,3-N-bis(2,3-dihydroxypropyl)-5-[N-(2,3-dihydroxypropyl)acetamido]-2,4,6-triiodobenzene-1,3-dicarboxamide or 5-(N-2,3-Dihydroxypropylacetamido)-2,4,6-triiodo-N,N'-bis(2,3-dihydroxypropyl)isophthalamide, (2) phosphate buffer; (3) tween-20; (4) sodium azide; and optionally (5) sodium hydroxide. In certain embodiments, the concentration of 1-N,3-N-bis(2,3-dihydroxypropyl)-5-[N-(2,3-dihydroxypropyl)acetamido]-2,4,6-triiodobenzene-1,3-dicarboxamide or 5-(N-2,3 Dihydroxypropylacetamido)-2,4,6-triiodo-N,N'-bis(2,3-dihydroxypropyl) isophthalamide is from 10 to 100% w/v. In some embodiments, the tissue includes brain tissue. In some embodiments, the tissue includes spinal cord tissue. In certain embodiments of the method described above (1) one or more of the solutions is introduced into the subject's circulatory system through a first tube connected to a pump; (2) one or more of the solutions are removed from the subject's circulatory system through a second tube which is in fluid communication with a reservoir into which one or more solutions are collected; and optionally (3) the pump draws the one or more collected solutions from the reservoir and introduces the one or more solutions into the subject's circulatory system through the first tube.

In various embodiments, the invention teaches a method for immunostaining a tissue in situ. In some embodiments, the method includes introducing a solution that includes a primary antibody into the circulatory system of a subject upon whom a method described above has been applied. In some embodiments, the method includes introducing a buffer solution into the circulatory system of the subject. In some embodiments, the method further includes introducing a solution that includes a secondary antibody into the circulatory system of the subject, wherein the secondary antibody is labeled with a visualizable marker. In some embodiments, the visualizable marker is fluorescent. In certain embodiments, the primary antibody is labeled with a visualizable marker. In certain embodiments, that visualizable marker is fluorescent.

In various embodiments, the invention teaches a method for visualizing immunostained tissue, in situ. In some embodiments, the method includes utilizing a microscope to visualize a marker that has been associated with tissue prepared according to an in situ method described above.

In certain embodiments, the invention teaches a composition that includes (1) 1-N,3-N-bis(2,3-dihydroxypropyl)-5-[N-(2,3-dihydroxypropyl)acetamido]-2,4,6-triiodobenzene-1,3-dicarboxamide or 5-(N-2,3-Dihydroxypropylacetamido)-2,4,6-triiodo-N,N'-bis(2,3-dihydroxypropyl)isophthalamide, (2) phosphate buffer; (3) tween-20; (4) sodium azide; and optionally (5) sodium hydroxide. In some embodiments, the concentration of 1-N,3-N-bis(2,3-dihydroxypropyl)-5-[N-(2,3-dihydroxypropyl)acetamido]-2,4,6-triiodobenzene-1,3-dicarboxamide or 5-(N-2,3-Dihydroxypropylacetamido)-2,4,6-triiodo-N,N'-bis(2,3-dihydroxypropyl)isophthalamide is from 10 to 100% w/v.

In certain embodiments, the invention teaches a method for modifying the structural and/or optical characteristics of brain tissue in situ. In some embodiments, the method includes introducing a fixing solution comprising paraformaldehyde (PFA) into the cerebrospinal fluid (CSF) of a subject, thereby forming fixed brain tissue within the subject; and introducing a hydrogel monomer solution comprising acrylamide and phosphate buffered saline (PBS) into the CSF of the subject, thereby forming hydrogel-treated brain tissue within the subject. In certain embodiments, the hydrogel monomer solution includes from 1% to 20% acrylamide. In certain embodiments, the method further includes introducing a solution that includes PBS into the CSF of the subject, thereby forming PBS-washed brain tissue. In some embodiments, the method further includes placing the subject or the head of the subject into a substantially air tight chamber, and introducing nitrogen into the chamber, thereby forming a de-gassed subject. In some embodiments, the method further includes introducing a photoinitiator solution that includes 2,2'-Azobis[2-(2-imidazolin-2-yl)propane]dihydrochloride into the CSF of the degassed subject. In some embodiments, the method further includes introducing a detergent solution that includes sodium dodecyl sulfate (SDS) into the CSF of the subject, thereby forming cleared brain tissue within the subject. In certain embodiments, the detergent solution includes approximately 1% to 30% SDS in from 0.01M to 1M PBS. In certain embodiments, the method further includes introducing PBS into the CSF of the subject, thereby forming cleared and washed brain tissue within the subject. In some embodiments, the method further includes introducing imaging media into the subject's CSF, wherein the imaging media comprises: (1) 1-N,3-N-bis(2,3-dihydroxypropyl)-5-[N-(2,3-dihydroxypropyl)acetamido]-2,4,6-triiodobenzene-1,3-dicarboxamide or 5-(N-2,3-Dihydroxypropylacetamido)-2,4,6-triiodo-N,N'-bis(2,3-dihydroxypropyl)isophthalamide, (2) phosphate buffer; (3) tween-20; (4) sodium azide; and optionally (5) sodium hydroxide. In some embodiments, the concentration of 1-N,3-N-bis(2,3-dihydroxypropyl)-5-[N-(2,3-dihydroxypropyl)acetamido]-2,4,6-triiodobenzene-1,3-dicarboxamide or 5-(N-2,3 Dihydroxypropylacetamido)-2,4,6-triiodo-N,N'-bis(2,3-dihydroxypropyl)isophthalamide is from 10 to 100% w/v. In some embodiments, one or more of the solutions are administered via an intracranial brain shunt. In certain embodiments, one or more of the solutions are administered via an intracranial brain shunt inserted below the dura in the region directly above the olfactory bulb.

In various embodiments, the invention teaches a method for modifying the structural and/or optical characteristics of spinal cord tissue in situ. In some embodiments, the method includes introducing a fixing solution comprising paraformaldehyde (PFA) into the cerebrospinal fluid (CSF) of a subject, thereby forming fixed spinal cord tissue within the subject; and introducing a hydrogel monomer solution comprising acrylamide and phosphate buffered saline (PBS) into the CSF of the subject, thereby forming hydrogel-treated spinal cord tissue within the subject. In certain embodiments, the hydrogel monomer solution includes from 1% to 20% acrylamide. In certain embodiments, the method further includes introducing a solution that includes PBS into the CSF of the subject, thereby forming PBS-washed spinal cord tissue. In certain embodiments, the method further includes placing the subject into a substantially air tight chamber, and introducing nitrogen into the chamber, thereby forming a de-gassed subject. In certain embodiments, the method further includes introducing a photoinitiator solution comprising 2,2'-Azobis[2-(2-imidazolin-2-yl)propane]dihydrochloride into the CSF of the de-gassed subject. In certain embodiments, the method further includes introducing a detergent solution that includes sodium dodecyl sulfate (SDS) into the CSF of the subject, thereby forming cleared spinal cord tissue within the subject. In certain embodiments, the detergent solution includes approximately 1% to 30% SDS in from 0.01M to 1M PBS. In certain embodiments, the method further includes introducing PBS into the CSF of the subject, thereby forming cleared and washed spinal cord tissue within the subject. In certain embodiments, the method further includes introducing imaging media into the subject's CSF, wherein the imaging media includes: (1) 1-N,3-N-bis(2,3-dihydroxypropyl)-5-[N-(2,3-dihydroxypropyl)acetamido]-2,4,6-triiodobenzene-1,3-dicarboxamide or 5-(N-2,3-Dihydroxypropylacetamido)-2,4,6-triiodo-N,N'-bis(2,3-dihydroxypropyl)isophthalamide, (2) phosphate buffer; (3) tween-20; (4) sodium azide; and optionally (5) sodium hydroxide. In certain embodiments, the concentration of 1-N,3-N-bis(2,3-dihydroxypropyl)-5-[N-(2,3-dihydroxypropyl)acetamido]-2,4,6-triiodobenzene-1,3-dicarboxamide or 5-(N-2,3 Dihydroxypropylacetamido)-2,4,6-triiodo-N,N'-bis(2,3-dihydroxypropyl) isophthalamide is from 10 to 100% w/v. In certain embodiments, one or more of the solutions are administered via an intracranial brain shunt. In some embodiments, one or more of the solutions are administered via an intracranial brain shunt inserted directly above the dorsal inferior colliculus.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Exemplary embodiments are illustrated in the referenced figures. It is intended that the embodiments and figures disclosed herein are to be considered illustrative rather than restrictive.

DESCRIPTION OF THE INVENTION

Figure 1:
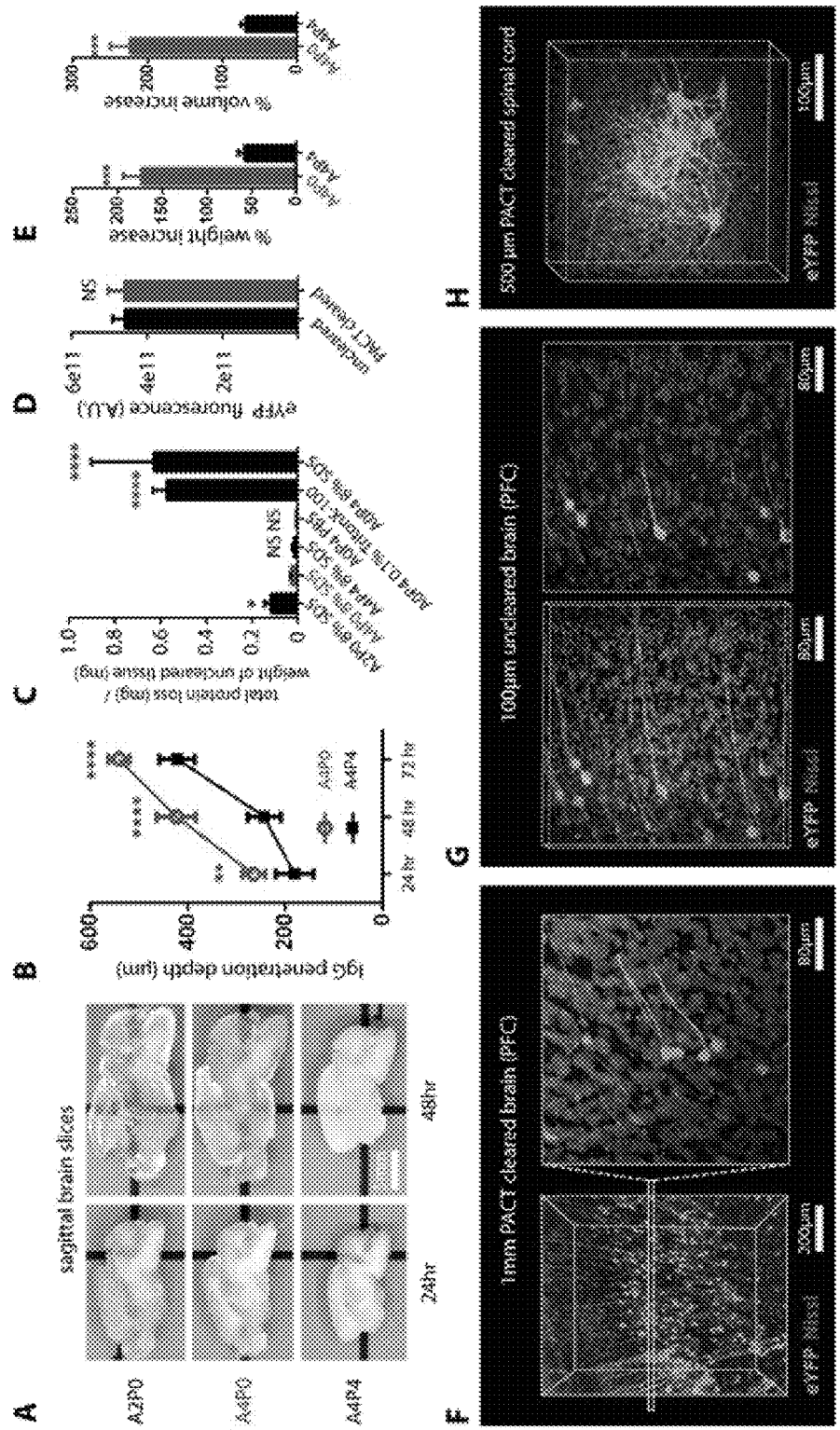
FIG. 1 demonstrates, in accordance with an embodiment of the invention, PACT clearing of A4P0 tissue-hydrogel hybrid achieves optimal transparency and immunohistochemistry compatibility across organs. (A) Optical transparency comparison of 3 mm adult mouse sagittal blocks of A2P0, A4P0, and A4P4 tissue-hydrogel hybrid cleared for 24 h and 48 h. (B) Compared to A4P4, A4P0 tissue-hydrogel hybrid showed faster antibody penetration (n=6 fields of view per sample). (C) The percentage of protein loss from 1 mm mouse brain slices (n=6 slices for each clearing condition); statistical significance is shown for each condition vs. A4P0 8% SDS (red). (D) The integrated eYFP fluorescence intensity in arbitrary units (A.U.) of uncleared and cleared 1 mm Thy1-eYFP mouse brain slices (n=6 slices). (E) Compared to A4P4, the A4P0 hydrogel-tissue hybrid showed higher tissue expansion and weight gain post clearing. (F-H) Thy1-eYFP mouse sections stained with Nissl: (F) 1 mm cleared brain slice, prefrontal cortex (PFC) area (left: z=1 mm imaging stack depth); (G) 1 mm uncleared brain slice, PFC (left: z=100 μm imaging stack depth); (H) 1 mm spinal cord slice (z=500 μm). (I) Substantia nigra pars compacta (SNc) of 1 mm mouse brain slice stained with anti-tyrosine hydroxylase (TH) antibody (z=1 mm). (J) PFC of 1 mm adult mouse brain slices stained with antibodies against GFAP, mouse-IgG, and Iba1 (z=500 μm). (K) 1 mm section of mouse kidney (z=150 μm; arrowheads show glomeruli), heart (z=320 μm), lung (z=550 μm) and intestine (z=350 μm) stained with anti-integrin antibodies, SYTO24, and acridine orange. (L) PACT-cleared human tissue biopsy from basal cell carcinoma (BCC) was stained with anti-pan-cytokeratin (AE1/AE3) Alexa Fluor 488 primary antibody to label endothelial cells and DAPI (700 μm imaging stack depth). All graphs are shown in mean±SEM Statistical significance: for paired samples: 2-tailed Student's t test; for multiple comparisons: one-way ANOVA followed by Bonferroni posthoc (*p<0.05, p<0.01, *p<0.005, and ****p<0.0001). All confocal imaging; for objectives see Methods. Also see FIGS. 7-9 and Tables 1 and 2.
Figure 1:
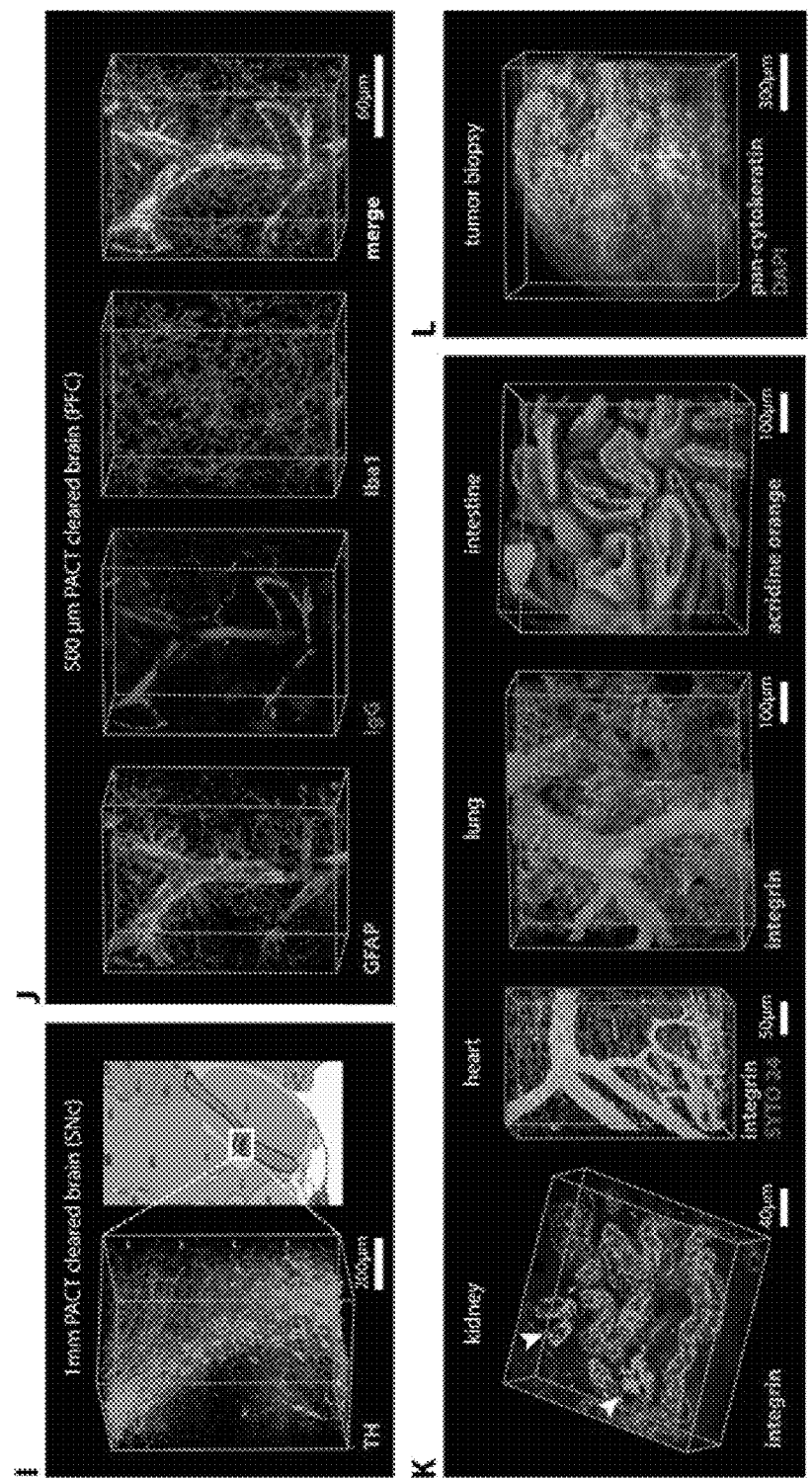

All references cited herein are incorporated by reference in their entirety as though fully set forth. Unless defined otherwise, technical and scientific terms used herein have the same meaning as commonly understood by one of ordinary skill in the art to which this invention belongs. March, *Advanced Organic Chemistry Reactions, Mechanisms and Structure* 5$^{th}$ ed.; and Guyton and Hall, *Textbook of Medical Physiology* 12$^{th}$ ed., provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, certain terms are defined below.

As used herein, PACT is an acronym for PAssive CLARITY Technique.

As used herein, PARS is an acronym for Perfusion-assisted Agent Release in Situ.

As used herein, RIMS is an acronym for Refractive Index Matching Solution.

"Mammal," as used herein, refers to any member of the class Mammalia, including, without limitation, humans and nonhuman primates such as chimpanzees and other apes and monkey species; farm animals such as cattle, sheep, pigs, goats and horses; domesticated mammals, such as dogs and cats; laboratory animals including rodents such as mice, rats and guinea pigs, and the like. The term does not denote a particular age or sex. Thus, adult, newborn subjects, and unborn subjects whether male or female, are intended to be included within the scope of this term.

"Peripheral organs," as used herein, can include but are in no way limited to muscles, heart, lungs, kidneys, colon, gut, intestines, and the like.

By way of additional background, facile and physiologically informative optical access to intact tissues has long been a goal of biologists. As early as the 1800s, work by scientists such as Werner Spalteholz revealed the utility of rendering tissue optically transparent for anatomical and biomedical studies (Spalteholz, 1914). Although the Spalteholz technique and its variants incur damage to tissue integrity and morphology, they are still in use a century later (Steinke and Wolff, 2001), highlighting barriers to the adoption of more recent tissue-clearing methods and modern microscopy techniques. While separate tissue clearing protocols have strengths in an application specific context, none is able to fully surmount the most common challenges: confirmed generalizability across organs other than the brain or embryo, difficulties in execution, and incompatibility with endogenous fluorescence and/or post-hoc immunohistochemistry (Table 1). Thus motivation to improve tissue clearing protocols is sustained around three main objectives: 1) efficient clearing of both central organs and peripheral tissues; 2) preservation of cellular and subcellular structures of multiple organ types; and 3) compatibility with endogenous fluorescent protein expression and post-hoc detection of DNA, RNA, and proteins.

The payoffs of such a method are optical access throughout large volumes of tissues, enabling the study of cell-to-cell spatial relationships and long-range neural connectivity in the context of preserved tissue morphology (Chung and Deisseroth, 2013; Chung et al., 2013; Kim et al., 2013; Zhang et al., 2014). In conjunction with fluorescent tracers, tissue clearing facilitates the identification of interacting cellular structures, including diverging or converging nerves and vasculature at their target sites throughout the body. Fine-scale subcellular analysis of cleared specimens using standard protein and nucleic acid probes can also be achieved in the context of cleared tissues.

In order to advance the above-described technology, in some embodiments the invention teaches methodologies for whole-organism clearing, building upon previous techniques such as CLARITY, SCALE, SeeDB, ClearT, 3DISCO, CUBIC, dibenzyl ether (DBE), and BABB (Murray's Clear) (Becker et al., 2012; Chung et al., 2013; Dodt et al., 2007; Erturk et al., 2012; Hama et al., 2011; Ke et al., 2013b; Kuwajima et al., 2013a; Susaki et al., 2014b). Each of these has made a clear contribution: hydrogel embedding to stabilize tissue structures (Chung et al., 2013), fluorescent protein-compatible clearing reagents (Susaki et al., 2014b), and imaging approaches for large or challenging tissue samples (Becker et al., 2013; Tseng et al., 2009). There are a few especially important points regarding these techniques. First, in the original proof-of-principle for each of these techniques, the detailed methods and optimized protocols were only presented for clearing brain tissue, and occasionally for the spinal cord (Erturk et al., 2012; Zhang et al., 2014) or whole embryo (Dodt et al., 2007; Hama et al., 2011). 3DISCO represents, to date, the most complete elucidation of a clearing method in peripheral tissues. However, as is the case with many prior clearing protocols (Table 1), 3DISCO's clearing reagents (tetrahydrofuran and DBE) substantially quench fluorescent signals in tissue samples (Erturk et al., 2012). CLARITY (Chung et al., 2013) and CUBIC (Susaki et al., 2014b) bypass the fluorescence quenching problem, but CLARITY in its original form used electrophoretic tissue clearing (ETC) to extract lipids from large samples, which can be challenging to implement and can cause variability in final tissue quality, including epitope and fine processes damage and tissue browning due to heating. This led to variations of CLARITY using passive lipid extraction (Zhang et al., 2014, with protocol described in detail in Tomer et al., 2014), along with thermal acceleration of clearing and improved imaging. CUBIC also achieves tissue transparency by passively clearing phospholipids and is compatible with hydrogel embedding. The main weakness of traditional passive clearing methods is their slow speed, which makes them unsuited for clearing large tissue volumes or whole organisms.

As described herein, in some embodiments the inventive methodologies facilitate fast, whole-brain and whole-body clearing using the circulatory system or the cerebrospinal fluid route to directly deliver clarifying agents. In developing these methods, a first step was to improve the hydrogel embedding, clearing, and imaging reagents, which resulted in PACT (PAssive CLARITY Technique) for quicker passive lipid extraction of 1-3 mm thick tissues. To image PACT-cleared tissues, a Refractive Index Matching Solution (RIMS) was developed—a custom economic recipe, with outcome similar to FocusClear™ (Chung et al., 2013; Moy et al., 2013; Tseng et al., 2009). As described in greater detail herein, the PACT reagents can be delivered either intracranially or via the vasculature to achieve whole brain and body clearing and labeling. The latter is termed PARS, for Perfusion-assisted Agent Release in Situ. All steps for PARS, including preservation, clearing, and labeling, are performed in situ prior to tissue extraction. As demonstrated below, PARS, together with RIMS, transform opaque, intact, whole-organisms into optically transparent, fluorescently labeled samples for visualization with conventional confocal microscopy and phenotypic analysis at the cellular, subcellular, and even single-molecule transcripts level.

With the foregoing considerations in mind, additional specific embodiments of the present application are described herein below.

In various embodiments, the invention teaches a method for modifying the structural and/or optical characteristics of a tissue. In some embodiments, the method includes applying a fixing solution that includes paraformaldehyde (PFA) to the tissue, thereby forming fixed tissue, and subsequently applying a hydrogel monomer solution that includes acrylamide and phosphate buffered saline (PBS) to the fixed tissue, thereby forming hydrogel treated tissue. In certain embodiments, the method further includes applying a photoinitiator solution that includes 2,2'-Azobis[2-(2-imidazolin-2-yl)propane]dihydrochloride to the fixed tissue (0.01%-10% (w/v). One of skill in the art would readily appreciate that alternative photoinitiators could also be used. Merely by way of non-limiting example, any compounds of the water-soluble azo initiator chemical class could be used. Effective chemicals that could be used can include, but are in no way limited to, 2,2'-Azobis[2-(2-imidazolin-2-yl)propane]disulfate dehydrate; 2,2'-Azobis(2-methylpropionamidine)dihydrochloride; 2,2'-Azobis[N-(2-carboxyethyl)-2-methylpropionamidine]hydrate; 2,2'-Azobis{2-[1-(2-hydroxyethyl)-2-imidazolin-2-yl]propane}dihydrochloride; 2,2'-Azobis[2-(2-imidazolin-2-yl)propane]; 2,2'-Azobis(1-imino-1-pyrrolidino-2-ethylpropane)dihydrochloride; 2,2'-Azobis{2-methyl-N-[1,1-bis(hydroxymethyl)-2-hydroxyethl]propionamide}; 2,2'-Azobis[2-methyl-N-(2-hydroxyethyl) propionamide]; and the like. In some embodiments, the concentration of photoinitiator solution is from 0.05 to 10% (w/v). In certain embodiments, the hydrogel monomer solution includes from 1% to 20% acrylamide in PBS. In a preferred embodiment, the hydrogel monomer solution includes 4% acrylamide in PBS. In some embodiments, the hydrogel solution includes a protein hydrogel. In some embodiments, the hydrogel used can be a hydrogel as described in Sun et al. PNAS Physical Sciences-Engineering-Biological Sciences-Biochemistry: Synthesis of bioactive protein hydrogels by genetically encoded SpyTag-SpyCatcher chemistry (2014). One of skill in the art would readily appreciate that PBS could be substituted for another buffer with similar characteristics. In some embodiments, the method further includes placing the hydrogel monomer treated tissue into a substantially air tight chamber, and introducing nitrogen into the substantially air tight chamber, thereby forming a de-gassed tissue. In certain embodiments, nitrogen is introduced into the chamber for from 0.1 to 60 minutes. One of skill in the art would readily appreciate that a chamber of a suitable size to accommodate the tissue being processed should be selected for this aspect of the method. Merely by way of example, the chamber described in the Examples section could be used. In alternative embodiments, a chamber with similar characteristics with respect to gas transfer could be used. In certain embodiments, the method further includes incubating the de-gassed tissue at from 15 to 60° C., for a period of from 0.5 to 24 hours, thereby forming incubated tissue. In some embodiments, the method further includes washing the incubated tissue with PBS, thereby forming washed and incubated tissue. In some embodiments, the method further includes applying a detergent solution comprising sodium dodecyl sulfate (SDS) to the washed and incubated tissue, thereby forming cleared tissue. In certain embodiments, the detergent solution includes from 0.5 to 30% SDS (w/v) in from 0.01 to 1 M PBS at a pH of from 6 to 10. In certain embodiments, the tissue is incubated in the detergent solution for from 0.1 to 60 days at from 15 to 60° C. In some embodiments, the tissue is shaken during incubation. In certain embodiments, the method further includes washing the cleared tissue with PBS one or more times over the course of 0.1 to 76 hours, thereby forming cleared and washed tissue. In some embodiments, the method further includes applying imaging media to the cleared and washed tissue. In certain embodiments, the imaging media includes: (1) 1-N,3-N-bis(2,3-dihydroxypropyl)-5-[N-(2,3-dihydroxypropyl)acetamido]-2,4,6-triiodobenzene-1,3-dicarboxamide or 5-(N-2,3-Dihydroxypropylacetamido)-2,4,6-triiodo-N,N'-bis(2,3-dihydroxypropyl)isophthalamide, (2) phosphate buffer; (3) tween-20; (4) sodium azide; and optionally (5) sodium hydroxide. In certain embodiments, the concentration of 1-N,3-N-bis(2,3-dihydroxypropyl)-5-[N-(2,3-dihydroxypropyl)acetamido]-2,4,6-triiodobenzene-1,3-dicarboxamide or 5-(N-2,3-Dihydroxypropylacetamido)-2,4,6-triiodo-N,N'-bis(2,3-dihydroxypropyl)isophthalamide is from 10 to 100% w/v. In certain embodiments, the tissue is obtained from a biopsy. In certain embodiments, the tissue is cancerous or precancerous. In certain embodiments, the tissue is mammalian tissue. In some embodiments, the tissue is human tissue.

In various embodiments, the invention teaches a method for immunostaining tissue prepared according to the above-described methods. In some embodiments, the method includes applying a solution that includes a primary antibody to the cleared and washed tissue of the methods described above, thereby forming an antibody-bound tissue. In certain embodiments, the method further includes rinsing the antibody-bound tissue with a buffer solution. In some embodiments, the buffer solution includes PBS. One of skill in the art would readily appreciate that alternative buffer solutions with comparable characteristics could be substituted for PBS at this step. In some embodiments, the method further includes applying a solution that includes a secondary antibody to the antibody-bound tissue that has been washed with buffer solution, wherein the secondary antibody is labeled with a visualizable marker. In certain embodiments, the visualizable marker is fluorescent. One of skill in the art would recognize that any of a number of visualizable markers suitable for labeling antibodies could be used as a substitute for a fluorescent marker. In various embodiments, the primary antibody is labeled with a visualizable marker. In certain embodiments, the tissue is obtained from a biopsy.

In various embodiments, the invention teaches a method for visualizing immunostained tissue. In certain embodiments, the method includes utilizing a microscope to visualize immunostained tissue prepared according to any of the methods described herein. In certain embodiments, the microscope is utilized to implement a form of microscopy that may include, but is in no way limited to epi-fluorescence microscopy, confocal microscopy, multi-photon microscopy, spinning disk confocal microscopy, light-sheet microscopy, light-field microscopy, Fluorescence Talbot Microscopy (FTM).

The above- and below-described embodiments of immunolabeling with antibodies represent only limited examples of many possible techniques for interrogating tissues and cells that are known in the art. While a number of additional techniques, including utilizing labeled probes of various types, are specifically set forth in the Examples section, they are in no way intended to be limiting. Indeed, any known method for visualizing tissues, cells, or subcellular structures or processes, whether labeled or unlabeled, is intended to be included within the scope of the invention.

In various embodiments, the invention teaches a method for modifying the structural and/or optical characteristics of tissue in situ. In some embodiments, the method includes introducing a fixing solution that includes paraformaldehyde (PFA) into the circulatory system of a subject, thereby forming fixed tissue within the subject; and introducing a hydrogel monomer solution that includes acrylamide and phosphate buffered saline (PBS) into the circulatory system of the subject, thereby forming hydrogel-treated tissue within the subject. In certain embodiments, the fixing and hydrogel monomer solutions used in this aspect of the invention are the same as the fixing and hydrogel monomer solutions described in the section above (and in the Examples section). In some embodiments, the fixing solution is introduced into the circulatory system of the subject for from 0.1 to 48 hours. In certain embodiment, the hydrogel monomer solution is introduced into the subject's circulatory system for a period of from 0.1 to 48 hours. In certain embodiments, the method further includes subsequently introducing a solution that includes PBS into the circulatory system of the subject for a period of from 0.1 to 48 hours, thereby forming PBS-washed tissue in the subject. In certain embodiments, the method further includes placing the subject into a substantially air tight chamber, and introducing nitrogen into the chamber, thereby forming a de-gassed subject. In certain embodiments, the nitrogen is introduced for a period of between 0.5 and 120 minutes. In certain embodiments, the method further includes introducing a photoinitiator solution that includes 2,2'-Azobis[2-(2-imidazolin-2-yl)propane]dihydrochloride into the circulatory system of the de-gassed subject. In some embodiments, the photoinitiator solution has the same characteristics as the photoinitiator solution used for preparing tissue as described in the section above and in the Examples section. In some embodiments, the method further includes introducing a detergent solution comprising sodium dodecyl sulfate (SDS) into the circulatory system of the subject, thereby forming cleared tissue within the subject. In certain embodiments, the detergent solution includes approximately 0.5 to 30% SDS in from 0.01 to 1 M PBS. In some embodiments, the detergent solution is introduced into the subject's circulatory system for from 0.5 to 30 days from 20 to 60° C. In some embodiments, the method further includes introducing PBS into the circulatory system of the subject, thereby forming cleared and washed tissue within the subject. In some embodiments, the PBS is introduced for from 0.5 to 30 days. In certain embodiments, the method further includes introducing imaging media into the subject's circulatory system. In certain embodiments, the imaging media includes (1) 1-N,3-N-bis(2,3-dihydroxypropyl)-5-[N-(2,3-dihydroxypropyl)acetamido]-2,4,6-triiodobenzene-1,3-dicarboxamide or 5-(N-2,3-Dihydroxypropylacetamido)-2,4,6-triiodo-N,N'-bis(2,3-dihydroxypropyl)isophthalamide, (2) phosphate buffer; (3) tween-20; (4) sodium azide; and optionally (5) sodium hydroxide. In some embodiments, the concentration of 1-N,3-N-bis(2,3-dihydroxypropyl)-5-[N-(2,3-dihydroxypropyl)acetamido]-2,4,6-triiodobenzene-1,3-dicarboxamide or 5-(N-2,3 Dihydroxypropylacetamido)-2,4,6-triiodo-N,N'-bis(2,3-dihydroxypropyl)isophthalamide is from 10 to 100% w/v. In some embodiments, the imaging media is introduced for a period of from 0.1 to 14 days. In certain embodiments, the tissue includes brain tissue. In certain embodiments, the tissue includes spinal cord tissue. In some embodiments, the tissue is mammalian tissue. In some embodiments, the tissue is human tissue.

In various embodiments of the methods described herein (1) one or more of the solutions described herein is introduced into the subject's circulatory system through a first tube connected to a pump; (2) one or more of the solutions are removed from the subject's circulatory system through a second tube which is in fluid communication with a reservoir into which one or more solutions are collected; and optionally (3) the pump draws the one or more collected solutions from the reservoir and introduces the one or more solutions into the subject's circulatory system through the first tube.

In various embodiments, the invention teaches a method for immunostaining a tissue in situ. In some embodiments, the method includes introducing a solution that includes a primary antibody into the circulatory system of a subject that has been treated according to any of the methods described above. In some embodiments, immunostaining is performed prior to utilizing imaging media. In some embodiments, the solution that includes a primary antibody is introduced for a period of from 0.5 to 14 days. In some embodiments, the method further includes introducing a buffer solution into the circulatory system of the subject. In some embodiments, the buffer solution is PBS. In some embodiments, the buffer solution is introduced for a period of between 0.5 and 14 days. In certain embodiments, the method further includes introducing a solution that includes a secondary antibody into the circulatory system of the subject, wherein the secondary antibody is labeled with a visualizable marker. In some embodiments, the solution that includes a secondary antibody is introduced for a period of between 0.5 and 14 days. In certain embodiments, the visualizable marker is fluorescent. In some embodiments, the primary antibody is labeled with a visualizable marker. In some embodiments, the tissue is mammalian tissue.

In some embodiments, the invention teaches a composition that includes (1) 1-N,3-N-bis(2,3-dihydroxypropyl)-5-[N-(2,3-dihydroxypropyl)acetamido]-2,4,6-triiodobenzene-1,3-dicarboxamide or 5-(N-2,3-Dihydroxypropylacetamido)-2,4,6-triiodo-N,N'-bis(2,3-dihydroxypropyl)isophthalamide, (2) phosphate buffer; (3) tween-20; (4) sodium azide; and optionally (5) sodium hydroxide. In certain embodiments, the concentration of 1-N,3-N-bis(2,3-dihydroxypropyl)-5-[N-(2,3-dihydroxypropyl)acetamido]-2,4,6-triiodobenzene-1,3-dicarboxamide or 5-(N-2,3-Dihydroxypropylacetamido)-2,4,6-triiodo-N,N'-bis(2,3-dihydroxypropyl)isophthalamide is from 10 to 100% w/v.

PARS, PACT, and related methods described herein could be used on any animal, and are in no way limited to those examples specifically set forth herein. Further, the methods described herein can be used for whole organisms ranging from embryos to adults.

One skilled in the art will recognize many methods and materials similar or equivalent to those described herein, which could be used in the practice of the present invention. Indeed, the present invention is in no way limited to the methods and materials described herein. Additional non-limiting embodiments of the invention are included in the examples below.

EXAMPLES

Example 1

Results

Method for Passive Clearing and Immunostaining of Whole Organs

Figure 7:
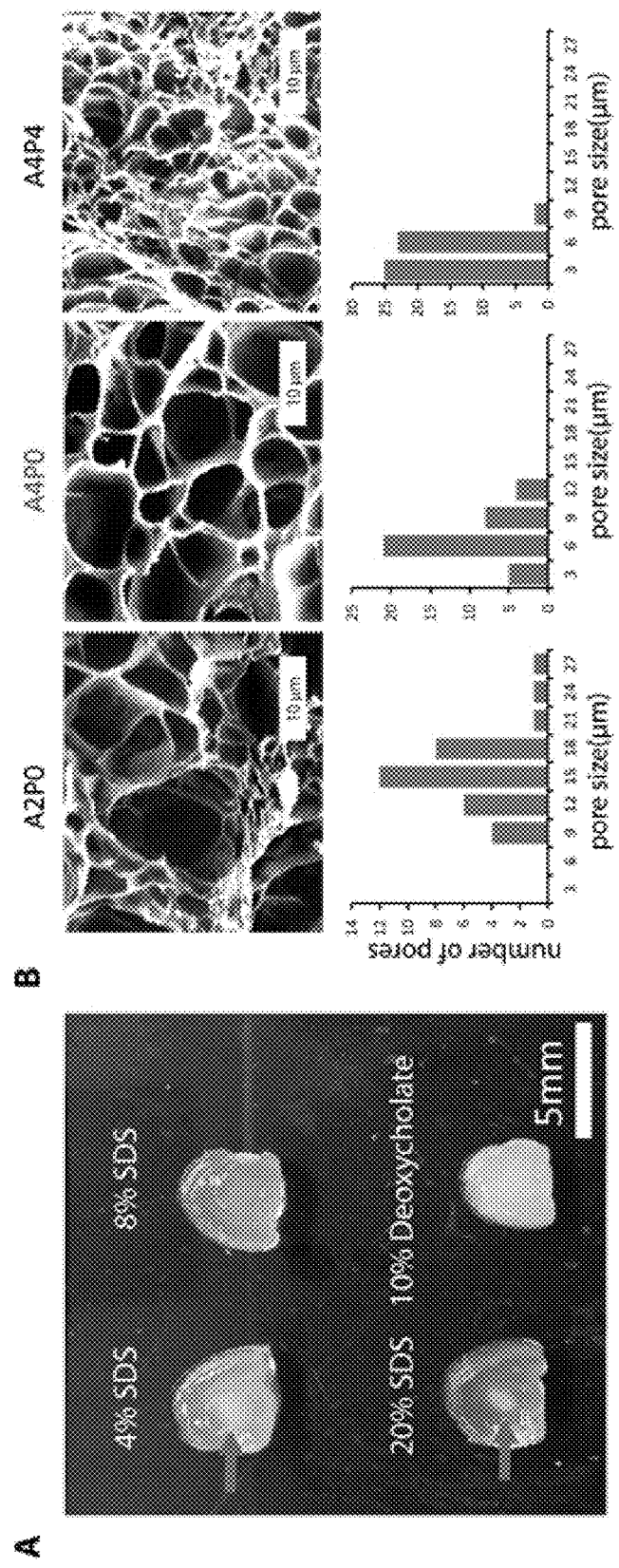
FIG. 7 demonstrates, in accordance with an embodiment of the invention (related to FIGS. 1, 3 and 4; and Table 2), PACT cleared A4P0 tissue-hydrogel hybrid using 8% SDS shows excellent optical transparency. All samples were PACT cleared for 3 days. (A) Comparison of optical transparency of 3 mm mouse brain coronal blocks PACT cleared using different percentage of SDS and 10% sodium deoxycholate (arrows indicate incomplete clearing). (B) Scanning Electron Microscopy (SEM) images showing the pores of tissue hybridized with different hydrogel percentages; the histograms below indicate the distribution of the pore size for each condition. (C) Compared to A4P4, A4P0 tissue-hydrogel hybrids show greater tissue expansion and optical transparency (1 mm mouse brain slices). Samples for (B) and (C) were PACT cleared in 8% SDS. Images for (A) and (C) were taken using bright field camera.
Figure 7:
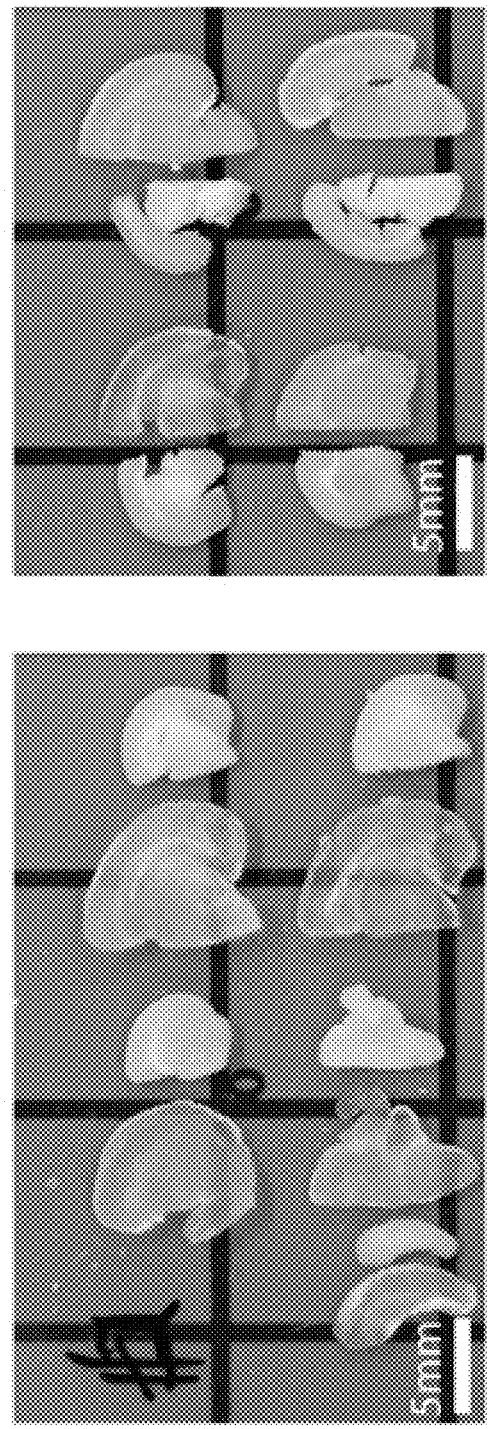

In some embodiments, thick tissue is rendered optically transparent for imaging in three main steps. First, tissue is cross-linked and hybridized to hydrogel monomers to stabilize biomacromolecules. Second, tissue lipids are extracted from the tissue-hydrogel matrix with ionic detergent(s). Third, cleared tissue is embedded in RIMS for imaging, or for long-term storage. Although wholebody clearing was the primary goal, it was recognized that the processing of small or particularly fragile specimens and organs would best be accomplished by a mild, passive clearing protocol. PACT was developed for rendering rodent whole organs, their 1-3 mm thick sections, including brain, spinal cord, kidney, heart, lung, and intestine, or human tissue biopsies transparent. The clearing speed depends in part on the rate of lipid solvation by detergent micelles, and the rate of diffusion of detergent micelles in tissue (Hoffman, 2002). However, unless an applied force accelerates their diffusion through tissue, such as the electric field in CLARITY's ETC (Chung et al., 2013; Tomer et al., 2014), lipid extraction by large micelles is relatively slow. Different detergents were tested at various concentrations for their ability to passively clear 3 mm coronal mouse brain blocks over 3-day incubation. Sodium dodecyl sulfate (SDS) at all concentrations was superior for lipid solvation and removal from brain tissue relative to other detergents, and moreover, only the 8% SDS concentration achieved uniform clearing throughout the entire 3 mm block (FIG. 7A).

It was hypothesized that a decrease in the cross-link density of the tissue-hydrogel would facilitate both lipid extraction and macromolecule penetration into thick, highly myelinated or fibrous tissue during subsequent immunohistochemistry. To test this, 3 mm brain sections were infused with varying combinations and concentrations of formaldehyde, acrylamide, and bis-acrylamide, degassed, and polymerized at 37° C. The efficiency of tissue clearing (FIG. 1A) and the depth of antibody penetration (FIG. 1B) increased significantly when lower concentrations of formaldehyde and acrylamide were used, and when bis-acrylamide, an acrylamide cross-linking agent used in CLARITY (Tomer et al., 2014), was excluded from the cocktail of hydrogel monomers. Upon observing a qualitative increase in tissue transparency in the tissue-hydrogels prepared with lower acrylamide concentrations (FIG. 1A), the different PACT tissue preparations were assayed for protein loss, tissue integrity, and changes in weight and volume during clearing to ensure that a minimal crosslinking scheme was sufficient to preserve tissue morphology and molecular information. The amount of protein that leached out of tissue into SDS clearing buffer was statistically indistinguishable between 4% PFA-fixed, uncleared tissue samples (A0P4) that were incubated in PBS as a control, and those cleared tissue-hydrogel matrices prepared with 4% acrylamide (A4P0) or with 4% acrylamide plus 4% PFA (A4P4) (FIG. 1C). Notably, the amount of protein recorded in the 8% SDS clearing bath solutions for all hydrogel embedded samples was less than the protein loss ($0.57\pm0.11$ mg per mg gross weight) for the samples preserved only with 4% PFA and incubated in PBS-0.1% TritonX-100, a mild detergent-containing buffer. This implies that hydrogel monomers effectively crosslink and stabilize tissue protein, which is further supported by the finding that unpolymerized, PFA-fixed tissue incubated in 8% SDS showed poor protein retention ($0.63\pm0.02$ mg protein loss per mg gross weight) (FIG. 1C).

To corroborate these results on the preservation of molecular content in PACT tissue, the relative levels of native eYFP fluorescence were visualized and quantified in PACT brain samples from Thy1-eYFP transgenic mice. While a decrease in mean fluorescence intensity was observed under both hydrogel formulations (A4P0, A2P0), PACT samples showed comparable total intensity relative to uncleared tissue (FIG. 1D) once the fluorescent measurements were normalized for tissue expansion (FIG. 7C). Indeed, tissue-hydrogel matrices that were prepared using acrylamide alone (A4P0) exhibited tissue weight and volume changes of ~174% and ~223%, respectively (FIG. 1E) over A4P4 counterparts. But, upon the transfer of tissue samples from clearing solution to mounting media, PACT samples shrank back to their original size within a few hours (FIG. 9D). This tissue expansion-contraction has been documented in previous brain clearing protocols (Chung et al., 2013; Hama et al., 2011; Susaki et al., 2014b), wherein it was concluded that these size changes, though suboptimal, did not appear to negatively influence gross tissue morphology or cellular architecture. To visualize the effect of PFA on cross-link density in the tissue-hydrogel matrix, which is hypothesized to limit tissue expansion, PACT-cleared brain slices were imaged via scanning electron microscopy (SEM) (FIG. 7B). It was noted that A2P0 matrices had the largest pore sizes, followed by A4P0, while A4P4 had the smallest visualized pore sizes; pore size directly affects diffusion rate with faster macromolecular diffusion times in tissue-hydrogel matrices with larger pores. Tissue deformity (i.e. expansion and contraction) during PACT processing and mounting did not appear to affect the overall cellular organization or protein content of samples relative to conventional histological processing (FIGS. 1F-1L). Thus, A4P0 was selected for PACT given its balance between clearing speed, protein retention, and intermediate pore size tissue, which is conducive to macromolecule tissue penetration during histology.

PACT Reagents are Compatible with Histology and Endogenous Fluorochromes

To ensure that the signal intensity from genetically encoded fluorescent proteins was preserved throughout PACT processing, 1 mm-thick Thy1-eYFP tissue sections were A4P0-hybridized, PACT-cleared, and imaged using confocal microscopy. Despite PACT clearing, and importantly, the slow image acquisition time for thick samples the genetically expressed eYFP was readily detected throughout the samples (FIGS. 1F, 1H). Furthermore, the tissue-hydrogel matrix still permitted uniform Nissl staining of thick, cleared sections (FIG. 1F, compared to uncleared 80 µm sections in FIG. 1G). The overall tissue architecture remained constant between cleared and uncleared sections, as revealed by Nissl staining (red), which assuages concern that successive swelling and then shrinking of tissue caused permanent tissue deformity.

Not only were native proteins including those maintaining the structural integrity of tissue samples, retained by the tissue-hydrogel matrix during clearing (FIGS. 1C, 1F, 1H), but also the cleared tissue blocks were sufficiently macromolecule-permeable to permit labeling of peptidic and nucleic acid epitopes using a variety of common histological markers (e.g. antibodies, small-molecules, mRNA probes). For example, aside from Nissl, 1 mm PACT sections from the mouse brain and spinal cord were immunolabeled with antibodies against antityrosine hydroxylase (TH) (FIG. 1I); glial fibrillary acidic protein (GFAP), murine immunoglobulin G (IgG), and ionized calcium binding adaptor molecule 1 (Iba1) (FIG. 1J). These targeted moieties represent antigens occupying a wide variety of cellular locations: membrane-localized and cytosolic, neuronal and nonneuronal antigens. PACT clearing decreased light scattering in tissue samples such that all labels were easily resolved across the entire 1 mm section during single-photon fluorescence imaging.

Figure 8:
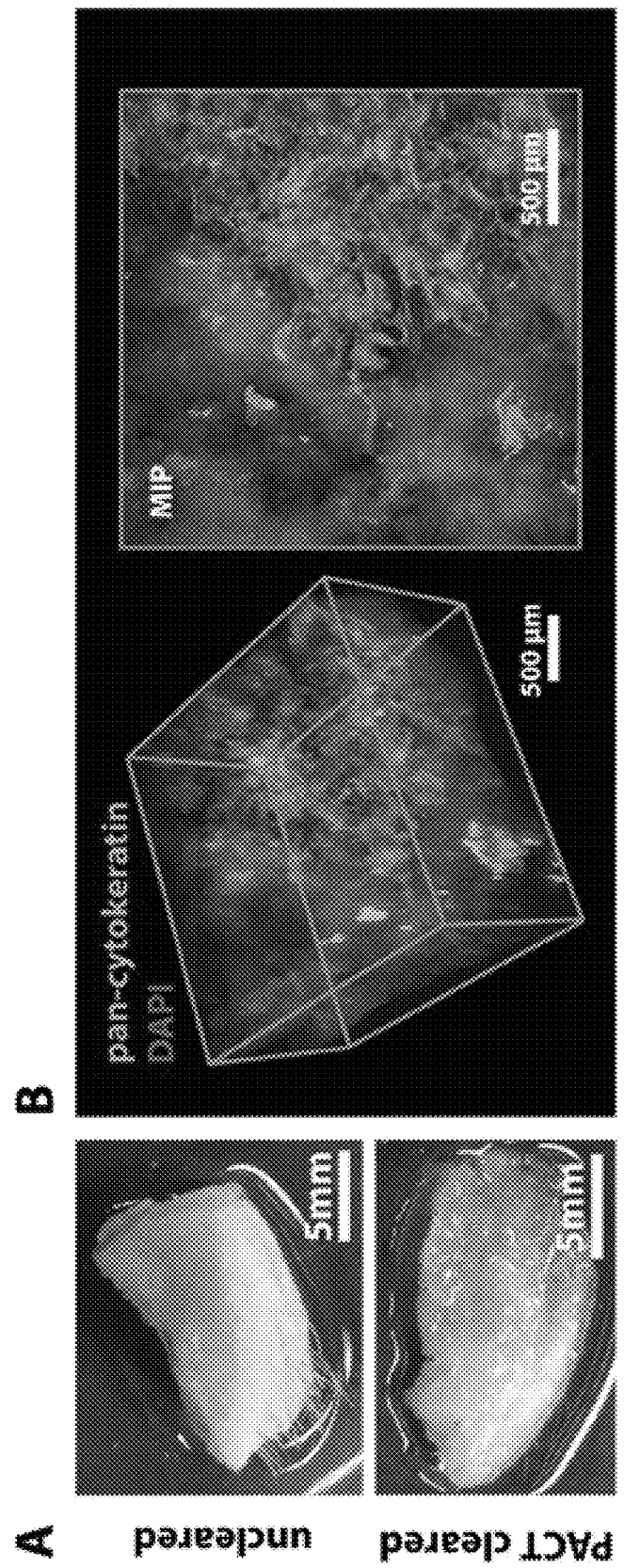
FIG. 8 demonstrates, in accordance with an embodiment of the invention (related to FIGS. 1 and 2), PACT samples are compatible with gross tissue pathology and fine transcriptional analysis. (A-C) A 3 mm-thick section of a human basal cell carcinoma (BCC) tissue biopsy was cleared with PACT, immunolabeled with anti-pan-cytokeratin (AE1/AE3) antibody, and counter-stained with DAPI. (A) Photographs of uncleared (top) and cleared 3 mm-thick section (bottom) of human basal cell carcinoma (BCC) tissue biopsy (scale bars=5 mm). (B) Low magnification (5×) and (C) high magnification (25×) 3D rendering and maximum intensity projections showing locations of AE1/AE3 positive cells and keratin filament remnants (green) of apoptotic tissue with respect to all cells (magenta) of the region. (scale bars=500 μm and 100 μm). (D) Background differences between pre-processed (except background subtraction on DAPI channel) (left and middle panels) and post-processed (right panels) images of PACT cleared (upper panels) and uncleared (lower panels) smFISH brain slices. Left panels: 30 μm maximum intensity projection (MIP). Middle panels: single 0.5 μm image at a depth of 3 μm. Right panels: Laplacian of Gaussian (LoG) filtered, contrast adjusted image from middle panel. All images were processed with identical contrast threshold and LoG filtering parameters. For microscopy see Methods.
Figure 8:
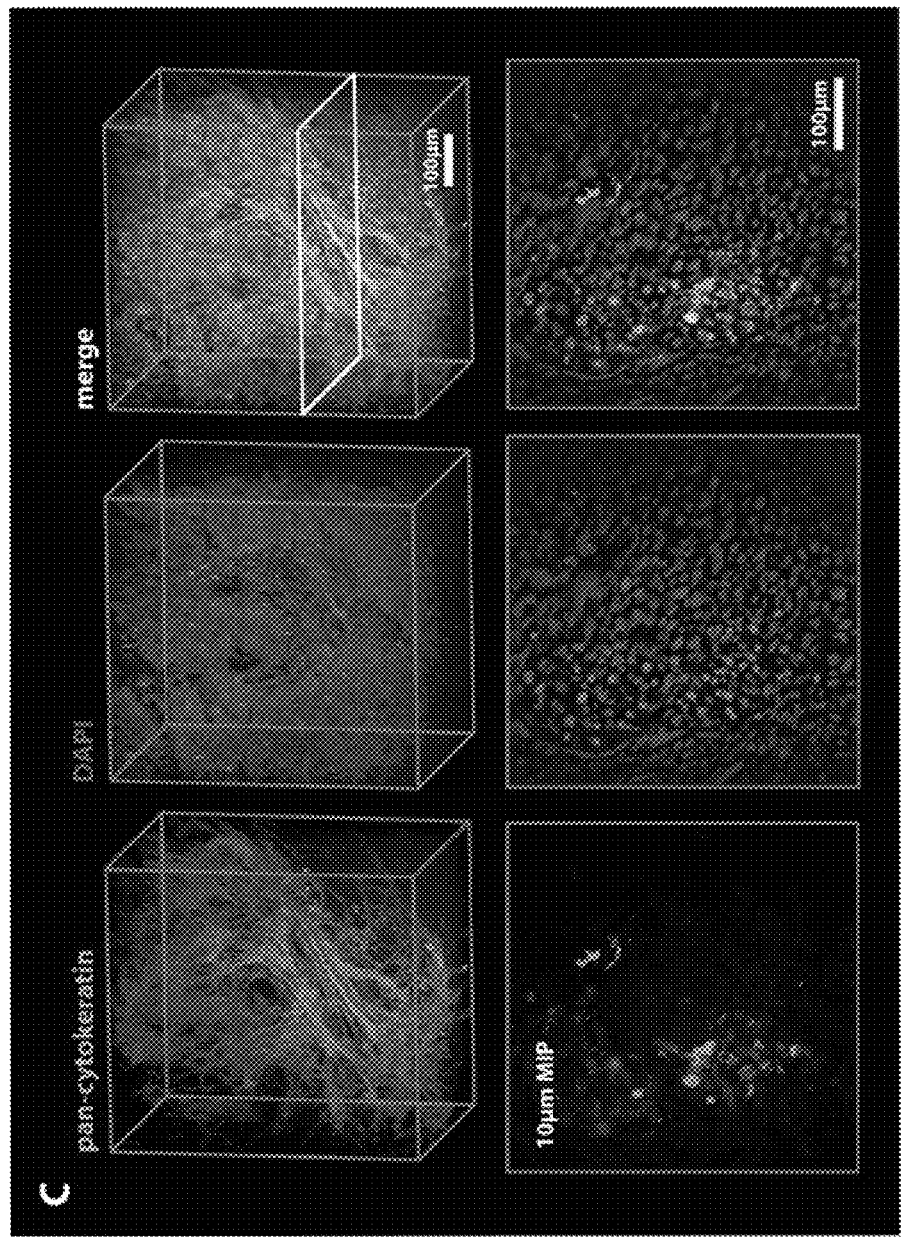
Figure 8:
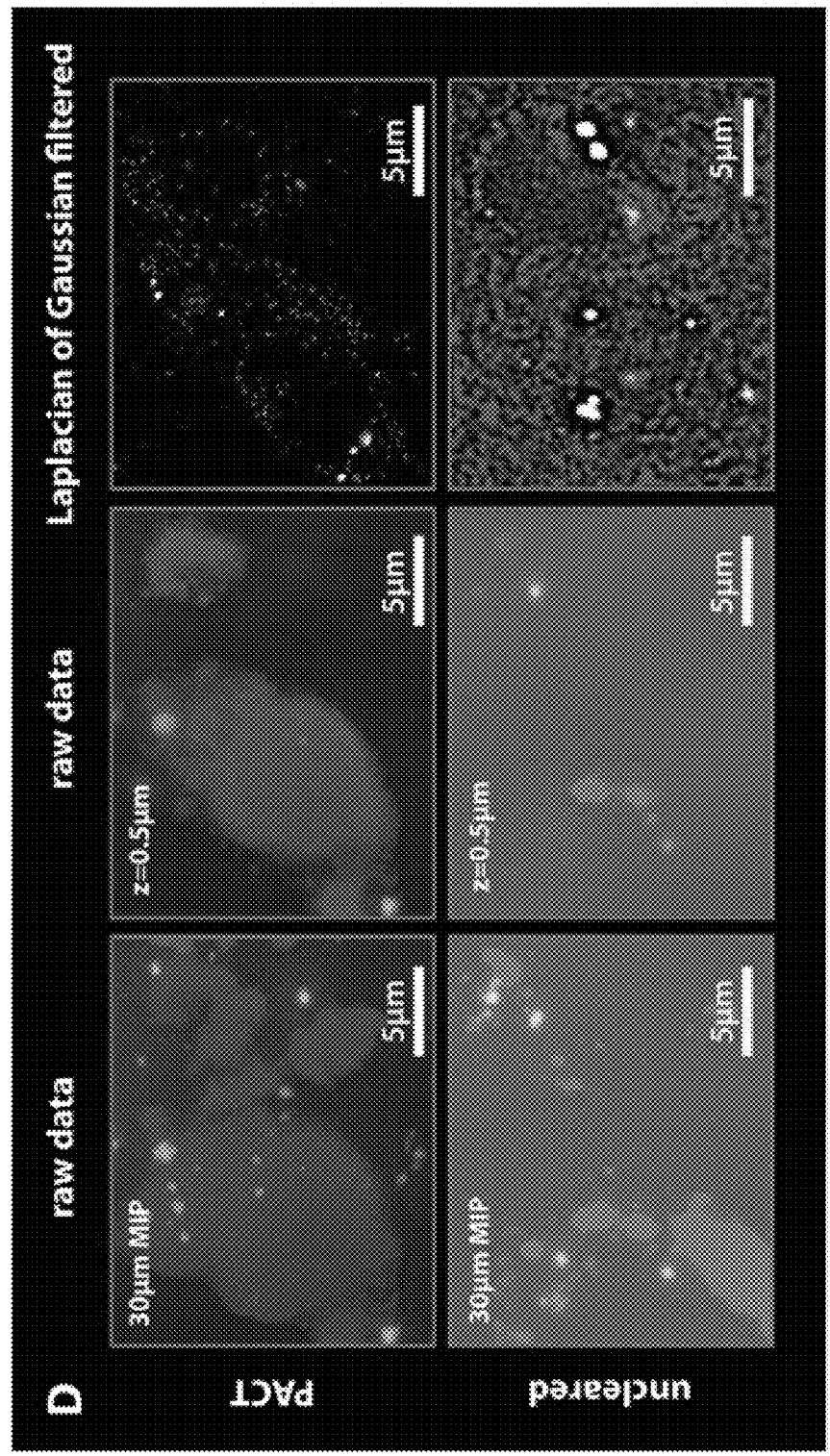

To confirm that PACT methodologies were effective on peripheral tissues as well, the kidney, heart, lung, and intestine of Thy1-eYFP mice were excised, cleared, and labeled with anti-integrin antibodies, acridine orange (AO), and/or SYTO24 (FIG. 1K). As observed in the central organ samples (FIGS. 1F, 1H-J), small molecule dyes and antibodies alike rapidly diffused through 1-3 mm thick A4P0-crosslinked and PACT-cleared sections of peripheral organs. While the time for complete immunolabeling of thick sections depends on several factors, including the tissue type, hydrogel pore size (FIG. 7B), and the extent of lipid removal (FIGS. 1A, 7A), uniform antibody penetration was achieved throughout PACT samples with a 7-12 day incubation. However, for studies that only require labeling with small molecule fluorescent dyes one may obtain rapid staining of 1-3 mm PACT brain sections with a single overnight to 3-day incubation, respectively. Some peripheral tissues were stained even faster, wherein AO labeling of individual nuclei in unsectioned mouse intestinal tissue (~400 um thick) was attained in under one hour (FIG. 1K). The next issue was to determine if PACT can be applied to pathological samples. Human skin cancer biopsies (FIG. 8A) were cleared and stained with pan-cytokeratin to visualize tumor cells (FIG. 1L, FIGS. 8 B-C). In sum, the entire PACT-cleared tissue block was accessible down to the subcellular level to molecular interrogation using standard immunohistochemical methods and conventional fluorescence microscopy.

Figure 2:
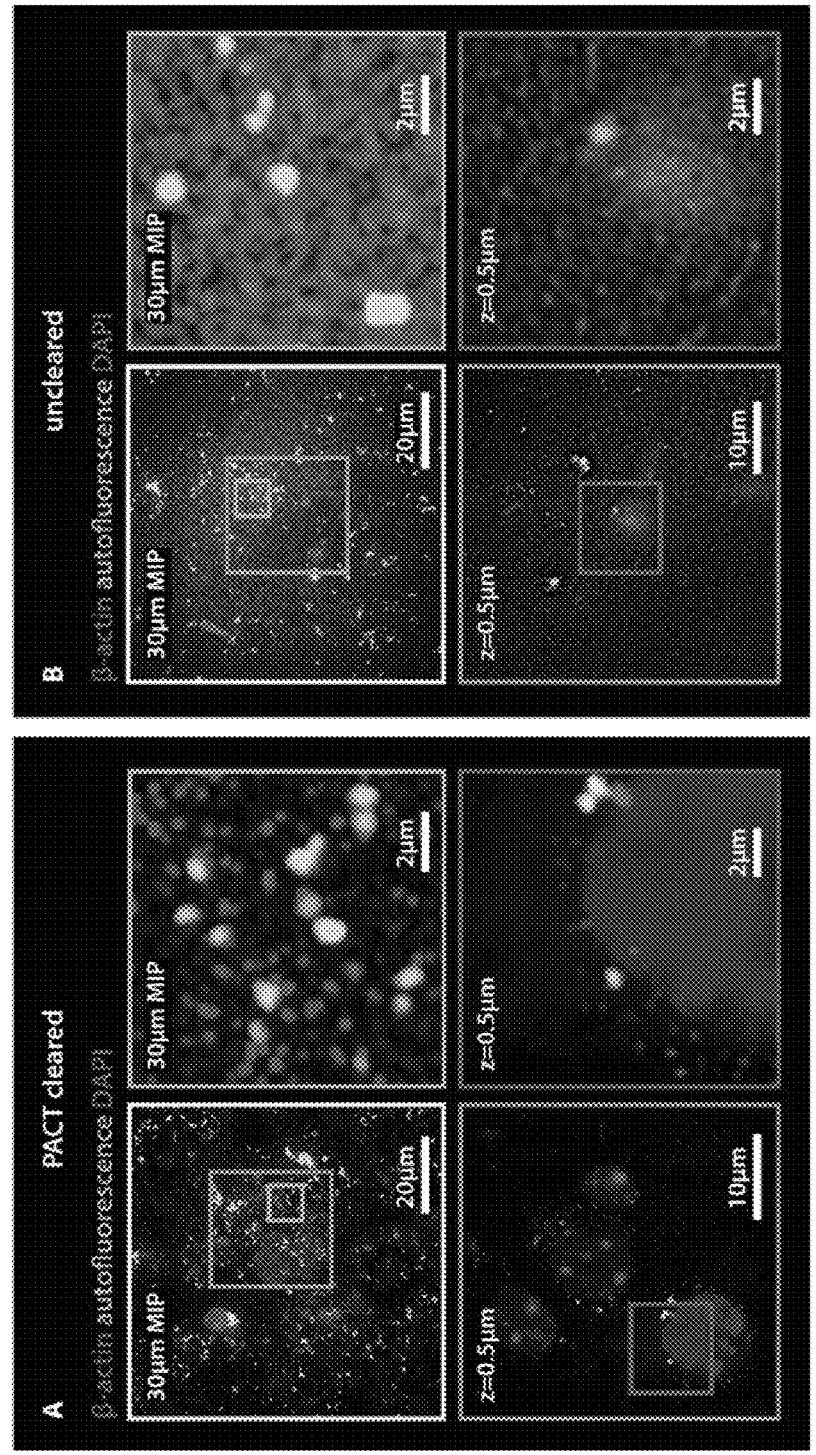
FIG. 2 demonstrates, in accordance with an embodiment of the invention, detection of individual mRNA transcripts in PACT tissue sections by smFISH. 100 μm-thick mouse brain slices were hybridized with twenty-four 20mer oligonucleotide probes towards β-actin mRNA labeled with Alexafluor 594. (A) PACT-cleared smFISH brain slices. Upper panel shows 30 μm maximum intensity projection. An abundant number of diffraction limited spots corresponding to single beta-actin mRNAs (red) were readily detected up to 30 μm in depth under 589 nm illumination. Note bright amorphous granules (yellow) are background lipofuscin vesicles that show up in both 589 nm (red) and 532 nm autofluorescence (green) channels, whereas smFISH signals are in the red channel only. (B) Compared to PACT cleared slices, smFISH in uncleared brain slices showed significantly decreased contrast. (Lower panels in A and B show single slices of 0.5 um at 12 um depth; the images were processed from raw data using the same contrast scale and Laplacian of Gaussian filtering; for raw data see FIG. 8D) (C) Signal to noise ratio as a function of depth shows PACT-clearing tissue increases the signal to noise ratio of smFISH throughout the thickness of the sample as compared to uncleared tissue. (D) smFISH intensities show no appreciable differences between 19 uncleared and PACT-cleared tissue. p=0.8722; 2-tailed Student's t test. (E) Comparison of background intensity between uncleared and PACT-cleared tissue illustrates the significant reduction of background fluorescence in PACT-cleared tissue. p=0.0006; 2-tailed Student's t test. All graphs are shown in mean±SEM. For microscopy see Methods.
Figure 2:
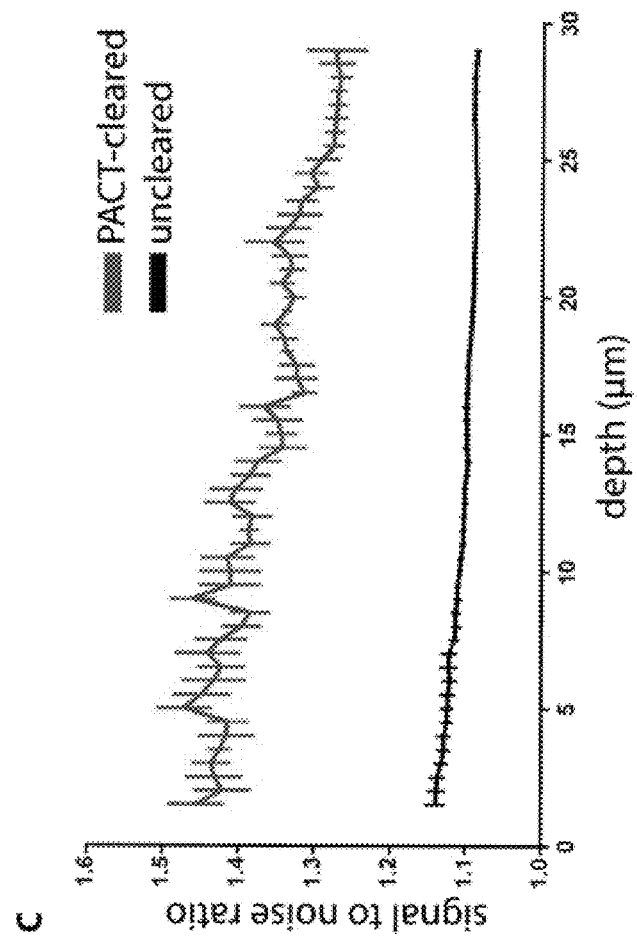

To determine if PACT is compatible with established procedures to visualize single mRNA transcripts, PACT-processed tissue was subjected to single-molecule fluorescent in situ hybridization, smFISH (Femino et al., 1998; Raj et al., 2008). The methodology of smFISH is capable of detecting single RNA molecules with high specificity in fixed cells and its high sensitivity allows for measurements of RNA abundance and subcellular localization. However, smFISH in tissue sections remains challenging due to low signal to noise ratio caused by tissue autofluorescence. Herein, β-actin transcripts in 100 μm-thick cleared mouse brain sections were labeled using 24 Alexa 594-labelled 20mer oligonucleotide probes towards β-actin mRNA. Tissue samples were slide-mounted in media containing 4',6-diamidino-2-phenylindole (DAPI) and imaged via single-photon microscopy. β-actin transcripts were indeed retained in the cytoplasm of neurons throughout PACT and smFISH processing, and single points of fluorescence could be distinguished despite the high copy number of β-actin in cells and the considerable thickness of imaged brain section (Buxbaum et al., 2014; Raj et al., 2008) (FIG. 2A). PACT tissue exhibited significantly increased contrast of diffraction-limited spots throughout the tissue relative to uncleared tissue (FIG. 2C). It was determined that smFISH intensity showed very little difference between PACT cleared and uncleared tissue, while background intensity was significantly reduced (FIGS. 2 A-B, 2D and 2E, 8D). These findings, taken together with the increase in smFISH signal to noise ratio seen in PACT cleared tissues, suggests that background autofluorescence in thick samples is the main factor obscuring smFISH signal in uncleared tissue.

Recipe for Refractive Index Matching Solution for Imaging and Long-Term Storage of Cleared Tissue Effective imaging relies on sample immersion in a mounting media that reduces the refractive index (RI) variations within heterogeneous tissue and that alleviates the RI mismatch between tissue, mounting media and lens immersion media interfaces. In response to the prohibitive cost and limited availability of traditional products, a less expensive substitute was formulated: RIMS, for Refractive Index Matching Solution, with an RI appropriate for tissue imaging (RI=1.38-1.49), biological safety, and biocompatibility for tissue preservation (see supplemental experimental procedures). To test RIMS, PACT-processed samples were mounted in 80% glycerol, FocusClear, or RIMS, and then imaged under identical conditions (FIG. 9A). RIMS provided good optical clarity for fluorescence microscopy (FIG. 9C) and caused minimal quenching of the eYFP signal over a 3-month period (FIG. 9E). Since its performance appeared to be on par with or better than FocusClear (FIG. 9A) and it provided a >10-fold reduction in mounting costs, RIMS was employed for all subsequent PACT and 8 PARS experiments. The exact RIMS formulation can be optimized in a case-specific manner to the RI of tissue samples (FIG. 9B).

Whole-Body Clearing Using the Vasculature in Adult Rodents

The PACT protocol uses a 4% acrylamide monomer solution to generate the final tissue hydrogel and results in a good combination of protein preservation, speed and ease of clearing, and optical clarity. However passive diffusion is slow, prohibitive for large volume or whole organism clearing. It was also noted that the acrylamide hydrogels markedly swelled during the detergent clearing phase (FIG. 1A, 7C). These two drawbacks, common to most clearing protocols, prompted the development of an alternate methodology to speed up clearing and also to minimize tissue expansion during clearing. The existing vasculature networks were utilized, as is done regularly in cardiac perfusion-fixation (Gage et al., 2012; Jonkers et al., 1984), to introduce agents directly to tissue by performing the entire fixation and clearing procedure in situ. This method is termed Perfusion-Assisted Agent Release in Situ (or PARS). PARS utilizes the intact vasculature of the animal to infuse the hydrogel monomer and clearing solutions directly, which then diffuse throughout the tissues of interest. To investigate both whether major blood vessels and whole-organism microvasculature was accessed by the perfusate (Leong and Ling, 1990; Li et al., 2012), AlexaFluor 647-conjugated antibodies against mouse immunoglobulin (FIG. 10B, right) or Atto 488-conjugated nanobodies against GFAP (FIG. 10B, left) were perfusion-recirculated through cardiac catheters for 24 hours. The mouse brain vasculature was extensively labeled, illustrating the accessibility of blood vessels to perfusate (FIG. 10B). Perfusate was also observed to diffuse into surrounding tissue, as shown by the extravasculature GFAP labeling (FIG. 10B).

Figure 3:
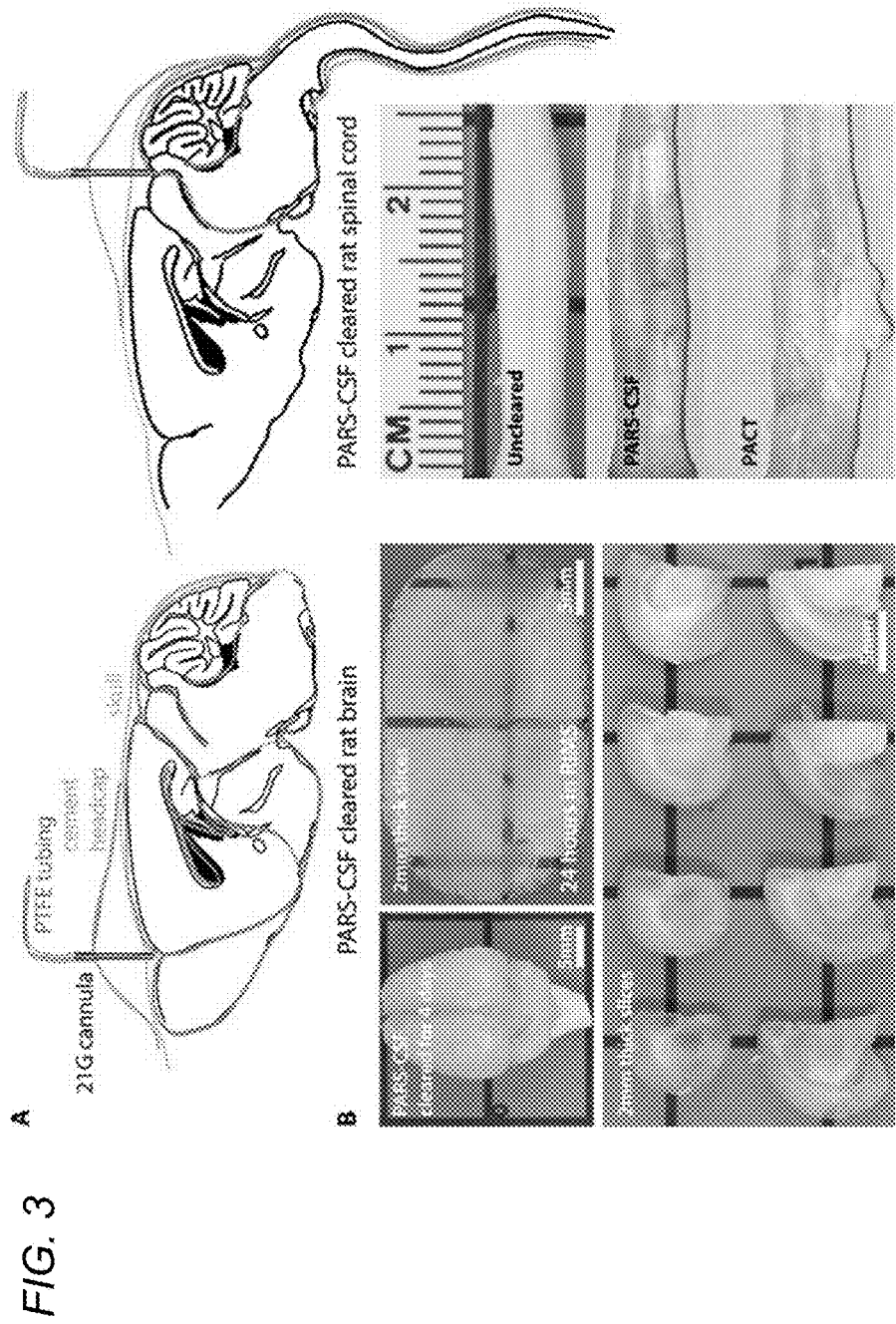
FIG. 3 demonstrates, in accordance with an embodiment of the invention, PARS-CSF: a protocol for rapid whole-brain or spinal cord clearing and labeling via the cerebrospinal fluid route (CSF) using perfusion-assisted agent release in situ (PARS). (A) CNS tissue may be rendered transparent optically transparent by the direct perfusion of all PARS reagents into the CSF via an intracranial brain shunt inserted either (left) below the dura in the region directly above the olfactory bulb, or into the cisterna magna (or placed directly above the dorsal inferior colliculus, right). The cannula, which is connected to the perfusion lines may be cemented into position with dental acrylic. (B) Whole-brain and the corresponding 2 mm thick slices (left) and whole-spinal cord (right) from PARS-CSF rats that were cleared at 37° C. for 4-days (brain) or for 2-weeks (spinal cord) are shown. The extent of whole-brain clearing is dependent on brain tissue proximity to the cannula: the frontal lobe was rendered optically transparent, whereas the mid-hind brain were only weakly cleared (see 2 mm slices on right side of panel). After 24-hour incubation in RIMS, PARS-CSF brain slices were sufficiently cleared for imaging without further sectioning. C) Images show native eGFP fluorescence in 500 μm PARS-CSF cleared coronal brain slices prepared from mice that, 6-months prior to clearing, received IV injections with AAV9:CAG-eGFP. Representative sections of cortex and hippocampus are presented at higher magnification in image boxes (right). In the layer V coronal view, an AAV9 transduced eGFP-expressing glial cell and eGFP-neuron adjacent to a blood vessel are clearly visible. In the hippocampus (bottom), the finer neuronal processes of eGFP-expressing CA1 neurons may be visualized with high resolution, which suggests that PARS-CSF may be completed without severe damage to cellular morphology. For microscopy see Methods. Also see FIG. 10.
Figure 3:
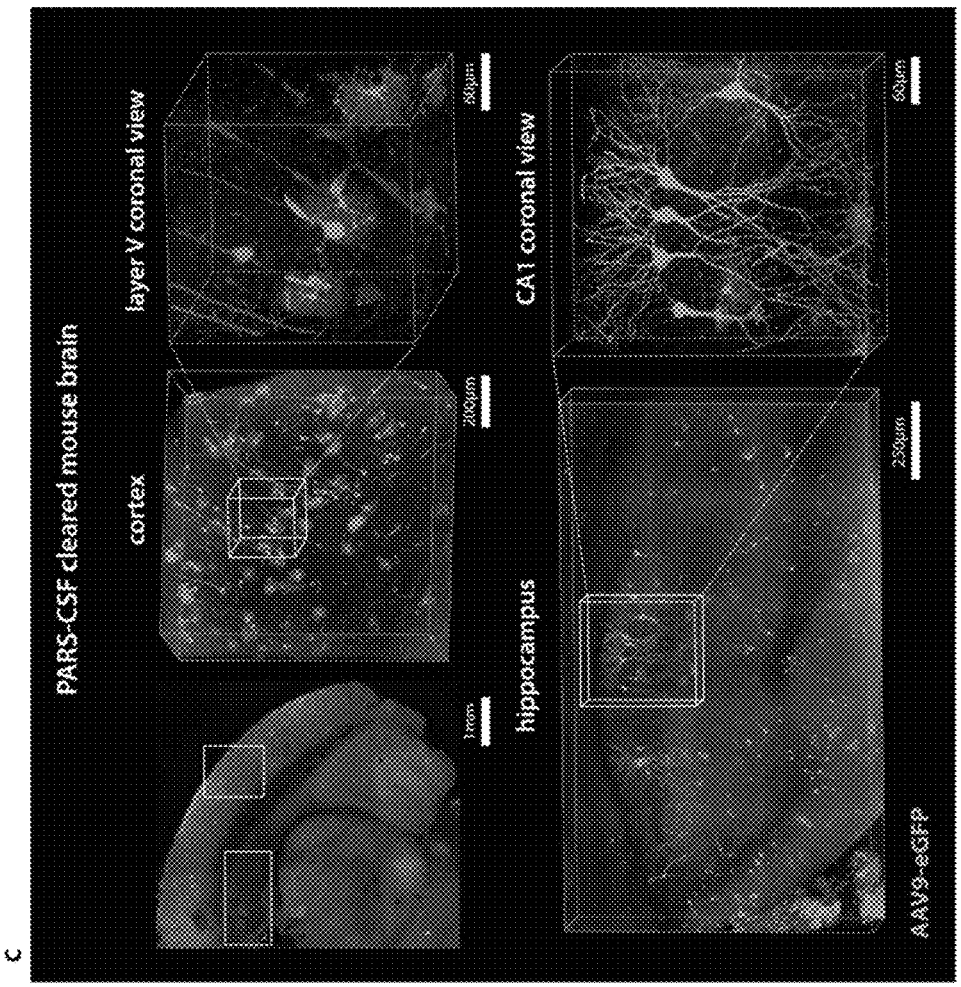

To recirculate PACT reagents into brain CSF or through whole-body vasculature for several days-to-weeks a closed-loop perfusion system was developed. Using this custom PARS chamber (FIG. 10A), continuous intracranial perfusion of 8% SDS into CSF, via a method termed PARS-CSF (FIG. 3), attained wholebrain clearing in 4 days (FIGS. 3A-3B). Inserting the cannula more caudally into the cisterna magna (FIG. 3A, right) granted clearing of the entire length of the rat spinal cord (FIG. 3B). Next, AAV9-eGFP injected adult mice were prepared with a subdural cannula inserted directly above the olfactory bulb (FIG. 3A, left), and after 4 days of recirculating 8% SDS at 37° C., both unmyelinated and densely myelinated mouse brain regions near CSF circulation (most parts of the cortex, hypothalamus, regions near the ventricles and spinal cord) were transparentized). GFP-labeling of individual neurons, neuronal processes, and glial cells was clearly visible throughout the brain (FIG. 3C).

It was determined that the same perfusion-clearing method of PARS-CSF could be extended to clearing whole-bodies in situ. Furthermore, the application of a pressure gradient on tissue during the lipid extraction and antibody diffusion, respectively, could hold the added benefit of accelerating the clearing and immunolabeling steps relative to PACT-based clearing of individual excised whole-organs. Clearing reagents were cycled through the whole-body vasculature (see timeline, FIG. 4A), with complete clearing of all peripheral organs and of central nervous system accomplished within 1 week and 2 weeks, respectively, for mice and rats alike (FIGS. 4B-4D, 13). The minimal protein content of the PARS perfusate, and the higher protein content of perfusate from A0P4-infused mice (FIG. 4E) suggested that the whole-organism hydrogel polymerization was both necessary and sufficient to stabilize gross organ structure and macromolecular content. To confirm that PARS was compatible with visualizing localized fluorescent protein expression in sparsely labeled cells in multiple organs, a GFP transgene was delivered by systemic administration of adenoassociated virus (AAV). AAV9:CAG-eGFP (FIG. 5D) or AAV9BD1:CAG-eGFP, a variant of AAV9 that transduces CNS neurons to a similar extent as AAV9, but exhibits reduced astrocyte and hepatocyte transduction (FIG. 5E) were delivered via the vasculature in adult mice. In both the brain and the liver, native eGFP expression was readily detectable and the reduced transduction of liver hepatocytes by AAV9BD1 as compared with AAV9 was easily detected (FIG. 5D versus 5E).

Figure 4:
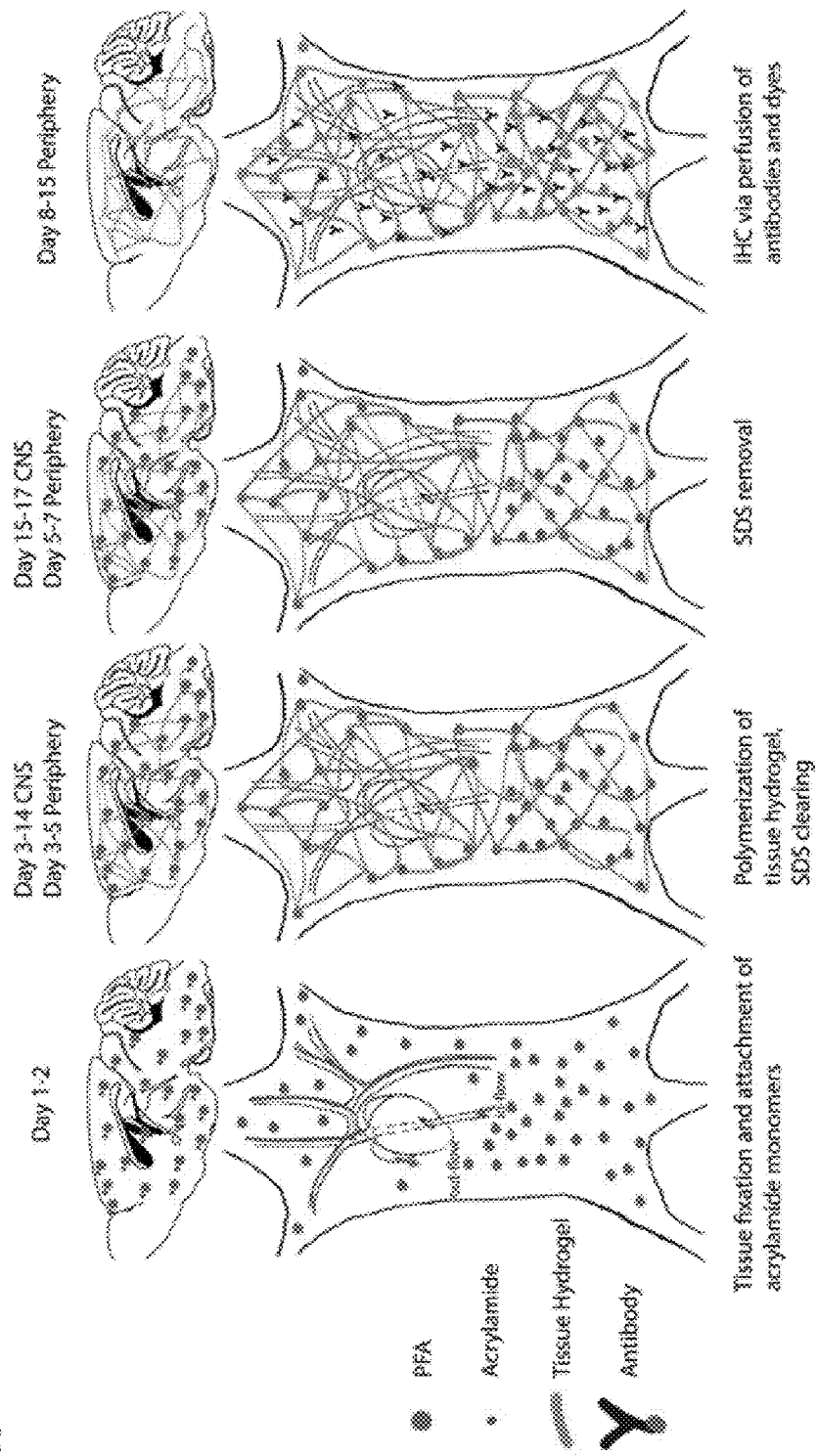
FIG. 4 demonstrates, in accordance with an embodiment of the invention, PARS achieves whole-body clearing. (A) Schematic of PARS clearing and immunostaining. (B) A comparison of optical transparency of mouse brains and peripheral organs before and after PARS clearing. (C) Representative images of relative mouse brain size before (first box, from left) and after (second box) 2 weeks of PARS clearing shows that PARS circumvents hydrogel swelling and brain tissue expansion during the clearing process. Brain tissue expands gradually after immersion in RIMS (third box); this volume change may be mitigated via post-fixing PARS samples in 4% PFA overnight prior to RIMS mounting (fourth box). (D) Representative images of relative rat brain size before (right) and after (left) 4-days of PARS clearing, showing how PARS is a scalable method. Coronal slices of rat whole-brain samples show gross tissue morphology, highlighting that unmyelinated areas may be cleared within 4-days of PARS-based clearing. (E) Protein loss of PARS clearing compared to other clearing methods (n=4 mice for each); graph shows mean±s.e.m.; one way ANOVA followed by Bonferroni posthoc test was used to determine statistical significance in comparison 20 to A4P0 8% SDS PARS clearing. * indicates $p<0.05$ and ** indicates $p<0.01$. Images for (B-D) were taken using bright field camera. Also see FIGS. 10, 13, and 9E.
Figure 4:
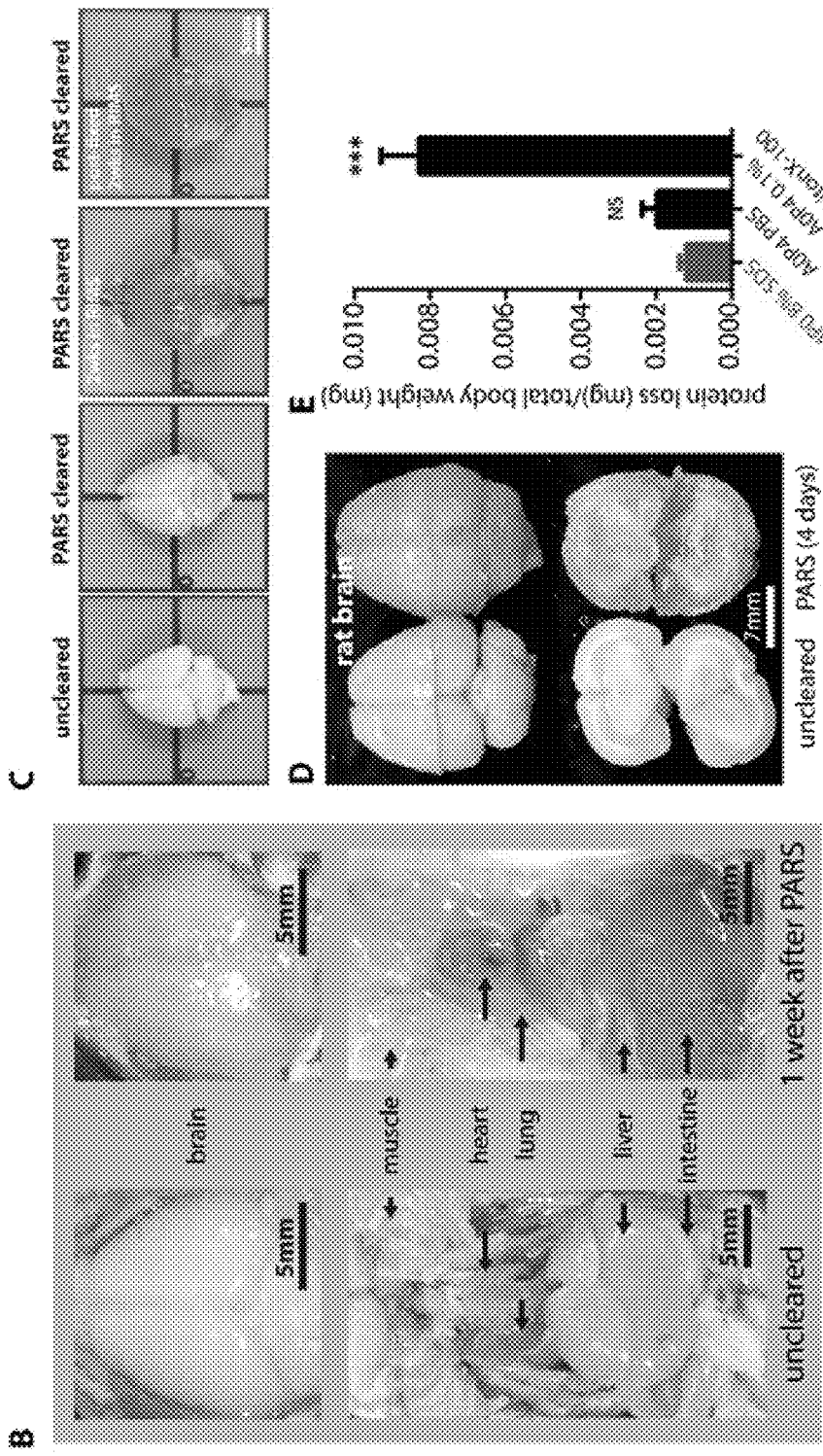
Figure 11:
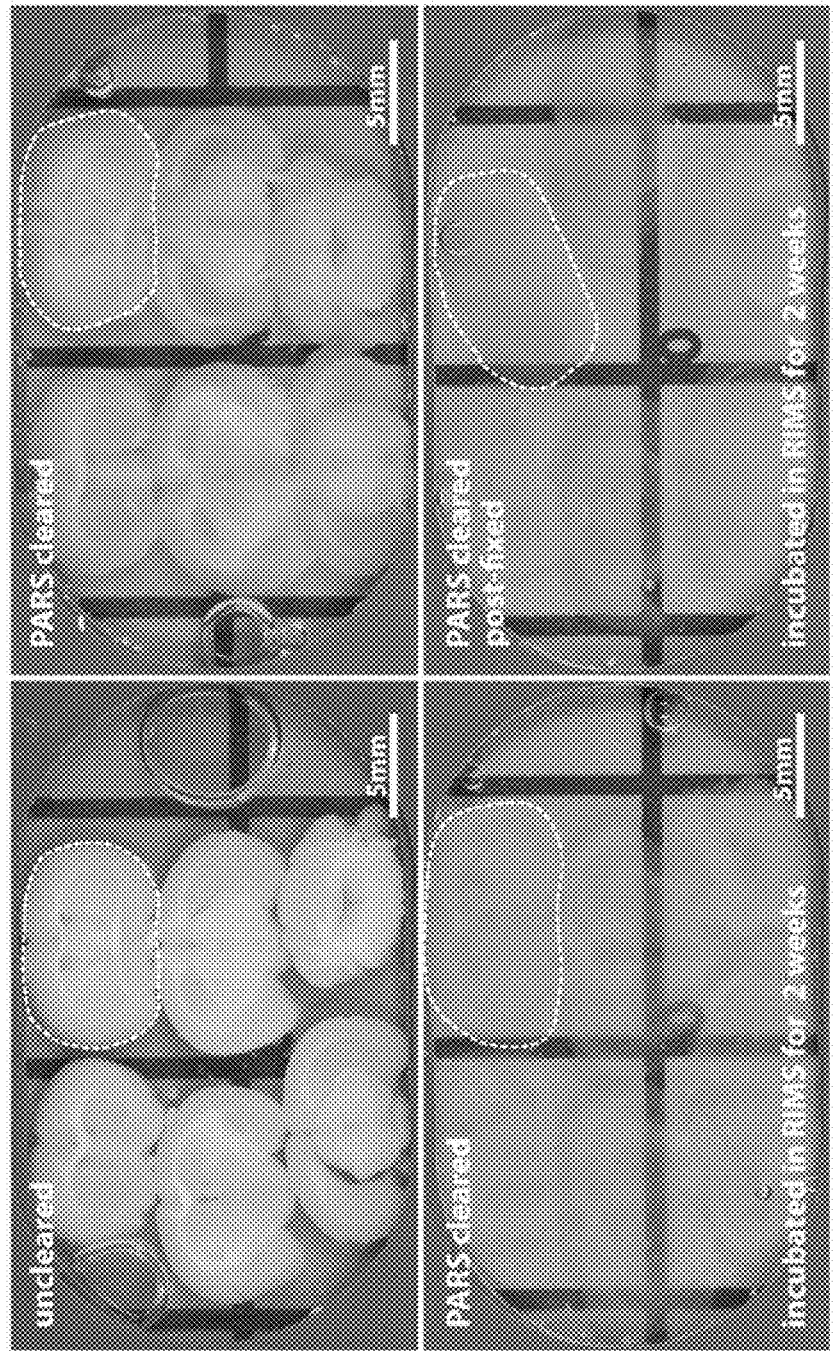
FIG. 11 demonstrates, in accordance with an embodiment of the invention (related to FIGS. 4 and 5), tissue preservation and quantification. (A) Bright field images of 1 mm thick mouse brain slices from uncleared (top left), PARS cleared (top right), PARS cleared and 2-week RIMS immersion (bottom left), and PARS cleared, 4% PFA post-fixed and RIMS mounted mouse brain sections. Note the slices are from the whole brains in FIG. 4C. (B) The mean nearest neighbor distance between cells in the cortex, striatum and thalamus were quantified in uncleared, PARS cleared, and PARS cleared then post-fixed brains slices. Compared to the uncleared control, PARS cleared brain slices showed a small but significant increase in cell spacing in all three regions of the brain and significant increase in cell size in the cortex and thalamus while PARS cleared then post-fixed brain slices did not. Statistical significance: for paired samples: 2-tailed Student's t test; for multiple comparisons: one-way ANOVA ($p<0.01$, *$p<0.005$, and ****$p<0.0005$, ns=not significant).
Figure 11:
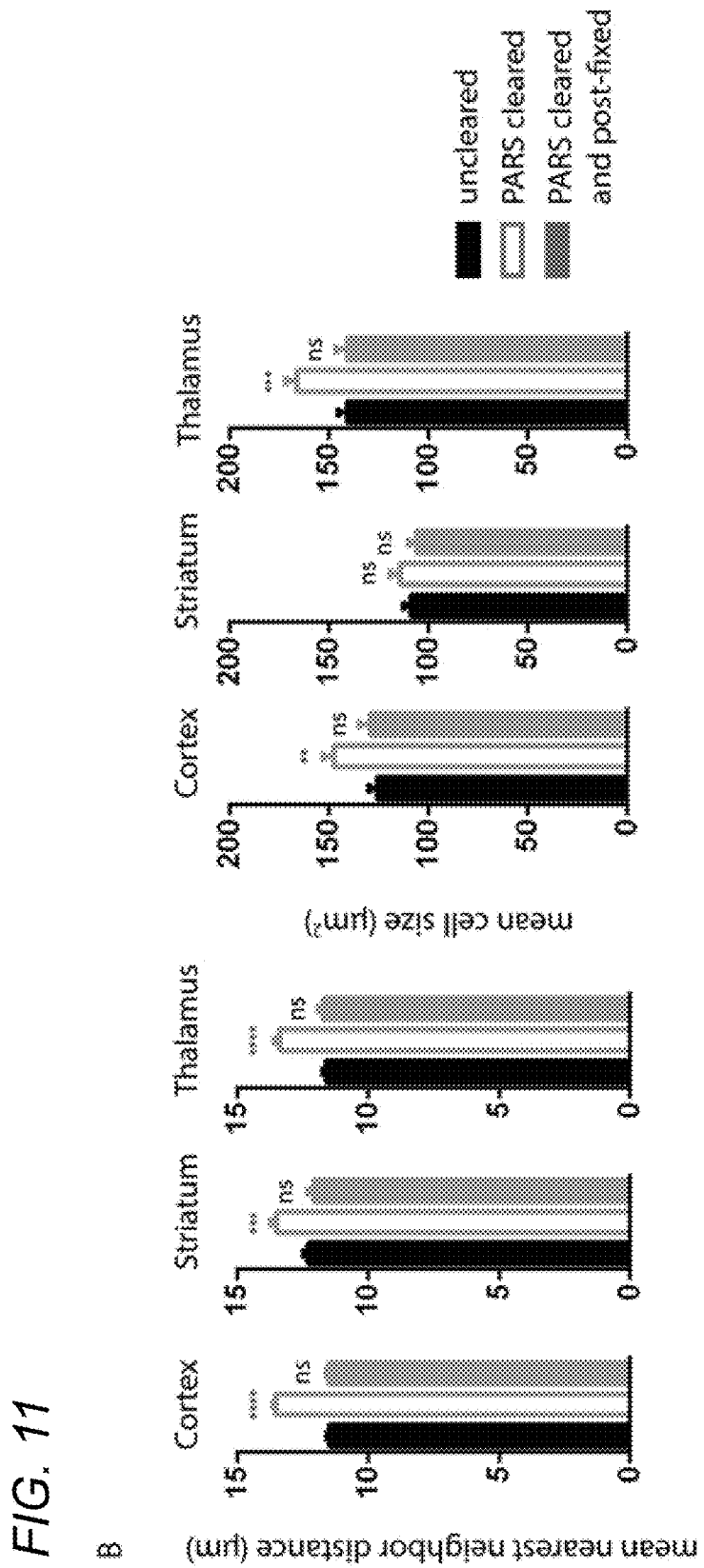

In comparison to PACT, it was predicted that tissue volume changes during PARS processing would be reduced since musculoskeletal structures, such as the skull, the vertebral column, and muscle walls, would physically constrain tissue expansion. Indeed, PARS-based clearing of rodent brains was accomplished with limited hydrogel swelling and tissue expansion during clearing (FIG. 4C-4D, 11A). Although PARS-processed brains do swell slightly following their extraction from the skull and placement in PBS or RIMS (FIG. 11A), there was no evidence to suggest that gross changes in neuronal morphology occurred as a result of PARS processing and post-PARS expansion (FIG. 5B). Nevertheless, mitigation of tissue swelling in RIMS was attempted through post-fixing PARS samples in 4% PFA overnight prior to RIMS mounting. To assess the extent to which overall tissue architecture was altered by volume changes, the intercellular distance and the average cell size within different brain regions (cortex, striatum, thalamus) of uncleared, PARS-cleared, and post-fixed PARS-cleared samples was measured (FIG. 11B). It was predicted that individual regions may be differentially affected by PARS processing or RIMS incubation; for example, any sheer forces originating from perfusion-related intracranial pressure may exert a greater insult on less myelinated tissue or cause ventricle collapse. Post-fixing PARS samples significantly prevented the increased cell-sizes and intercellular distances that were detected throughout PARS samples. There were no significant differences in cell size or intercellular spacing between uncleared and post-fixed samples in all brain regions assayed (FIG. 11B).

Figure 5:
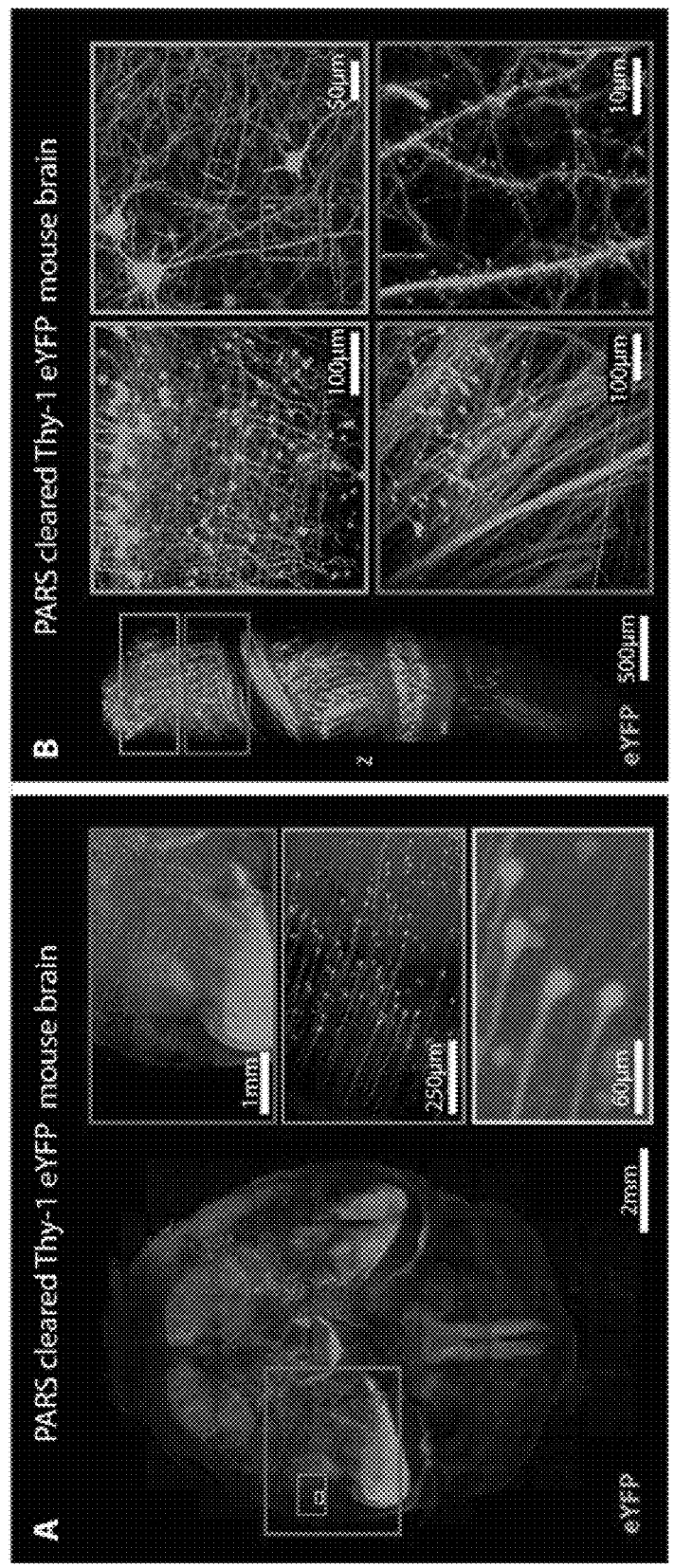
FIG. 5 demonstrates, in accordance with an embodiment of the invention, PARS enables whole-brain mapping of widespread and sparse genetically encoded fluorescent signals with subcellular resolution. (A) Whole brain image (z=6 mm), and (B) deep-brain imaging (z=4 mm) of adult Thy1-eYFP mouse after PARS clearing for 10 days. The boxes on the right show high magnification images of indicated areas. (C) Spinal cord image of adult Thy1-eYFP mouse after PARS clearing for 2 weeks (z=2 mm). Lower panel shows high magnification images of indicated region (z=1.2 mm). (D) Images show native eGFP fluorescence in 1 mm coronal brain slices (left) and liver (right) prepared from the PARS cleared mice that received IV injections of AAV9:CAG-eGFP. Image columns to the right of each coronal brain image show the orthogonal views (z=0.5 mm). (E) Native eGFP fluorescence in 1 mm coronal brain slices (left) and liver (right) prepared from PARS cleared mice injected with a liver detargeted variant, AAV9BD1:CAG-eGFP. Image columns to the right of each coronal brain image show the orthogonal views (z=0.5 mm). For microscopy see Methods. Also see FIG. 11.
Figure 5:
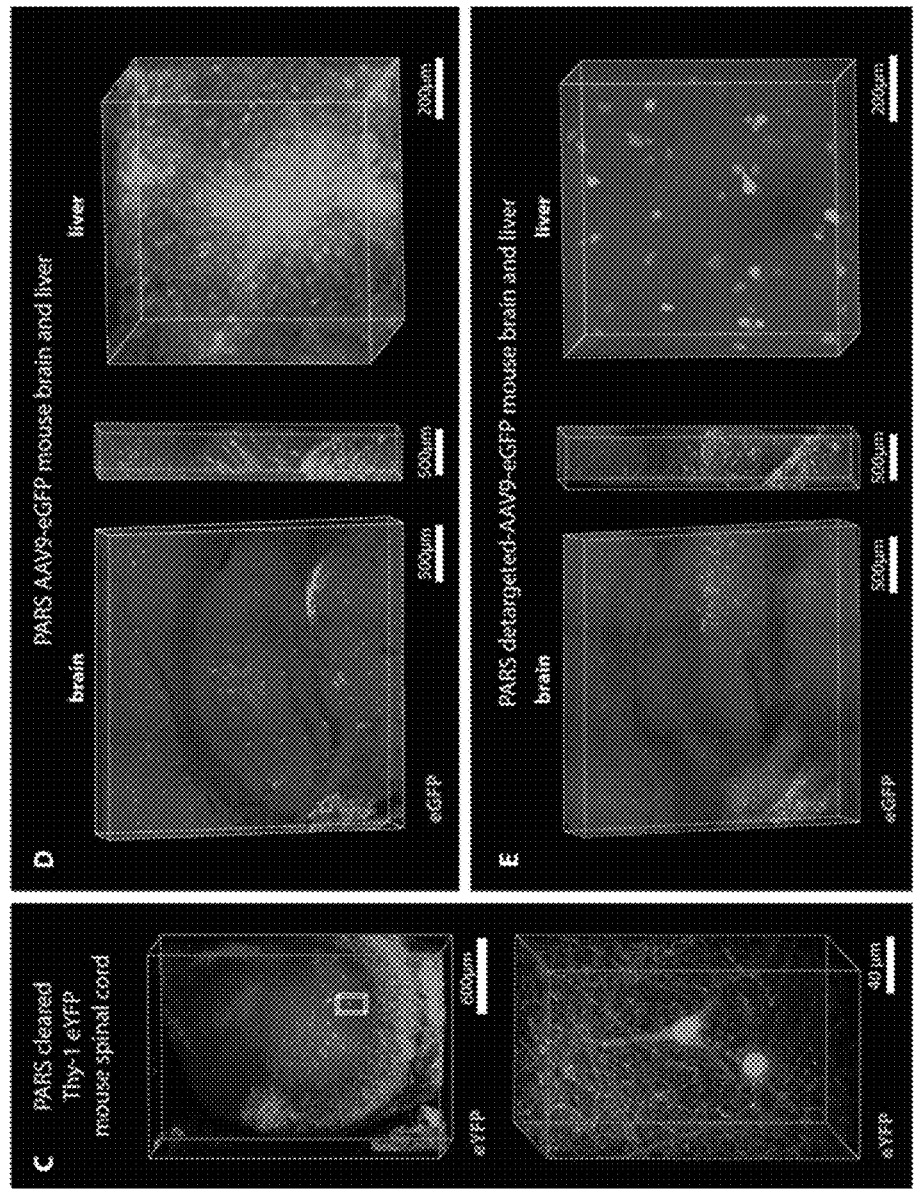
Figure 6:
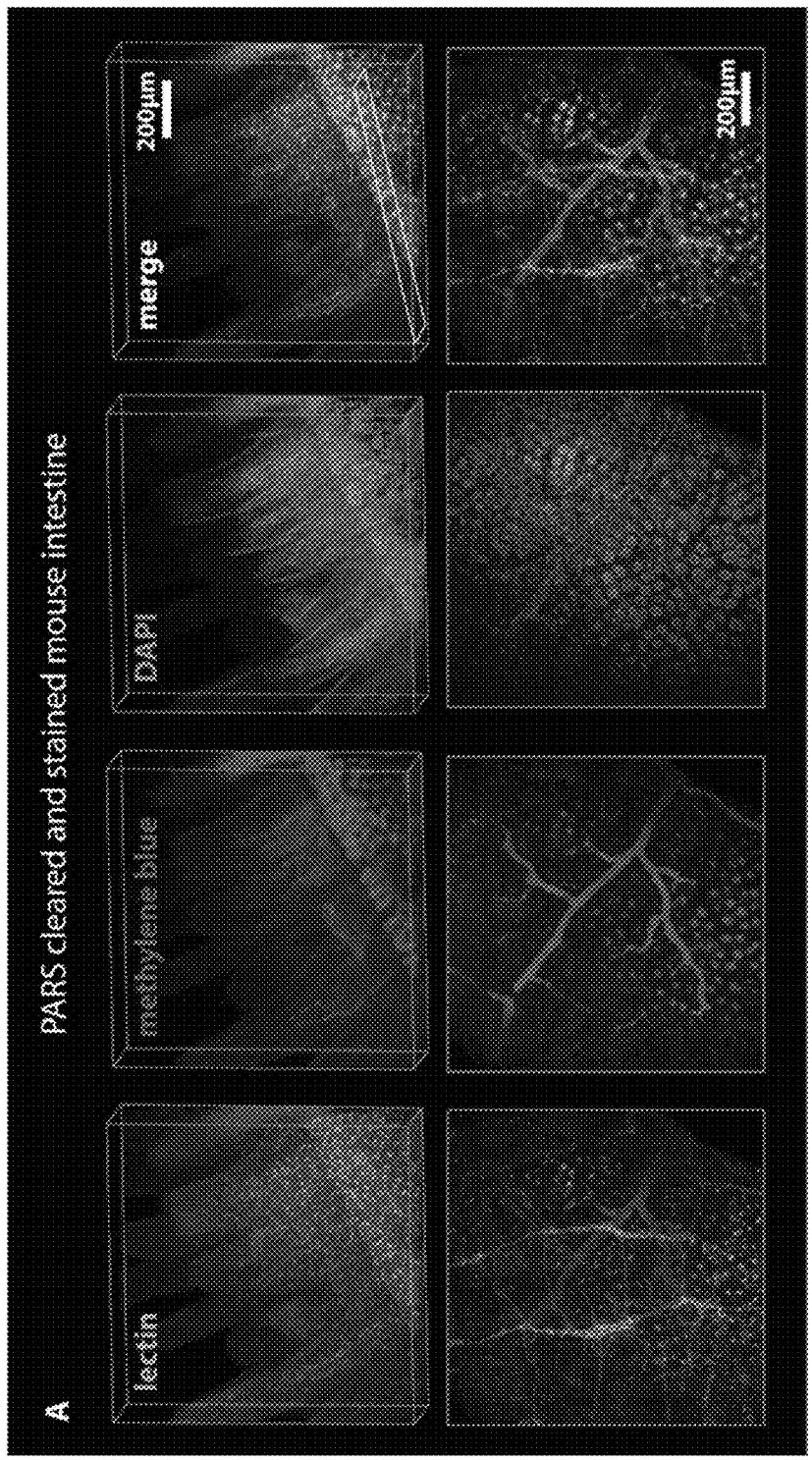
FIG. 6 demonstrates, in accordance with an embodiment of the invention, PARS allows rapid and uniform clearing and immunolabeling of peripheral organs. Clearing and immunohistochemical labeling was achieved in whole mice through PARS alone. (A) PARS-cleared mouse intestine was stained with lectin, methylene blue, and DAPI, and imaged through a depth of 500 μm. Lower panels shows maximum intensity projection of above rendering, z=50 μm. (z=500 μm). (B) A 1 mm thick kidney section was imaged (left) for anti-tubulin antibody and DRAQ5 labeling. Right panels show high magnification images of the indicated region and the structure of glomeruli, demonstrating that PARS enables antibody-based labeling throughout the kidney (z=1.2 mm). For microscopy see Methods. Also see FIGS. 12 and 13.
Figure 6:
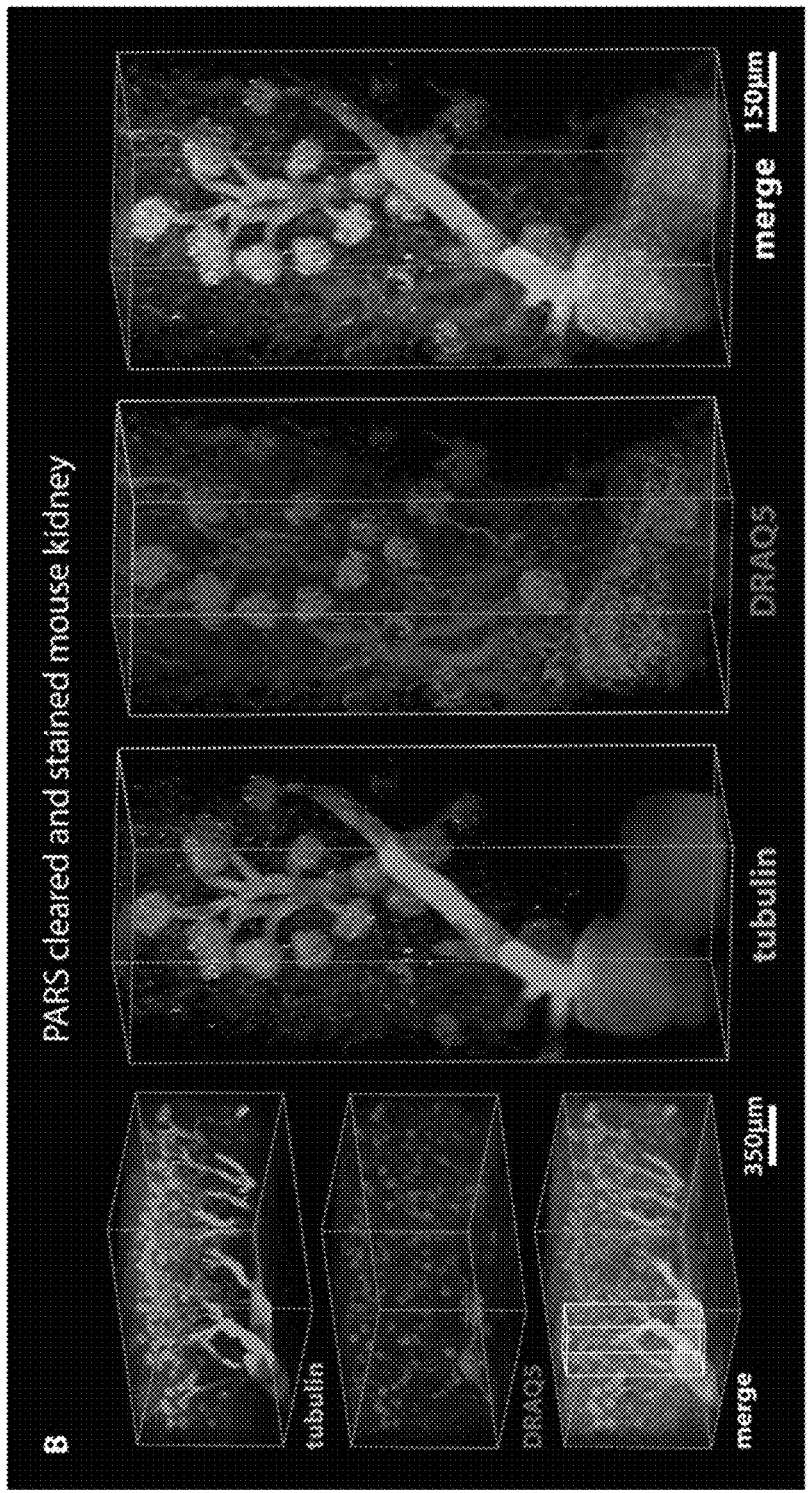
Figure 12:
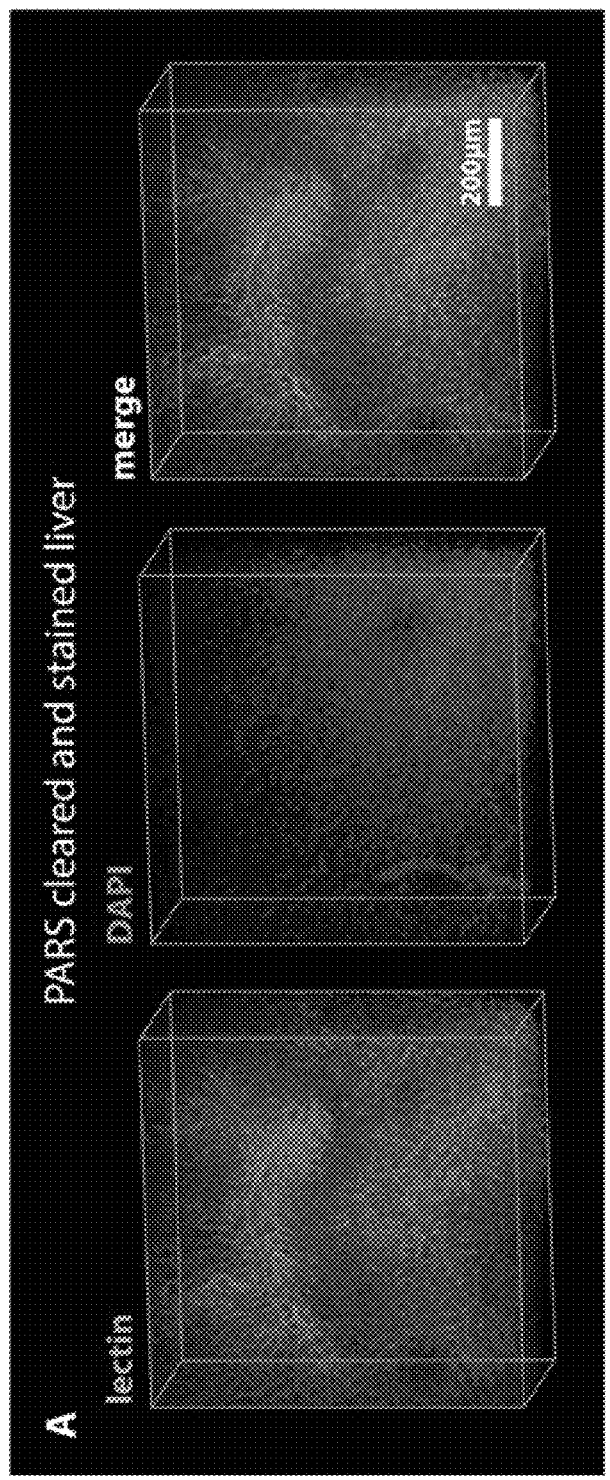
FIG. 12 demonstrates, in accordance with an embodiment of the invention (related to FIG. 6), PARS renders major peripheral organs optically transparent. Following 1-week of PARS clearing and perfusion-labeling, peripheral organs were excised, cut into 1-2 mm sections, and immersed in RIMS for 24 hours before imaging. (A) 500 µm imaging stack of PARS cleared and stained mouse liver sample, with diffuse lectin and DAPI staining suggesting that PARS reagents were able to access the entire organ, despite the density of liver tissue. (B) 100 µm imaging stack of PARS cleared and stained mouse lung sample and (C) 600 µm thick imaging stack of PARS cleared mouse pancreas sample, both exhibiting high-level lectin, phalloidin and DAPI fluorescent signals throughout. Fine resolution of cellular structures were observed in all three tissue samples. Lectin staining, which marks blood vessels, in combination with the fluorescent signals of other small-molecule dyes demonstrate that stained tissue is in the immediate vicinity of tissue vasculature. In peripheral organs, immunolabeling occurs via both vasculature circulation and passive diffusion of perfusate leaks into tissue surrounding vasculature. (z=100 µm, scale bars=100 µm). For microscopy see Methods.
Figure 12:
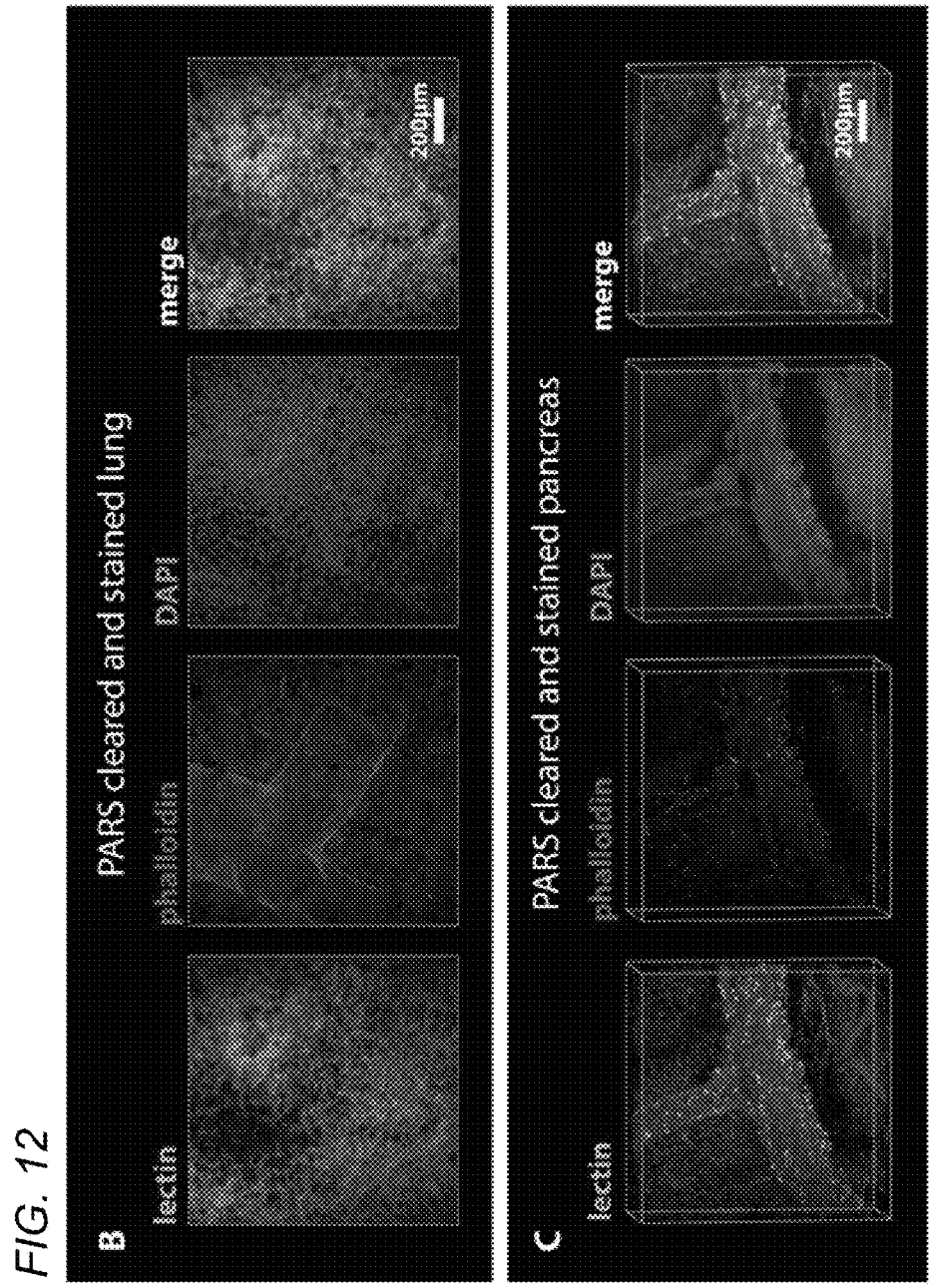
Figure 13:
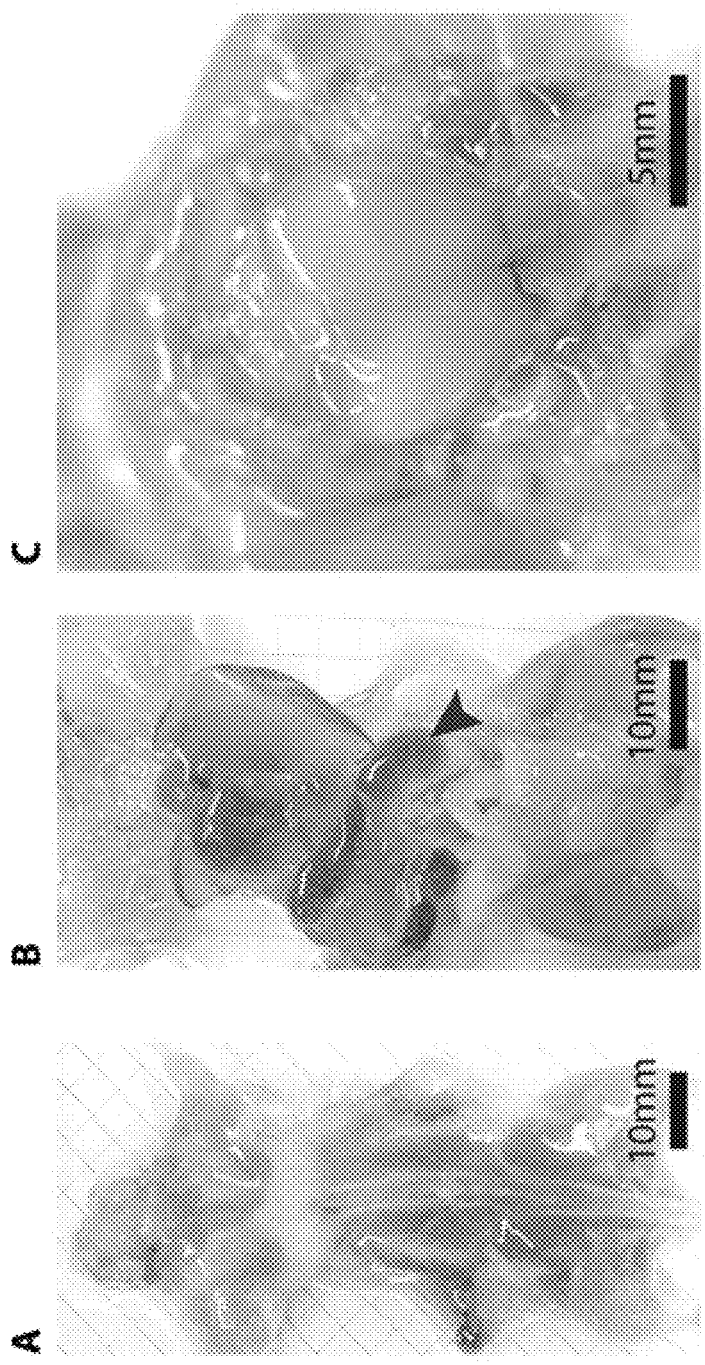
FIG. 13 demonstrates, in accordance with an embodiment of the invention (related to FIG. 4), PARS is capable of whole-body clearing. The (A) dorsal and (B) ventral view of whole Thy1-eYFP mouse after PARS clearing with 8% SDS for 1 week showed good optical transparency of whole body. Arrowhead in (B) points to cleared kidney. (C) The image of the brain for the same mouse. Images were taken using bright field camera.
Figure 14:
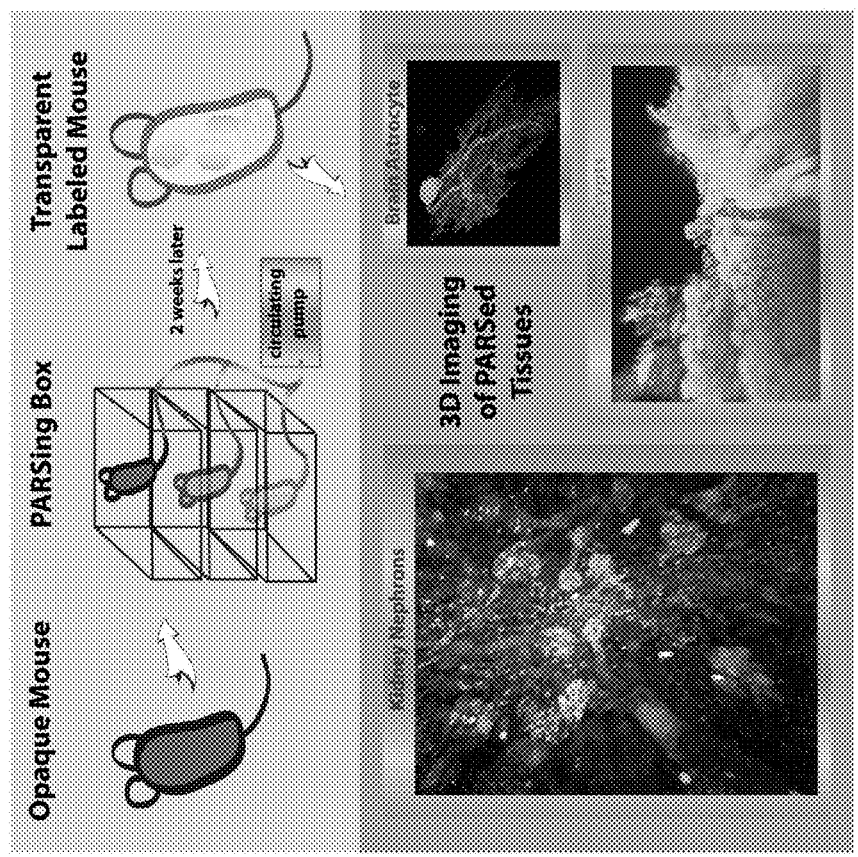
FIG. 14 demonstrates, in accordance with an embodiment of the invention, implementation of PARS and subsequent 3D imaging.

Whole-Organism PARS Enables Phenotyping and Imaging in an Organ-by-Organ Fashion Following whole-body PARS processing and labeling, major organs were excised, thick-sectioned and imaged using confocal microscopy (FIGS. 5, 6, 12). The PARS-cleared whole-brain (FIGS. 5A-B) and spinal cord (FIG. 5C) of Thy1-eYFP mice were imaged, and it was determined that the PARS processing rendered entire organs optically transparent to the extent that visualizing deep-tissue structures with cellular resolution was possible. Through visualizing individual neurons and nephrons throughout the cleared whole-brain (FIGS. 5A-B) and kidney (FIG. 6B) respectively, it appears this optical clarity was achieved while leaving fine cellular structures intact, in part due to the success of in situ tissue-hydrogel polymerization in stabilizing tissue architecture, preserving protein content and endogenous fluorescence, and maintaining the spatial relationships between subcellular and cellular tissue components (FIGS. 5A-B). For example, individual fluorescently-labeled glomeruli of individual nephrons were resolved, which establishes the ability of PARS to access peripheral organs through intact vasculature (FIGS. 6B, 12).

Importantly, this includes the delivery of all immunohistochemical solutions as well, including blocking solutions, primary and fluorescently-labeled secondary antibody cocktails, or fluorescently-labeled small-molecules, and wash buffers. Immunolabeling using PARS was target-specific, uniformly distributed throughout peripheral organs, and exhibited low background, as illustrated by the tubulin and DRAQ5 labeling in PARS-processed mouse kidney sections (FIG. 5B) and by the perfusion-based labeling of blood vessels in the liver, lung, pancreas with lectin, the filamentous actin probe phalloidin, and the nucleic acid stain DAPI (FIG. 12).

Example 2

Discussion

In some embodiments, the invention teaches PARS, a method that renders intact whole-organisms transparent for imaging with single cell resolution while preserving fluorescent and protein-based signals and tissue architecture. The starting point, the CLARITY method (Chung et al., 2013) provided scientists with a brain-processing platform for elucidating the 3D cellular arrangement and connectome in toto. Numerous laboratories have previously reported on new clearing reagents in the decade before CLARITY, however many of these reagents were highly application- or tissue-specific (summarized in Table 1). In contrast, CLARITY introduced two broadly applicable techniques pertaining to tissue preservation (hydrogel embedding) and clearing efficiency (electrophoretic tissue clearing, ETC), both of which could be incorporated into the design, or redesign, of other clearing procedures.

Traditionally, making tissue transparent was a process that demanded solvent incubations on the order of weeks-to-months, as reported in other clearing protocols (Hama et al., 2011). ETC, however, challenged the prevailing view that the rate of tissue clearing could only be accelerated through assaying large panels of organic solvents for their ability to solubilize tissue rapidly. Oftentimes, candidate solvents tested in these screens achieved rapid tissue clearing, but compromised tissue structure (Hama et al., 2011) or quenched native fluorescence (Becker et al., 2012; Erturk et al., 2012; Susaki et al., 2014b). Although the reagents introduced by CLARITY are gentler by comparison, the needed ETC step for fast clearing is complex to implement and causes tissue degradation from sample heating. Although these challenges can be bypassed by the use of passive CLARITY (Tomer et al., 2014) the slow rate of clearing make the technique impractical for scaling up or for whole-body mapping.

With the goal of rapidly clearing whole organisms while still using mild detergents and fluorescence nonquenching reagents throughout, PARS was developed on the basic principles of CLARITY, but aimed to bypass the need for ETC, while maintaining faster clearing than through passive diffusion. First, the clearing agents were modified for passive CLARITY by removing bisacrylamide and increasing the detergent concentration to 8% SDS (PACT reagents). The tissue clearing step was redesigned such that the electrophoretic force used by CLARITY to drive fast lipid extraction was replaced with a perfusion-based pressure gradient. Controlled flow of PACT reagents throughout intact tissue vasculature transforms most peripheral organs into optically transparent tissue within 2-3 days, while whole-mouse and whole-rat brains are rendered transparent within 1-2 weeks. Additionally, the self-contained nature of clearing in situ also reduced tissue expansion during the monomer infusion and lipid removal.

PARS allows for whole-organ and whole organism mapping with high phenotypic content. With this in mind, quick, low resolution scanning of large tissue blocks can direct investigators to restricted areas worthy of slow, high phenotypic content analysis, including smFISH; a method that preserves fluorescent markers long-term is particularly valuable in this respect. Both PACT and PARS methodologies are scalable, cost-effective relative to the original CLARITY process and appear to be transferrable to other model organisms or human tissue. Indeed, while PARS was depicted using cardiac perfusion in rodents, the overall methodology could also be applied to instances in which sufficiently large vessels are available for creating a perfusion route, such as whole-organ perfusion in larger, higher order mammals, including isolated human tissue. While PARS achieves increased speed of clearing and reduced swelling without tissue damage (Table 1), another significant strength of the method lies in its scalability. Data demonstrates, for example, that PARS can be employed to assess AAV-mediated transduction at the cellular level in multiple organs after systemic delivery.

By eliminating the need to section individual tissues, the PARS approach could expedite efforts to screen numerous AAV serotypes and/or gene regulatory elements for optimal expression in the cell types of interest. In addition to improving screening throughput and speed, a PARS-based whole-body method could also counteract the risk of underestimating AAV transduction in target tissues due to undersampling errors. Similarly, PARS could improve the understanding of peripheral nerves at their target whole-organs. Accurate maps of complex long-range fiber bundles, such as for the vagus nerve (George et al., 2000), could help inform improvements in existing therapies or spur the development of entirely novel therapeutic strategies, such as for bioelectronics medicines (Famm, 2013). PARS can also facilitate biomedical work in brain-to-body interconnections, in whole-body screening experiments for off- and on-target agents, and in whole-organ mapping for sparse elements such as tumor cells or stem cells. Lastly, the PARS method is compatible with cell-filling endoskeletal structures. By combining PARS with TEMPEST—a precursor to CLARITY (Deisseroth and Gradinaru, 2014)—the in vivo expression of long-lasting keratin filaments (that outlive the cells themselves while keeping a loyal blueprint of the morphology) within populations of interest can facilitate accurate postmortem quantification and mapping of long-degenerated cells throughout the brain.

The methods introduced here build upon prior work in CLARITY to expand tissue clearing and phenotyping to whole organisms by using the intrinsic circulatory system. Because the vascular network is not homogeneous, leading to non-uniform perfusive flow, organs of interest will clear at different rates.

The blood-brain barrier might present a challenge to efficient perfusion-based transport of particularly large molecules such as antibodies (150 kDa) to the brain relative to the periphery. While not wishing to be bound by any one particular theory, to improve perfusion efficiency, one solution likely will be to develop (or utilize when already available) smaller antibody scaffolds for immunolabeling; these include the fragment-antigen-binding format of immunoglobulins (Fab~50 kDa), and nanobodies, single domain antibodies derived from camelid antibodies, whose smaller size (~12-15 kDa) promotes tissue permeability (Harmsen and De Haard, 2007).

Improved imaging platforms would also compliment the recent tissue clearing work. (Becker et al., 2012; Chung et al., 2013; Dodt et al., 2007; ErtUrk et al., 2012; ErtUrk and Bradke, 2013; Hama et al., 2011; Ke et al., 2013a; Kuwajima et al., 2013b; Susaki et al., 2014a). In order to obtain cellular and subcellular information in thick cleared tissue, it is important to utilize refractive index matched, long-working distance objectives while still preserving high numerical aperture. Scanning speed is an additional barrier with cleared tissue blocks taking many days to be fully imaged-resonant scanners or light-sheet microscopy (Tomer et al., 2014) can accelerate the process while retaining high-resolution data.

Given increasing interest in the link between the brain and peripheral organs (Birmingham et al., 2014), it will be important to have an unsegmented view of the whole-body, with structural connections between the brain and peripheral organs left intact. Through the development of PARS and enabling technologies (nanobodies, imaging platforms) it would be likely possible not only to facilitate neuroscientists' overarching goal of creating a brain connectome, but also to facilitate elucidation of a brain-to-body-and-back connectome as well as the phenotyping of every other organ system in the body, healthy or diseased.

Additional Applications

One of skill in the art would readily appreciate that there are multiple ways of constraining organ expansion. Merely by way of non-limiting example, constraining organ expansion via encasing tissue in a slotted or mesh molded chamber, as can be easily produced by 3D printing, could allow for the performance of a hybrid PACT-PARS clearing procedure.

Furthermore, if such a chamber were made of cover-slip grade glass or fiberoptics (Willis et al., 2012) imaging could proceed without the need to completely remove the enclosure, allowing the sample to retain its original shape and size. Indeed, while PARS was described herein using cardiac perfusion in rodents, the overall methodology could also be applied in instances in which sufficiently large vessels are available for creating a perfusion route, such as whole-organ perfusion in larger, higher order mammals, including isolated human tissue.

Further applications of the technology include viral spread mapping and peripheral nervous system mapping.

Another important consideration is that the PARS chamber can be replicated as many times as needed for fast parallel clearing/labeling.

Development of Probes for PARS

To improve perfusion efficiency, one solution will be to develop (or utilize when already available) smaller antibody scaffolds for immunolabeling; these include the fragment-antigen-binding format of immunoglobulins (Fab~50 kDa), and nanobodies (~12-15 kDa), single domain antibodies derived from camelid antibodies, whose smaller size promotes tissue permeability (Harmsen and De Haard, 2007). The current work of researchers to build large nanobody libraries against relevant human epitopes for biomedical applications will encourage the adoption of CLARITY, PARS, CUBIC, and other similar methods by scientists whose research is dependent on sensitive labeling of sparse targets. One of skill in the art would further appreciate that monobodies could be used in conjunction with the inventive methods and compositions described herein.

Additional Biomedical Applications Uniquely Enabled by PARS and PACT

PARS could allow for refining our understanding of peripheral nerves at their target organs, as well as to facilitate mapping of brain-body interconnections. With respect to the former, accurate maps of complex long-range fiber bundles, such as for the vagus nerve (George et al., 2000), could help inform improvements in existing therapies or spur the development of entirely novel therapeutic strategies, such as for bioelectronics medicines (Famm, 2013). Herein, potential applications include the study of how neural circuits detect pain in peripheral organs (Iyer et al., 2014) or even modulate cancer outcome in the periphery (Magnon et al., 2013). With respect to the latter, neural activity may also have profound effects on peripheral plasticity and motor function. For example, premotor cortex stimulation has been shown to trigger oligodendrogenesis and myelination, and this nerve- and neuroplasticity correlates with improved motor function of the corresponding limb (Gibson et al., 2014). In diseases characterized by an identifiable neuroanatomical pathology, such as demyelinating disorders (multiple sclerosis, or lesions following traumatic brain injury) or psychobehavioral pathology (autism), PARS may be used to pan for peripheral symptoms of disease, such as peripheral nerve demyelination (Zoukos et al., 1992) or peripheral immunoactivation (Hsiao et al., 2012; Hsiao and Patterson, 2011; Lucas et al., 2006; Zoukos et al., 1992) respectively. Other recent depictions of brain-body interconnections relevant to neurodevelopment are the placenta-fetus connection (Hsiao and Patterson, 2012), the brain-gut axis, and the gut microbiota (Flight, 2014) for autistic (Hsiao et al., 2013) or anxiety (Foster and McVey Neufeld, 2013) behaviors.

Likewise, many peripheral anatomical maps lack fine-scale resolution within a whole-organ framework. For instance, although studies have shown that the formation of biofilms were associated with many chronic infections in humans, such as middle-ear infections (Hall-Stoodley et al., 2006) and catheter-associated urinary tract infections (Cole et al., 2014), due to the surrounding thick extracellular polymeric substances and the high complexity of different layers in biofilms, methods for imaging the structure of biofilms within tissues are still limited (Ramsey and Wozniak, 2005; Tan et al., 2014). Such imaging capabilities would be highly beneficial, however, given reports that antibiotics cannot easily penetrate biofilms to remove harmful bacterial infections in the human body (George et al., 2009; Jain et al., 2008). In addition, high resolution of structural information of peripheral tissues also helps us to study stem cell niches that are sometimes sparsely embedded in the tissues, such as for the microenvironment signaling regulation of intestinal stem cells located in small intestinal crypts (Bach et al., 2000; Barry et al., 2013).

Importantly, PARS can also facilitate whole-body screening of therapeutics for off-target and on-target binding, and for imaging the biodistribution of administered agents as a method for the qualitative determination of their pharmacokinetic-pharmacodynamic (PK/PD) properties. Along similar lines, data presented herein demonstrates that PARS can be employed to assess AAV-mediated transduction at the cellular level in multiple organs after systemic delivery. By eliminating the need to prepare and section individual tissues, the PARS approach could expedite efforts to screen numerous AAV serotypes and/or gene regulatory elements for optimal expression in the cell types of interest. In addition, whole organ screening using PARS may not only improve the throughput of this PK/PD screening, but could also counteract the risk of underestimating AAV transduction in target tissues due to undersampling errors.

The ability to clear and rapidly phenotype whole-organs could also advance biomedical research and facilitate the study of disease progression by monitoring changes in tissue pathology. A medically relevant use of PARS lays in its application to whole-organ and whole-organism mapping for pathological or diagnostic purposes, such as studying the progressive whole-body physiological changes that occur during disease or developmental states, or mapping tumor architecture, respectively (Birmingham et al., 2014). Various 3D tumor imaging platforms have been reported for tracking cancer progression (Colomba and Ridley, 2014). Despite these new platforms and despite the proven diagnostic utility of anatomic pathology in medicine (e.g. in determining tumor margins (Fukamachi et al., 2010)), conventional histological processing and sectioning of fresh and frozen biopsy samples remains the norm due to cost and time constraints. In most instances, only a fraction of sections are visualized, which can lead to undersampling of critical features and potential misdiagnosis (Zarbo et al., 2005). As highlighted above, PACT- or PARS-based clearing of tissue specimens could help to counteract these risks. Additionally, PARS can also enable the study of whole-tumor morphology in animal models, particularly tissue-level vascularization, heterogeneity in cellular and sub-cellular details throughout the tumor (e.g. margins versus core), and, importantly, metastatic foci across the entire organism. Although a method for tumor clearing (3DISCO (Erturk et al., 2012b)) has been described previously, the extended lifetime for fluorescent markers in RIMS-2 and PARS scalability to whole-organism with ease make PARS a preferred alternative (Table 1).

Finally, the PARS method is compatible with cell-filling endoskeletal structures. For example, one bottleneck in current neurodegenerative research (Parkinson's, Alzheimer's, epilepsy, stroke) is the difficulty to precisely map the distribution of degenerated cells in rodent models since it is impossible to visualize what is long-dead and cleared away by macrophages. In addition, ablation experiments are a popular way to study the causal links between a defined neuronal population (compact or sparsely distributed) and brain activity and behavior: toxins are used to damage such cells but the post-quantification is rarely accurate since it relies on comparing against placebo treated brains and it is impossible to know the exact distribution of ablated cells. By combining PARS with TEMPEST—a precursor to CLARITY (Deisseroth and Gradinaru, 2014)—the in vivo expression of long-lasting keratin filaments (that outlive the cells themselves while keeping a loyal blueprint of the morphology) within populations of interest can facilitate accurate post-mortem quantification and mapping of long-degenerated cells brain-wide.

Example 3

Methods

PACT Clearing

4% paraformaldehyde (PFA)-fixed tissue sections were incubated at 4° C. overnight in the hydrogel monomer solution A4P0 (4% acrylamide in PBS) supplemented with 0.25% photoinitiator 2,2'-Azobis[2-(2-imidazolin-2-yl)propane]dihydrochloride (VA-044, Wako Chemicals USA, Inc.). A4P0-infused samples were degassed with nitrogen for 1-5 minutes and then incubated for 2-3 hours at 37° C. to initiate tissue-hydrogel hybridization. After removing excess hydrogel via brief PBS washes, tissue-hydrogel matrices were transferred into 50 mL conical tubes containing 8% SDS in 0.1M PBS (pH 7.5), and depending on tissue size, were incubated for 2-5 days at 37° C. with shaking. For immunostaining, 1-3 mm thick PACT-processed samples were washed in PBS with 4-5 buffer changes over the course of a day and then transferred to buffer containing small-molecule dyes or primary antibodies followed by fluorescently-conjugated secondary antibody (1:200-400, in PBS containing 2% normal donkey serum, 0.1% TritonX-100 and 0.01% sodium azide) for 3-7 days or with small-molecule dyes for 1-3 days. Antibody or small molecule dye solutions need to be replaced every day. Unbound antibody was removed via PBS washes, as before, and then samples were incubated with secondary antibodies (Fab fragment secondary antibodies are preferred, 1:200-400) for 2-5 days then washed for 1 day in PBS or phosphate buffer (PB) prior to incubation in imaging media (RIMS). All staining and mounting steps were conducted at room temperature with gentle shaking.

Hydrogel Monomer Properties

Although specific hydrogel compositions are reported as used in the experiments conducted herein. The fixative/hydrogel composition may include any convenient hydrogel subunits, such as, but not limited to, poly(ethylene glycol) and derivatives thereof (e.g. PEG-diacrylate (PEG-DA), PEG-RGD), polyaliphatic polyurethanes, polyether polyurethanes, polyester polyurethanes, polyethylene copolymers, polyamides, polyvinyl alcohols, polypropylene glycol, polytetramethylene oxide, polyvinyl pyrrolidone, polyacrylamide, poly(hydroxyethyl acrylate), and poly(hydroxyethyl methacrylate), collagen, hyaluronic acid, chitosan, dextran, agarose, gelatin, alginate, protein polymers, methylcellulose and the like. In some instances, the hydrogel subunits may be modified to add specific properties to the hydrogel; for example, peptide sequences can be incorporated to induce degradation (see, e.g., West and Hubbell, 1999, Macromolecules, 32:241) or to modify cell adhesion (see, e.g. Hem and Hubbell, 1998, J. Biomed. Mater. Res., 39:266). Agents such as hydrophilic nanoparticles, e.g., poly-lactic acid (PLA), poly-glycolic acid (PLG), poly(lactic-co-glycolic acid) (PLGA), polystyrene, poly(dimethylsiloxane) (PDMS), etc. may be used to improve the permeability of the hydrogel while maintaining patternability (see, e.g., U.S. patent application Ser. No. 13/065,030; Lee W. et al. 2010 Proc. Natl. Acad. Sci. 107, 20709-20714). Materials such as block copolymers of PEG, degradable PEO, poly(lactic acid) (PLA), and other similar materials can be used to add specific properties to the hydrogels (see, e.g., Huh and Bae, 1999, Polymer, 40:6147). Crosslinkers (e.g. bis-acrylamide, diazirine, etc.) and initiatiors (e.g. azobisisobutyronitrile (AIBN), riboflavin, L-arginine, etc.) may be included to promote covalent bonding between interacting macromolecules in later polymerization steps.

Hydrogel Network Properties

Typically, the concentration and molecular weight of the hydrogel subunit(s) and modifying agents will depend on the selected polymer and the desired characteristics, e.g., pore size, swelling properties, conductivity, elasticity/stiffness (Young's modulus), biodegradability index, etc., of the hydrogel network into which they will be polymerized. For example, it may be desirable for the hydrogel to comprise pores of sufficient size to allow the passage of macromolecules, e.g., proteins, nucleic acids, or small molecules as described in greater detail below, into the specimen. The ordinarily skilled artisan will be aware that pore size generally decreases with increasing concentration of hydrogel subunits and generally increases with an increasing ratio of hydrogel subunits to crosslinker, and will prepare a fixative/hydrogel composition that comprises a concentration of hydrogel subunits that allows the passage of such macromolecules. As another example, it may be desirable for the hydrogel to have a particular stiffness, e.g., to provide stability in handling the embedded specimen, e.g., a Young's Modulus of about 2-70 kN/m2, for example, about 2 kN/m2, about 4 kN/m2, about 7 kN/m2, about 10 kN/m2, about 15 kN/m2, about 20 kN/m2, about 40 kN/m2, but typically not more than about 70 kN/m2. The ordinarily skilled artisan will be aware that the elasticity of a hydrogel network may be influenced by a variety of factors, including the branching of the polymer, the concentration of hydrogel subunits, and the degree of cross-linking, and will prepare a fixative/hydrogel composition that comprises a concentration of hydrogel subunits to provide such desired elasticity.

Hydrogel Monomers

The fixative/hydrogel composition may comprise an acrylamide monomer at a concentration of from about 1% w/v to about 20% w/v, e.g., about 2% to about 15%, about 3% to about 10%, about 4% to about 8%, and a concentration of bis-acrylamide crosslinker in the range of about 0.01% to about 0.075%, e.g., 0.01%, 0.02%, 0.025%, 0.03%, 0.04%, 0.05%, 0.06%, or 0.075%; or, for example, the fixative/hydrogel composition may comprise PEG prepolymers having a molecular weight ranging from at least about 2.5K to about 50K, e.g., 2.5K or more, 3.5K or more, 5K or more, 7.5K or more, 10K or more, 15K or more, 20K or more, but typically not more than about 50K, at a concentration in a range from about 1% w/w to about 50% w/w, e.g., 1% or more, 5% or more, 7.5% or more, 10% or more, 15% or more, 20% or more, 30% or more, 40% or more, and usually not more than about 50%. Concentrations of hydrogel subunits and modifiers that provide desired hydrogel characteristics may be readily determined by methods in the art or as described in the working examples below.

The fixative/hydrogel solution may be delivered to the specimen by any convenient method, e.g., perfusion, injection, instillation, absorption, application, immersion/submersion, etc. The specimen will typically be fixed in the presence of the hydrogel for 15 minutes or more, for example, for 30 minutes or more, 1 hour or more, 2 hours or more, 4 hours or more, 6 hours or more, 12 hours or more, in some instances, for 16 hours or more, 20 hours or more, or 24 hours or more.

Hydrogel Polymerization

Following fixation of the specimen, the hydrogel subunits can be polymerized, i.e., covalently or physically cross-linked, to form a hydrogel network. Polymerization may be by any method including, but not limited to, thermal cross-linking, chemical crosslinking, physical crosslinking, ionic crosslinking, photo-crosslinking, irradiative crosslinking (e.g., x-ray, electron beam), and the like, and may be selected based on the type of hydrogel used and knowledge in the art. For example, mixing of an un-polymerized or partially polymerized resin with specific crosslinking chemicals results in a chemical reaction that forms cross-links. Crosslinking can be induced in materials that are normally thermoplastic through exposure to a radiation source, such as electron beam exposure, gamma-radiation, or UV light; for example, electron beam processing is used to polymerize the C type of crosslinked polyethylene. Other types of crosslinked polyethylene are made by addition of peroxide during extruding (type A) or by addition of a cross-linking agent (e.g. vinylsilane) and a catalyst during extruding and then performing a post-extrusion curing.

Inhibition of Polymerization Via Free-Radical Scavengers

Many polymers undergo oxidative cross-linking, typically when exposed to atmospheric oxygen. In some cases the reaction is more rapid than desired and thus polymerization reactions may involve the use of an antioxidant to slow the formation of oxidative cross-links. In other cases, e.g., when more rapid formation of cross-links by oxidation is desirable, an oxidizer such as hydrogen peroxide may be used to speed up the process. The length of time for polymerization will depend on the type of hydrogel subunits used and the chosen polymerization method, but will typically be about 15 minutes to about 48 hours, for example, 15 minutes or more, 1 hour or more, 2 hours or more, 3 hours or more, 4 hours or more, 6 hours or more, 12 hours or more, 16 hours or more, 24 hours or more, or in some instances, 48 hours. The optimal time and combination of reagents will be known to the ordinarily skilled artisan or may be determined empirically or from any number of publicly available resources (e.g., on the world wide web at piercenet.com; see also, Macroporous Polymers: Production Properties and Biotechnological/Biomedical Applications. Edited by Bo Mattiasson, Ashok Kumar, and Igor Yu. Galeaev. CRC Press 2010; and Crosslinking Reagents Technical Handbook, Pierce Biotechnology, Inc., 2006).

Clearing

Once polymerized, the hydrogel-embedded (i.e., hydrogel-hybridized) specimen may be cleared. By "clearing" a specimen it is meant that the specimen is made substantially permeable to light, i.e., transparent. In other words, about 70% or more of the visual (i.e., white) light, ultraviolet light or infrared light that is used to illuminate the specimen will to pass through the specimen and illuminate only selected cellular components therein, e.g., 75% or more of the light, 80% or more of the light, 85% or more of the light, in some instances, 90% or more of the light, 95% or more of the light, 98% or more of the light, e.g. 100% of the light will pass through the specimen. This change in the optical properties of the specimen provides for the visualization of cellular and subcellular structures internal to the tissue.

Any treatment that forces cellular components, e.g., lipids, from the specimen, that draws cellular components, e.g., lipids, from a specimen, or that causes cellular components, e.g., lipids, to break down, i.e., dissolve, within a specimen may be used to clear the specimen, including, without limitation, exposure to organic solvents such as xylenes, ethanol or methanol, exposure to detergents such as saponin, Triton X-100 and Tween-20, exposure to ionic surfactants, e.g., sodium dodecyl sulfate (SDS)—especially as described herein, electrophoresis, hydrodynamic pressure, ultrasonic vibration, solute contrasts, microwave radiation, vascular circulation, and the like. In some instances, clearing is performed using a solvent that does not quench fluorescent proteins. Examples of organic solvents that are known to quench fluorescent proteins include tetrahydrofuran, hexane, benzylalcohol/benzylbenzoate (BABB), and dibenzyl ether. Accordingly, in order to preserve the fluorescence of various proteins, in some embodiments clearing is conducted using solvents other than those listed above, e.g., is conducted using non-organic solvents.

RIMS Imaging Media (RI 1.46)

40 g of Sigma D2158 (Histodenz) in 30 ml of 0.02M PB with 0.1% tween-20 and 0.01% sodium azide, pH to 7.5 with NaOH—which results in a final concentration of 88% Histodenz w/v. Samples are incubated in RIMS until transparent (~1 day for PACT samples, up to 1 week for PARS cleared brains), followed by mounting in fresh RIMS.

smFISH

100 µm PACT sections were ethanol-permeabilized, labeled with 24 Alexa 594-labeled 20mer oligo probes towards B-actin (overnight incubation at 37° C.), washed and coverslipped with Slowfade Gold+DAPI according to published protocols (Buxbaum of al., 2014; Lyubimova et al., 2013). Laplacian of Gaussian filtering with a radius of 3 was applied to visualize transcripts in both cleared and uncleared samples.

PARS Protocol

Immediately following standard cardiac perfusion with 4% PFA (in PBS, pH 7.4), the fixed rodent was transferred onto a perfusion chamber (FIG. 10A) which recirculated all subsequent PACT and immunolabeling reagents (as above) continuously (1 ml/min) through rodent vasculature via a peristaltic pump. Perfusion tubing connected the chamber to a feeding needle inserted through the left ventricle into the aorta and loosely sutured in place. The rodent was post-fixed with 4% PFA for 1 hour and then perfusion-washed with PBS for 1 hour. A4P0 monomer was cycled through vasculature overnight, followed by a 2 hour PBS perfusion wash. Before polymerization and without disconnecting perfusion lines, the perfusion chamber was placed into a ziplock bag (FIG. 10A), and the bag containing the chamber with rodent was degassed for 2 minutes under nitrogen gas. Polymerization was initiated via perfusion-recirculation of 200 mL of 0.25% VA-044 initiator in PBS at 37° C. for 2-3 hours. The whole-body was cleared through a ≤2-week perfusion with 8% SDS in PBS, pH 7.5 at 37-42° C. followed by extensive PBS perfusion-washing over 2-3 days. Antibodies and small molecule dyes (as above in PACT) were then delivered via a 3-day perfusion and 1-day wash. For the PARS-CSF variation of brain or spinal cord clearing (FIGS. 3A-B), transcardially-fixed rodents were decapitated and a subdural cannula was inserted above the region of interest and cemented to the skull. All PACT reagents are delivered in the same order and timeframe as PARS at 1 ml/min AAV Production and Systemic Delivery Single stranded ssAAV-CAG-eGFP vectors packaged into AAV9 or the AAV9 variant capsid, AAV2/9BD1, was generated and purified as described (Lock et al., 2010). The AAV2/9BD1 capsid was modified from AAV2/9 (U. Penn) with, amongst others, an N498Y mutation to reduce liver transduction (Pulicherla et al., 2011). $1 \times 10^{12}$ vector genomes (vg) of either virus was delivered intravenously into mice and tissue assessed 6 months later by PARS for native eGFP fluorescence.

Fluorescence Microscopy

Cleared tissue samples were mounted in RIMS at room temperature using spacers from 0.5 mm-7 mm depending on sample thickness (iSpacer, SunJin Lab Co.; Silicone Isolator, Electron Microscopy Sciences, PA) and coverslipped. For FIG. 3B, the samples were imaged by Leica Microsystems using a Leica TCS SP8 two-photon microscope with the Leica HC FLUOTAR L 25×/1.00 IMM CORR objective (working distance, w.d. 6.0 mm). Other images were taken using a Zeiss LSM 780 microscope with either the Fluar 5×/0.25 M27 dry objective (w.d. 12.5 mm), Plan-Apochromat 10×/0.45 M27 air objective (w.d 2.0 mm), LD SC Plan-Apochromat 20×/1.0 Corr M32 85 mm scale-immersion objective (w.d. 5.6 mm), or LD LCI Plan-Apochromat 25×/0.8 Imm Corr DIC M27 multi-immersion objective (w.d 0.57 mm). Image reconstructions were performed using Imaris imaging software (Bitplane). After imaging, samples were stored in RIMS at room temperature.

Extended Supplemental Procedures & Additional Reagents and Buffers

TABLE 1

Methodological Considerations of Major Clearing Protocols of the Last Decade

| Technique | Clearing time for whole-brain | Complete transparency | Fluorescent quenching | Tissues validated | Significant contribution to field | Drawback |
|---|---|---|---|---|---|---|
| BABB, THF, DBE (Becker et al., 2012; Dodt et al., 2007) | hours-days | Yes, but tissue shrinkage | Yes (Ertürk et al., 2012; Ke et al., 2013) | Rodent brain, spinal cord, peripheral tissues | Among first clearing reagents | Harsh reagents (Ke et al., 2013), IHC |

TABLE 1-continued

Methodological Considerations of Major Clearing Protocols of the Last Decade

| Technique | Clearing time for whole-brain | Complete transparency | Fluorescent quenching | Tissues validated | Significant contribution to field | Drawback |
|---|---|---|---|---|---|---|
| ClearT2 (Kuwajima et al., 2013) | days | No | No-partial (Ke et al., 2013) | Rodent brain and embryo | Less quenching than BABB; novel reagents | ~~IHC~~ Immunlabeling only through 120 um |
| Scale (A2, U2) (Hama et al., 2011) | weeks-months (slowest) | Yes, but tissue swelling (Chung et al., 2013; Ke et al., 2013; Kuwajima et al., 2013) | No-minimal (Ke et al., 2013; Kuwajima et al., 2013) | Mouse brain, embryo (Hama et al., 2011) | Transparency without quenching; IHC/F | Slow; tissue deformation; potential protein loss with clearing (Ke et al., 2013) |
| 3DISCO (Ertürk et al., 2012; Ertürk and Bradke, 2013) | <week | Yes | No, but signal decay w/in days (Ertürk et al., 2012; Ertürk and Bradke, 2013) | Peripheral/central organs, embryos, tumors (Ertürk and Bradke, 2013); Central (Erturk et al., 2012) and peripheral (Jung et al., 2014) nerves | Balance between rapidity and quality of cleared tissue; imaging protocol | Requires immediate sample imaging; IHC-very limited |
| CLARITY (Chung and Deisseroth, 2013; Chung et al., 2013; Kim et al., 2013) | 10 days | Yes | No | Rodent, human and non-human primate brains, spinal cord, zebrafish (Zhang et al., 2014) | Hydrogel-embedding; best tissue quality when performed correctly; IHC/F | ETC difficult, customized equipment, expensive (Chung et al., 2013) |
| Advanced CLARITY (Tomer et al., 2014; Zhang et al., 2014) | 3 weeks | Yes | No | Whole mouse brain | No ETC - passive thermal CLARITY, COLM, CLARITY objectives, rapid imaging protocol | Requires COLM set-up |
| SeeDB (Ke et al., 2013; Ke and Imai, 2014) | days (fastest) | No | No | Young rodent brains (Ke et al., 2013) | No tissue deformation, fast | Tissue browning. incomplete clearing, ~~IHC~~ |
| CUBIC (Susaki et al., 2014) | 2 weeks | Mostly-Yes | No | Rodent and non-human primate brain | CUBIC informatics, optimized Scale (Susaki et al., 2014) | Brain only; potential protein loss during clearing |
| PACT, PARS | days-weeks | Yes | No | All major rodent organs; whole-body clearing | optimized/simplified CLARITY; permits long-term tissue storage; IHC/F | Slower than 3DISCO |

IHC: Compatible with immunohistochemistry
IHC/F: Compatible with immunohistochemistry, immunofluorescent labeling; validated for (>0.5 mm) depth of antibody penetration
~~IHC~~: IHC-incompatible, IHC-unverified, or strong restrictions, such as only compatible with lipophilic tissue dyes, or poor antibody penetration (<<0.5 mm)
COLM: CLARITY-optimized light sheet microscopy; CLARITY objectives possess a several-millimeter working distance, which permits whole-brain or thick slice imaging. The COLM set-up grants rapid sample imaging and thus improves the throughput of whole-brain analysis. However, regardless of the imaging methodology followed: e.g. such as those provided in COLM, 3DISCO and CUBIC protocols, whole-brain and large sample imaging requires a specialized, expensive microscopy set-up.

TABLE 2

Exemplary Reagents for PACT, PARS and RIMS.

| Reagent | Formulation and/or Supplier |
|---|---|
| 0.1M phosphate-buffered saline (PBS) | For all wash steps and dilutions prepared in PBS, unless noted<br>Combine 8 g NaCl, 0.2 g KCl, 1.42 g $Na_2HPO_4$, 0.245 g $KH_2PO_4$ in distilled $H_2O$<br>($dH_2O$) to a total volume of 1 L; pH to 7.4, sterile filter and store at 4° C. |
| 0.1M phosphate buffer (PB) | Add 3.1 g $NaH_2PO_4$ (monohydrate) and 10.9 g $Na_2HPO_4$ (anhydrous) in $dH_2O$ to a<br>total volume of 1 L at pH 7.4; sterile filter and store at 4° C. |

*For Cardiac Perfusion-Fixation*

| | |
|---|---|
| 4% Paraformaldehyde (PFA) | Dilute 32% (wt/vol) PFA stock to 4% PFA in final concentration 0.1M PBS |
| PBS flush | Prepare 0.1M PBS with 0.5% sodium nitrate (wt/vol) and 10 units/ml heparin |

*Hydrogel Monomer Solutions*

| | |
|---|---|
| A2P0 | 2% Acrylamide, 0% PFA in 0.1M PBS<br>For 200 ml, add 10 ml of 40% (wt/vol) acrylamide to 100 ml of 0.2M PBS and 90<br>ml $dH_2O$ |
| A4P0 | 4% Acrylamide, 0% PFA in 0.1M PBS<br>For 200 ml, add 20 ml of 40% (wt/vol) acrylamide to 100 ml of 0.2M PBS and 80<br>ml $dH_2O$ |
| A4P4 | 4% Acrylamide, 4% PFA in 0.1M PBS<br>For 200 ml, add 20 ml of 40% (wt/vol) acrylamide and 25 ml of 32% (wt/vol) PFA<br>to 100 ml of 0.2M PBS and 55 ml $dH_2O$ |
| A0P4 | 4% PFA in 0.1M PBS<br>For 200 ml, add 25 ml of 32% (wt/vol) PFA to 100 ml of 0.2M PBS and 75 ml $dH_2O$ |
| 0.25% VA-044 Initiator | 2,2'-Azobis[2-(2-imidazolin-2-yl)propane]dihydrochloride (VA-044, Wako Chemicals USA, Inc.)<br>Add 100 mg to 40 ml hydrogel monomer solution in a 50 ml conical immediately prior to use (PACT)<br>Add 0.5 g to 200 ml 0.1M PBS immediately prior to use (PARS) |
| $N_2$ | PACT: attach a long needle (22 G × 4-inch hypodermic needle, Air-Tite (#N224) Virginia Beach, VA) to the gas source ($N_2$ tank with regulator and hose), lower needle to the bottom of the vacutainer or conical containing hydrogel monomer and tissue, and bubble gas through hydrogel solution for 1+ minutes; immediately proceed to hydrogel polymerization step<br>PARS: attach tubing to the $N_2$ tank regulator/hose, and insert the opposite end into the ziplock bag; loosely seal ziplock bag around tubing so that excess gas may escape; turn on $N_2$ gas flow to fill the perfusion chamber and ziplock; allow atmosphere exchange for 2 minutes; additionally, one may bubble $N_2$ through PBS in perfusion chamber box as perfusate is recirculated; immediately proceed to hydrogel polymerization step |

*PACT and PARS Detergents*

| | |
|---|---|
| 0.1% tritonX-100 (vol/vol) in PBS | Add 1 ml tritonX-100 to 0.1M PBS for a total volume of 1 L, pH to 7.5 |
| 4% Sodium dodecyl sulfate (SDS) | Add 40 g SDS to 0.1M PBS for a total volume of 1 L, pH to 7.5 |
| 8% SDS | Add 80 g SDS to 0.1M PBS for a total volume of 1 L, pH to 7.5 |
| 20% SDS | Add 200 g SDS to 0.1M PBS for a total volume of 1 L, pH to 7.5 |
| 10% Deoxycholate | Add 100 g sodium deoxycholate to 0.1M PBS for a total volume of 1 L, pH to 7.5 |

*PARS Chamber*

| | |
|---|---|
| C&B Metabond | Parkell Inc. (#S380) Edgewood, NY |
| Reusable feeding needles | Fine Science Tools, Foster City, CA |
| Cannula, tubing | PlasticsOne, Roanoke, VA |
| PARS Chamber | Pipette tip boxes (assorted sizes for mice, rats), PTFE tubing, peristaltic pump, ziplock bags |

*Histology and Imaging*

| | |
|---|---|
| Antibody incubation buffer | Dilute all antibodies (~1:200-400) and/or staining reagents in 0.1M PBS containing<br>2% normal donkey serum, 0.1% TritonX-100 and 0.01% (wt/vol) sodium azide |
| RIMS | 40 g Histodenz™ (Sigma-Aldrich # D2158) in 30 mL of 0.02M phosphate buffer with 0.01% sodium azide, pH to 7.5 with NaOH; net cost of $3/ml |
| sRIMS | 70% sorbitol (w/v) (Sigma-Aldrich #S1876) in 0.02M phosphate buffer with 0.01% sodium azide, pH to 7.5 with NaOH; net cost of $0.2/ml |
| 80-90% glycerol | Prepare 80-90% (vol/vol) glycerol (Sigma-Aldrich #G5516) in $dH_2O$ |
| FocusClear™ | CelExplorer Labs, Taiwan<br>$36/ml |

TABLE 2-continued

Exemplary Reagents for PACT, PARS and RIMS.

| Reagent | Formulation and/or Supplier |
|---|---|
| Antibodies and Small-molecule Dyes for Histology | |
| DAPI (4',6-Diamidino-2-Phenylindole, Dihydrochloride) | Life technologies (#D-1306), Grand Island, NY<br>0.1-10 µg/ml |
| anti-pan-cytokeratin (AE1/AE3) Alexa Fluor 488 primary antibodies | eBiosciences (#53-9003) San Diego, CA<br>1:100 dilution |
| Atto 488-conjugated anti-GFAP nanobody | GFAP nanobody producing according to published methods (Li et al., 2012; Perruchini et al., 2009)<br>Purified GFAP nobodies were conjugated to Atto 488 (Sigma-Aldrich), diluted in dH$_2$O to 1 mg/ml stock<br>1:100 dilution |
| chicken anti-tyrosine hydroxylase (TH) IgY | Ayes Labs (#TYH) Tigard, OR<br>1:400 dilution |
| chicken anti-glial fibrillary acidic protein (GFAP) IgY | Ayes Labs (#GFAP) Tigard, OR<br>1:400 dilution |
| rabbit anti-ionized calcium-binding adapter molecule 1 (Iba1) IgG | Biocare medical (#CP 290A) Concord, CA<br>1:200 dilution |
| rabbit anti-integrin β4 and anti-integrin β5 IgGs | Santa Cruz Biotechnology (β4: sc-9090, (β5: sc-14010) Dallas, Texas<br>1:200 dilution |
| rabbit anti-β tubulin IgG | Santa Cruz Biotechnology (#sc-9104) Dallas, Texas<br>1:200 dilution |
| Alexa Fluor 647 conjugated donkey anti-mouse IgG | Jackson ImmunoResearch (#715-606-150) West Grove, PA<br>1:200 dilution |
| NeuroTrace 530/615 Red Fluorescent Nissl Stain | Life Technologies (#N-21482), Grand Island, NY<br>1:50 dilution |
| SYSTO 24 | Life technologies (#S-7559), Grand Island, NY<br>1:200 dilution |
| Acridine Orange | Life technologies (#A-1301), Grand Island, NY<br>100 µg/ml dilution |
| Lectin | Vector laboratories (#L-1174), Burlingame, CA<br>1:100 dilution |
| Methylene blue | Sigma-Aldrich (#66720) St. Louis, MO<br>1 µg/ml |
| DRAQ5 | Cell signaling (#4084) Danvers, MA<br>1:200 dilution |
| Atto-565 conjugated Phalloidin | Sigma-Aldrich (#94072) St. Louis, MO<br>1:100 dilution |
| 7.0 mm or 3.0 mm spacers or | iSpacer, SunJin Lab Co. |
| 0.5 mm or 2.5 mm spacers | Silicone Isolator, Electron Microscopy Sciences, PA |
| smFISH | |
| Ethanol | Graded dilutions of ethanol: 100%, 95%, 70% ethanol prepared with RNase-free sterile H$_2$O |
| permeabilization buffer | 0.5% sodium borohydride (wt/vol) in 70% ethanol solution |
| hybridization buffer | 10% dextran sulfate (wt/vol, Sigma D8906), 10% formamide (vol/vol), 2X SSC |
| 20mer oligo probes towards β-actin | 1nM per each of 24 Alexa 594 labeled 20mer oligo probes towards β-actin prepared in hybridization buffer |
| 2X SSC, Saline sodium citrate buffer | For 20X SSC stock, dissolve 175.3 g NaCl and 88.2 g Sodium Citrate in 800 ml dH$_2$O, pH to 7.0 and bring to a total volume of 1 L. Autoclave to sterilize<br>For 2X SSC, combine 100 mL 20X SSC with 850 ml dH$_2$O, pH to 7.0, then add dH$_2$O to a total volume of 1 L |
| 30% Formamide 2X SSC | For 500 ml, combine 150 ml Formamide with 50 ml 20X SSC and 300 ml dH$_2$O, pH to 7.0 |
| Slowfade Gold+ DAPI | Life technologies (#S-36938), Grand Island, NY<br>Mounting media for smFISH samples |
| aminosilane-treated coverslips | Coverslips were sequentially transferred between and sonicated in three solutions: first 1M NaOH, then 100% EtOH, and finally acetone. The cleaned coverslips were immediately submerged into a 2% solution of (3-Aminopropyl) triethoxysilane (Sigma 440140) in acetone for two minutes. Amine-modified coverslips were rinsed and stored in ultra pure water at room temperature. (Lubeck et al., 2014) |

TABLE 3

Biomedical Applications of PARS and PACT

| Application | Cleared Tissue | Additional Information |
|---|---|---|
| Peripheral immunoactivation: effects on cognition and health | Whole-body, with IHC for cytokines, inflammation, and neuronal markers | (Hsiao et al., 2012; Hsiao and Patterson, 2011; Lucas et al., 2006) |
| Myelination trajectory over lifetime; Demyelinating disorders (autism, traumatic brain injury, multiple sclerosis): physiological symptoms and neuropathology | Whole-body clearing (see note[1]) | (Gibson et al., 2014; Hsiao et al., 2012; Hsiao and Patterson, 2011; Kaya et al., 2012; Zoukos et al., 1992) |
| Neurogenesis: mapping populations of neural stem cells, nerve/axon regeneration | Whole-body clearing | (Bartzokis et al., 2012; Erturk et al., 2012; Gibson et al., 2014; Jung et al., 2014) |
| Tracing complex long-range fiber bundles, such as for the vagus nerve | Whole-body clearing, focus on periphery and spinal cord | (Berthoud and Neuhuber, 2000; Birmingham et al., 2014; George et al., 2000) |
| Brain-gut connection, microbiome | Whole-body clearing | (Hsiao et al., 2013) |
| Stroke | PARS for Vasculature fixation, immunolabeling, whole body clearing to visualize vasculature within specific organs/tissues | |
| Mapping tumor architecture | PACT of tumor biopsies, PARS for rodent cancer models | (Colomba and Ridley, 2014; Fukamachi et al., 2010; Magnon et al., 2013; Vakoc et al., 2009) |
| Biofilms characterizing biofilm structure, and the regulations and the interaction of different layers | PACT of tissue/biofilm samples | (Ernst et al., 1999; Singh et al., 2000) |
| Diffusion Tensor Imaging (DTI) | (see note[2]) | (Alexander et al., 2007; Bartzokis et al., 2012; Huppi et al., 1998; Schain et al., 2014) |

[1] In both the central and peripheral nervous system, myelin is primarily composed of lipids (75-80% by dry weight) (Morell and Quarles, 1999). Myelin basic protein (MBP) is by far the most abundant protein of the myelin sheath, accounting for roughly 60-80% of the total protein content, depending on species. Unlike MBP, other myelin proteins are generally insoluble in aqueous solution and thus are not easily extracted. But, these along with MBP may be extracted using SDS using standard protocols for membrane protein isolation. Thus, a major concern of clearing protocols is inadequate PFA and/or hydrogel monomer crosslinking to stabilize myelin proteins in tissue samples. Whereas immunolabeling for myelin-associated proteins (MAPs) may still be feasible to delineate, for example, axons or nerve fibres in cleared tissue, as was shown in CLARIFIED human tissue(Chung et al., 2013), it remains uncertain whether quantitative studies on demyelination and remyelination may be accurately assessed in PACT/PARS-processed tissue where some myelin components are potentially washed away during clearing. Indeed, some authors have reported specifically avoiding clearing tissue in their studies on myelination due to this fear of solubilizing and removing the lipid-rich myelin sheath(Jung et al., 2014). Of the various published clearing protocols, SeeDB, CLARITY and PACT/PARS have the greatest potential to leave certain myelin structural elements intact. Namely, SeeDB(Ke et al., 2013) has demonstrated compatibility with lipophilic dyes, while CLARITY/PACT/PARS all include a hydrogel-tissue embedding step that is expected to prevent the loss of myelin proteins during clearing with SDS. Finally, in a study that investigated the use of optical clearance microscopy to reconstruct myeloarchitecture, brain samples were optically cleared and mounted with ScaleA2 before OCM (Leahy et al., 2013). However, because the authors did not provide detail on their clearing methods, one cannot assess whether the tissue was extensively cleared in ScaleA2, or whether ScaleA2 was primarily used as a refractive index mounting media, wherein the risk of myelin loss would be minimal.

[2] Recently, a method for label-free in vivo imaging of myelinated axons with spectral confocal reflectance microscopy (SCoRe) was reported as a more easily implemented alternative to diffusion tensor imaging (DTI) (Schain et al., 2014). Profiting from the high refractive index of lipid-rich myelin, the SCoRe method permits the fine-scale imaging of changes in axonal myelination with only a conventional laser scanning confocal microscope. It is clear that a new approach to ex vivo imaging could be implemented that replaces the diffusion of materials in living organisms with whole-organism PARS-based transfer of materials in PARS-processed and immunolabeled samples.

Animals

Wild-type mice (C57BL/6N and FVB/N, both males and females), Thy1-YFP mice (line H), and Th-cre (1 Tmd/J) mice were used in the development and testing of novel clearing protocols and clearing reagents. Thy1-YFP mice were used to evaluate the maintenance of endogenous fluorescent signals throughout multi-week clearing steps and under long-term sample storage in RIMS. Periadolescent through adult wild-type rats (Long-Evans and Wistar, males and females) were used to optimize clearing protocols for larger tissue samples, and to depict the preservation of vasculature during lengthy perfusion-based clearing and antibody staining steps. For transcardial perfusion, subjects were deeply anesthetized with an overdose of Euthasol (100 mg/kg IP injection) prior to intracardiac perfusion first with heparinized PBS (10 U/mL heparin in 0.1 M PBS) containing 0.5% $NaNO_2$ and then with 4% PFA. For PACT, the brain and/or desired organs were excised and post-fixed in 4% PFA for several hours prior to hydrogel monomer infusion and clearing steps. For PARS-based whole-body clearing, the intracardiac catheter was inserted into the left ventricle extending just beyond the aortic valve, stabilized inside the aorta with a loose loop of suture thread. For PARS-based whole-brain clearing, the descending aorta was ligated with a microclamp. For experiments involving the visualization of AAV9-CAG-eGFP transduced cells, young adult female C57Bl/6 mice were injected with virus via the retro-orbital sinus, and following a 6-month delay for viral transduction and eGFP expression, mice were euthanized for PACT and PARS studies.

AAV Production and Systemic Delivery

By injecting mice with adeno-associated viral vectors carrying fluorescently-labeled transgenes, it was possible to observe the compatibility of PARS processing and RIMS mounting with more sparse, localized fluorescent labeling than that which is driven by the Thy1 promoter (FIGS. 5A-C versus FIGS. 5D-E). Sparse labeling of specific neuron types and glia as well as localized eGFP expression in distinct organs (e.g. liver and hippocampus FIGS. 5D-E) was clearly visible. Single stranded ssAAV-CAG-eGFP vectors packaged into AAV9 or the AAV9 variant capsid, AAV9BD1, was generated and purified as described (Lock et al., 2010). The AAV9BD1 capsid was modified from AAV9 (U. Penn) with the following mutations (VP1 numbering): 1) An N498Y mutation was made to reduce liver transduction (Pulicherla et al., 2011), 2) the amino acid sequence AAAD-SPAHPS (Chen et al., 2009) was inserted between AA588-589, and 3) a Y731F mutation was made (Pulicherla et al., 2011). $1 \times 10^{12}$ vector genomes (vg) of either virus was delivered intravenously into young adult female C57Bl/6 mice via the retro-orbital sinus and the mice were euthanized 6 months later for assessment of native eGFP fluorescence by PARS. All imaging of PARS brain and liver tissue from AAV9-injected mice was performed after 2 weeks tissue storage in RIMS.

Selection of PACT and PARS Reagents

To screen different hydrogel monomer formulations and clearing conditions, several adult C57 and Thy-1 eYFP mice (Jackson) were anesthetized with an overdose of Euthasol (100 mg/kg, IP injection) and transcardially perfused first with PBS containing 0.5% NaNO2 and 10U/mL heparin, and then 4% paraformaldehyde (PFA) in PBS. The excised whole brains were sliced into 1 mm and 3 mm sagittal sections and coronal sections, postfixed in 4% PFA at room temperature for 2-6 hours (post-fixing whole-brain and sections at 4° C. overnight is also a valid option), and then sections were incubated at 4° C. overnight in A2P0 (2% acrylamide and 0% paraformaldehyde in PBS), A4P0 (4% acrylamide and 0% paraformaldehyde in PBS), or, A4P4 (4% acrylamide and 4% paraformaldehyde in PBS) hydrogel monomer solution, each containing 0.25% photoinitiator 2,2'-Azobis[2-(2-imidazolin-2-yl)propane]dihydrochloride (VA-044, Wako Chemicals USA, Inc.). While still submerged in hydrogel monomer, the hydrogel-infused samples were degassed by bubbling nitrogen through the sample-hydrogel solution in the vacutainer or 5 mL Eppendorf tubes for 1 minute. It should be noted that several, more rigorous methods of replacing oxygen atmosphere with an inert gas were experimented with, as was deemed necessary in the original and advanced CLARITY protocols (Chung et al., 2013; Tomer et al., 2014) (e.g., 1. Placing the vacutainer containing the sample on ice; 2. Degassing the vacutainer with the house vacuum line while gently vortexing for several minutes; 3. Removing the sample from ice and bubbling nitrogen through the hydrogel monomer solution for several minutes; 4. Repeating steps 1-3 several times). However, it was determined that the brief 1-minute exchange of oxygen for nitrogen supported adequate polymerization: residual oxygen may have hampered the complete hybridization between tissue and acrylamide monomers, however the tissue-hydrogel matrix was sufficient for preserving tissue architecture and protein content. To polymerize the hydrogel-tissue matrix, the samples were transferred to a 37° C. waterbath or heating block and incubated for 2-3 hours at this elevated temperature. The polymerized samples were washed briefly with PBS to remove excess hydrogel, transferred to 50 mL conical tubes, and incubated for 2-5 days at 37° C. with shaking in either PBS, 0.1% tritonX-100 in PBS, or a clearing solution: 4% SDS, 8% SDS, 20% SDS, or 10% Deoxycholate, all prepared in 0.1M PBS, pH 7.5. Images of 3 mm brain sections were taken at 24 hours and 48 hours (FIG. 1A) to show the trade-off between greater tissue swelling for tissue hydrogel matrixes prepared with low PFA concentrations, and slower tissue clearing for tissue-hydrogel matrixes prepared with high PFA (and acrylamide) concentrations; the A4P0 hydrogel formulation was selected for general use in subsequent PACT and PARS experiments. 72-hr incubation of brain sections in the 8% SDS clearing solution resulted in superior tissue clearing (FIG. 7A), and so the 8% clearing solution was selected for subsequent PACT and PARS experiments. Regarding clearing time, this parameter must be optimized in a case-specific manner. 24-hour clearing may be sufficient for small tissue samples or highly porous tissue, while larger, highly myelinated, or dense tissue sections and whole organs may require >96 hours. Care must be taken to not overclear the samples and also to check periodically for excessive swelling if samples are to be stored long term since swelling does contribute to hydrogel softening and disintegration in the long run, risking sample loss. This is accelerated by elevated temperature and mechanical stress during sample preparation and handling. Gentle treatment of the tissue-hydrogel samples and the addition of antimicrobial agents to incubation solutions allows the hydrogel to remain stable for up to two weeks. Also, it was determined that an additional round of tissue crosslinking with 1-2% PFA or of tissue-hydrogel re-polymerization after clearing was beneficial to counteracting both tissue expansion in mounting media and tissue disintegration.

PACT Immunohistochemistry

To immunostain PACT-processed tissue, cleared samples were washed with 4-5 changes of PBS over 1 day to remove residual SDS. Then, the samples were incubated with primary antibodies (1:200-400) in PBS containing 2% normal donkey serum, 0.1% TritonX-100 and 0.01% sodium azide at room temperature with shaking for 3-7 days. Six A4P0-polymerized and six A4P4-polymerized 3-mm sagittal sections were removed from these antibody incubations at 24 hrs, 48 hrs and 72 hrs in order to measure IgG penetration depth in cleared tissue (see FIG. 1B). For remaining sections, unbound primary antibody was removed via washing sections in 4-5 PBS buffer exchanges over the course of one day. Then, samples were incubated with secondary antibodies (Fab fragment secondary antibodies are preferred, 1:200-400) in PBS containing 2% normal donkey serum, 0.1% TritonX-100 and 0.01% sodium azide at room temperature with shaking for 2-5 days. After washing with 4-5 changes of PBS over 1 day, the samples were incubated in RIMS solution (40 g of Sigma D2158 (Histodenz™) in 30 mL of 0.02M phosphate buffer with 0.01% sodium azide, pH to 7.5 with NaOH—which results in a final concentration of 88% Histodenz w/v) at room temperature until they become transparent. During long incubations (>4 days) of tissue in antibody, small-molecule stains, or RIMS, the solution was exchanged for fresh halfway through the incubation. As an extra precaution and to prevent bacterial growth, tissues may be transferred to fresh 50 ml conical tubes or staining jars with every buffer exchange. It is suggested that RIMS incubations and mounting be performed in a clean environment—either in a hood, or by decanting RIMS into a fresh conical over flame to minimize bacterial contamination.

The primary antibodies used for passive staining were chicken anti-tyrosine hydroxylase (TH) IgY, chicken anti-glial fibrillary acidic protein (GFAP) IgY (Ayes Labs, Tigard, Oreg.), rabbit anti-ionized calcium-binding adapter molecule 1 (Iba1) IgG (Biocare medical, Concord, Calif.), rabbit anti-integrin b4, b5 IgG, and rabbit antibeta tubulin IgG (Santa Cruz Biotechnology, Dallas, Tex.). An AlexaFluor 647 conjugated donkey anti-mouse IgG (Jackson ImmunoResearch, West Grove, Pa.) was used for the antibody penetration experiment (FIG. 1B). Nissl staining was performed with NeuroTrace 530/615 Red Fluorescent Nissl Stain (1:50 in PBS, Life Technologies, Grand Island, N.Y.; samples were incubated at RT overnight and then washed in PBS prior to mounting. For small molecule staining with acridine orange, samples were placed in a 100 μg/mL solution of acridine orange for 10 minutes, followed by washout in PBS for one hour. The tissues were then placed in RIMS solution for 4 hours prior to imaging. All steps were performed at room temperature.

PARS Chamber Design

To perfuse PARS reagents through vasculature for clearing and immunolabeling steps necessitated the fabrication of a simple apparatus to recirculate reagents with a continuous pressure gradient on tissue for several days-to-weeks during the lipid extraction and antibody diffusion. So, using the traditional cardiac perfusion fixation technique (Gage et al., 2012; Jonkers et al., 1984) as a delivery method, a PARS chamber was devised that consisted of the following components: 1) a feeding needle catheter clamped in-place within the left ventricle of the subject, 2) a perfusate collection well (pipette box) to catch recirculating reagents that exit the vasculature through a lesioned right atrium, and 3) catheter tube (PTFE tubing) that transfers recirculating reagents from the collection well back into subject vasculature via its passage through a peristaltic pump (FIG. 10A). To confirm that this set-up was functional for whole-organism clearing, several different detergents including SDS at several different percentages, sodium lauryl sarcosine, and sodium deoxycholate, at various concentrations, were continuously perfused through whole mice and rats via the carotid artery for up to 2 weeks. As in PACT (FIG. 7A), only SDS could effectively render tissue transparent for optical imaging. Likewise, when delivered using the PARS chamber set-up, 8% SDS could efficiently solvate lipids deep in tissue and accomplish uniform clearing of large tissue samples. Thus, the PARS chamber set-up was adopted for subsequent PARS experiments.

PARS Clearing and Staining

For transcardial perfusion fixation of adult mice or rats, a feeding needle was inserted through the left ventricle and into the aorta, and loosely sutured in place to the vessel at the level of the aortic arch. Following perfusion with PBS and 4% PFA, as summarized for PACT, the fixed whole rodents were transferred into a custom-built perfusion chamber where the solutions inside the chamber is perfused into the rodent and recirculated via a peristaltic pump. The rodent was post-fixed with 4% PFA through the same feeding needle into the aorta at a flow rate of 1 mL/min for 1-2 h at room temperature. For clearing of rat brain and spinal cord, the arterial circulation was systematically ligated, leaving the carotid arteries intact and removed tissue not directly perfused by these vessels. To prevent PFA from crosslinking the acrylamide monomers, PBS was perfused for 2 hours at RT to wash out the residual PFA, and 4% acrylamide (A4P0) was infused in PBS at RT overnight. The next day, PBS was again perfused to remove any remaining PFA/acrylamide polymers/monomers in the vasculature. Before polymerization and without disconnecting perfusion lines, the perfusion chamber was placed into a ziplock bag and infused nitrogen gas into the perfusion chamber through a separate connection to degas the sample. The polymerization process was initiated by adding 200 mL of 0.25% VA-044 initiator with PBS and submerging the degassed perfusion chamber in a 37-42° C. water bath for 2-3 hours. A lead weight was placed on top of the perfusion chamber to prevent it from tipping over. After polymerization, the solution was replaced with 8% SDS in 0.1M PBS, pH 7.5 clearing buffer, and the mouse/rat was perfused for up to 2 weeks. For PARS IHC, the cleared mouse/rat was first perfused with 8 buffer changes of 200 mL PBS over a 2-day period to remove the residual SDS. Then, using the same antibody formulations described in the PACT protocol, a 3-day perfusion with a primary antibody cocktail, 1-day perfusion with PBS wash, a 3-day perfusion with the secondary antibody cocktail, and a 1-day PBS wash was conducted in order to stain the peripheral organs of the cleared mouse/rat.

PARS-CSF Methodology for Brain and Spinal Cord Clearing

For applications restricted to brain and spinal cord mapping a within-skull PARS strategy was developed that grants thorough clearing of the whole-brain and whole-spinal cord by direct infusion of hydrogel monomers and clearing reagents into the CSF via an intracranial brain shunt. Under specific circumstances (e.g., the preexisting availability of a guide cannula in the subject from an in vivo pharmacological, neurobiological, or optogenetic study), PARS-CSF would permit whole-brain clearing and histology that is automatically optimized for the region near the existing cannula, and that requires less time and reagents as the equivalent whole organ PACT procedure. Herein, two routes for intracranial delivery of PARS reagents were validated. To clear the spinal cord, a cannula may be inserted either into the cisterna magna or lowered through the skull (by drilling a hole in the region of interest and using tweezers to create an opening in the dura), to the level of the subarachnoid space, directly above the dorsal inferior colliculus, (see FIG. 3A). The rat spinal cord sample (right) could be cleared when PARS-CSF was conducted at elevated temperatures and for a longer period of clearing. To clear the whole brain, the cannula may be lowered through the skull, penetrating the dura, and placed in the region directly above the olfactory bulb (see FIG. 3B). The cannula (21G, PlasticsOne) is cemented in-place on the skull surface using dental acrylic (C&B-Metabond, Parkell Inc.). The PARS procedure was then applied to this intracranial preparation: the catheter tubing was connected to the subdural cannula as opposed to the cardiac feeding tube, and all PACT reagents were infused at 1 ml/min using the same order and timeframe as in PARS. For whole-brain clearing, the subject was transcardial-perfusion fixed and decapitated, with only the head transferred to the PARS chamber and connected to the infusion lines. The pipette box and catheter lines were prefilled with 4% acrylamide monomer solution (A4P0), the tubing was connected to the cannula, and A4P0 was intracranially infused at a 1 ml/min flow rate overnight at room temperature (FIG. 10A, left). After flushing the brain of unbound PFA and acrylamide monomers (2-hour infusion of PBS), which was very important to ensure that the vasculature remained unpolymerized, the whole-brain was degassed via transferring the PARS chamber into a ziplock bag and placing the chamber under an inert atmosphere (N2) for two minutes (FIG. 10A, right). The bagged-PARS chamber was then transferred to a 37-42° C. water bath, and degassed PBS supplemented with the thermal initiator was infused through the brain for the entire 2-3 h incubation. After formation of this whole brain-hydrogel matrix, in-skull tissue clearing was accomplished via constant perfusion-recirculation of 8% SDS through the cannula for 4 days, with the PARS chamber remaining in the 37-42° C. water bath for the entire process. Finally, after extensive PBS washing (2-3 days), the catheter lines were disconnected, and the brain was removed, sectioned, and mounted in RIMS for imaging (FIG. 3B).

Using mice that were IV-injected with AAV9-eGFP, the PARS-CSF procedure for whole-organ clearing was validated with respect to the following conditions: 1) only limited bias in how well regions clear relative to the cannula placement, 2) no structural damage in regions near the cannula due excessive fluid pressure, either from too high flow rate or inadequate drainage of perfused liquids, causing high intracranial pressure, 3) preservation of subcellular structural morphology, and 4) good visualization of sparsely labeled cell populations and fluorescence. It may have particular relevance to scientists performing research that already involves the use of intracerebral (IC) or intracerebroventricular (ICV) cannulated mouse or rat subjects and that requires post-mortem brain histology for each subject.

Antibody Penetration

Four transcardially perfused and 4% PFA post-fixed adult mouse (4-12 weeks old) brains were cut into 2 mm sagittal slices, and these slices were PACT processed. Specifically, one half of each PFA-fixed brain was hybridized with A4P4 hydrogel, while the other half was hybridized in 4A0P hydrogel. All the samples were passively cleared with 8% SDS in PBS, as described in the PACT protocol, and the residual SDS was removed by PBS washing for 1 day. The samples were then incubated in primary antibody cocktails (donkey antimouse-IgG antibody, 1:200, in PBS containing 2% normal donkey serum, 0.1% Triton-X100 and 0.01% sodium azide) for a range of time-periods, spanning 24-72 hours. Samples were then washed with 4-5 buffer exchanges of 0.1 M PBS over 1 day and mounted in RIMS solution. Images were taken with a Zeiss LSM 780 confocal microscope using the W Plan-Apochromat 20×/1.0 DIC M27 (working distance 1.8 mm). The depth of antibody penetration (FIG. 1B) was outlined on y-z projected images using Fiji with Reslice and Z project plugins.

RIMS (Refractive Index Matching Solutions) for PACT and PARS Samples

As a final step in tissue preparation for imaging, sample mounting comprises immersing the tissue section in a medium that will help to align the refractive indices of the objective, lens immersion media, and tissue, which confers higher resolution and imaging depth. In order to circumvent the use of FocusClear™, a prohibitively expensive reagent, in mounting PACT and PARS, a new mounting solution alternative was formulated. Based on the principles of tissue optical clearing, two major groups of chemicals (sugar alcohols and radiocontrast agents) were rationally screened that have the following desirable characteristics of an optical clearing agent (high water solubility, low viscosity, high density, low osmolarity, low autofluorescence, non-fluorophore quenching, biocompatible, low cost. Sorbitol, a sugar alcohol that is affordable and widely available was identified. At 70-80% (w/v) solution, sorbitol can effectively clear 200 μm thick uncleared and up to 1 mm thick PACT cleared brain sections with little quenching of fluorescence. The formulation (termed sRIMS, see below for description) was later modified to include 0.02-0.05 M phosphate buffer (pH maintenance), 0.1% tween-20 (enhances tissue penetration), and sodium azide (preservative to inhibit bacterial growth). In addition to sugar alcohols, radiocontrast agents were also evaluated, especially intravascularly delivered non-ionic iodinated contrast agents (also licensed for use as density gradient media) as their physical and chemical properties closely match that of an ideal refractive index matching media. Based on cost and availability, iodixanol (Optiprep) and its monomer iohexol (Nycodenz, also available as Histodenz™, a derivative of iohexol) were tested and iohexol was found to be superior than sorbitol in index matching much larger PARS cleared samples.

Next, a side-by-side comparison (see FIG. 9A) was conducted between commonly used/commercially available mounting options: 80-90% glycerol and FocusClear™, and the media mounting media formulations described herein: sRIMS and RIMS, a mounting media optimized for our imaging set-up with standard confocal microscopy. RIMS solution was prepared via dissolving 40 g of Histodenz™ (Sigma D2158) in 0.02M phosphate buffer with 0.01% sodium azide for a total volume of 30 mL, pH to 7.5 with NaOH, which results in a final concentration of 88% Histodenz (w/v) with RI=1.46 (used throughout this work unless otherwise noted).

It is worth noting that the refractive index (RI) of RIMS may be adjusted to match the specific tissue/imaging system: it is expected that the RIMS RI may range from 1.38 (30% Histodenz w/v) to 1.48 (95% Histodenz w/v) in order to obtain very good sample resolution. Light transmittance in RIMS (FIG. 9B) was measured with a Reichert AR200 Refractometer. For RIMS mounting, samples were first submerged in RIMS at room temperature until they become transparent. During this period, the cleared tissue initially shrinks for the first few hours (see FIGS. 3B, 9D). Continued incubation in RIMS will lead to gradual tissue expansion over time until RIMS has fully penetrated the tissue (see FIGS. 4C, 11A); it was observed that the largest samples (e.g. rat whole-brain) became transparent within one week of RIMS-immersion, after which their expansion ceased. Tissue expansion was successfully limited, however, by post-fixing the cleared and stained samples in 4% PFA for 1-2 hours at room temperature (small samples) or up to overnight (large samples) before proceeding to RIMS incubation (see FIG. 4C, right box; FIG. 11A, lower right box). Although post-fixing PARS tissue curtailed gradual tissue volume expansion (FIG. 9), the additional crosslinking also precipitated a slight decrease in tissue transparency (FIG. 11A). Fluorescence intensity, cell phenotyping, or resolvable depth of imaging were not adversely affected, however.

sRIMS: A Cost-Effective Sorbitol-Based Alternative to RIMS

70% sorbitol (w/v) (Sigma 51876) in 0.02M phosphate buffer with 0.01% sodium azide, pH to 7.5 with NaOH; net cost of $0.2/ml. While RIMS outperformed sRIMS in certain experiments conducted, in terms of resolvable imaging depth, sorbitol is a commonly available chemical across scientific laboratories, and thus offers a convenient, cost-effective and excellent alternative to glycerol-based mounting solutions.

Vasculature Preservation

Rats were transcardially perfused with heparinized PBS, 4% PFA, and lastly additional PBS wash. Then, before any hydrogel monomer infusion or clearing as in PARS, the rat was perfused via its intra-aortic catheter with 100 mL Atto 488 conjugated anti-GFAP nanobody (1:100 in PBS) at room temperature overnight. The GFAP nanobody was prepared according to published methods (Li et al., 2012). It was conjugated to Atto 488 fluorescent dye prior to use. The brain was removed from the skull and incubated in 4% PFA at 4° C. overnight to crosslink the nanobody. The brain was then cut into 1 mm coronal slices and processed according to standard PACT protocols, including hydrogel monomer infusion, hybridization, and passive sample clearing in 8% SDS in 0.1M PBS, pH7.5 at 37° C. for 3 days. Cleared samples were incubated in RIMS solution for one day and mounted in RIMS solution for imaging. Images were taken using Zeiss LSM 780 confocal microscope with LD LCI Plan-Apochromat 25×/0.8 Imm Corr DIC M27 multi-immersion objective. The above methods were repeated in mice for the labeling of vasculature with Alexa Fluor 647-conjugated antimouse IgG. Briefly, 4% PFA-fixed mice were transcardially perfused with Alexa Fluor 647-conjugated anti mouse IgG overnight using the same intra-aortic catheter that was installed for 4% PFA fixation. The brain was excised, post-fixed in 4% PFA at 4° C. overnight, sectioned into 1 mm coronal slices and PACT cleared in 8% SDS in 0.1M PBS, pH7.5 at 37° C. for 3 days. Cleared samples were incubated in RIMS solution for one day and mounted in RIMS solution for imaging.

Sliced Tissue Expansion and Weight Gain Measurement

PFA-fixed adult mouse (4-12 weeks old) brain was cut into six 1 mm thick coronal slices. Slices from one half of the brain were stored in PBS, while slices from the other half of the brain were PACT-cleared for 4 days. Slices were weighed and imaged with a conventional camera before and after clearing. The size of the slices was outlined and calculated using Image J. The tissue expansion and weight gain were determined by calculating the change in size and weight of slices before and after clearing (FIG. 1E), and normalizing them to the pre-PACT measurements.

Protein Loss Measurement

The percentage of protein loss for each sample (FIGS. 1C, 2E) was obtained by measuring the amount of total protein in the clearing solutions collected from PACT or PARS clearing with NanoDrop blanked with respective solutions, and normalized to the weight of the mouse (for PARS) or the slices (for PACT) before clearing.

Whole-Brain Tissue Morphology Preservation and Quantification

To observe the effect of PARS processing and RIMS mounting on brain volume, PFA-fixed adult mouse brains were either immediately extracted (uncleared control) or PARS-processed; and then brains from these two groups were treated according to one of the following conditions: incubated in PBS for 1 day, incubated in PBS for 1 week, mounted in RIMS for 1 day, mounted in RIMS for 2 weeks, or post-fixed and mounted in RIMS for 2 weeks. Cleared and uncleared brains from all conditions were then photographed to estimate their relative size change (FIG. 4C), cut into sections to visualize clearing depth (FIG. 11A), slide-mounted, and imaged via confocal microscopy in order to evaluate gross changes in tissue architecture (e.g. morphological deformations of major brain regions, structure integrity of ventricles and vasculature) (FIG. 11B). The percentage of protein loss for each sample (FIG. 1C, 2E) was obtained by measuring via NanoDrop the protein concentration of clearing solution aliquots that were collected after PACT or PARS-processing of tissue. The net protein loss could then be estimated based on this concentration and the known total volume of clearing solution used during processing. The amount of protein lost by each sample was normalized to the weight of the mouse (for PARS) or the tissue slice (for PACT) before clearing so that protein losses across samples and across tissue processing conditions could be compared.

Single-Molecule RNA FISH

Tissue samples were adhered to aminosilane-treated coverslips by dehydrating for 1 hour under light vacuum. Samples were permeabilized prior to hybridization according to the following protocol: First, samples were washed twice in 100% ethanol for 10 minutes at room temperature. Next, samples were washed in 95% ethanol for 10 minutes at room temperature. Samples were then incubated in 70% ethanol for 2 hours at 4° C. After incubation, tissue was placed in a 0.5% sodium borohydride (w/v) 70% ethanol solution for 10 minutes at room temperature. Finally, the tissue was rehydrated with 3 washes of PBS. Hybridizations were performed overnight at 37° C. in a hybridization buffer composed of 10% dextran sulfate (w/v, Sigma D8906), 10% formamide (v/v), 2×SSC containing 1 nM per each of 24 Alexa 594 labeled 20 mer oligo probes towards B-actin. The next day samples were washed in 30% formamide 2×SSC at room temperature for 30 minutes followed by 4 washes with 2×SSC. After washing sample was mounted between two coverslips with Slowfade Gold+DAPI (Life S36938). Samples were imaged on a Nikon Ti Eclipse microscope with an Andor Ikon-M camera and a 60×/1.4 NA Plan Apo λ objective with an additional 1.5× magnification. Images were acquired as Z-stacks with a 0.5 μm step size over 30 μm. Samples were excited by a 589 nm (SDL-589-XXXT), 532 nm (SDL-532-200TG) and 405 nm (SDL-405-LM-030) lasers manufactured by Shanghai Dream Laser.

The smFISH images (FIG. 2) were analyzed using image analysis scripts written in MATLAB. To determine the average background of the sample, the images were median filtered using a 50×50 pixel kernel and the average pixel intensity of the center 200×200 pixel sub-image was used as the average background value of the image. The smFISH dots were found by applying a Laplacian of Gaussian filter, thresholding the image based on the average background value and comparing the resulting image with a dilated image to find local maxima. The error bars were calculated using the standard deviation of the resulting measurements.

Human Tissue Biopsy Preparation

Human basal cell carcinoma skin tissue samples were obtained from patients undergoing excision of their cancers after appropriate informed consent and under approval of UCLA IRB #12-01195. Tissue samples were obtained from sections of tumors not necessary for diagnostic or margin control purposes and varied in size depending on the size of the original skin cancer. Biopsied tumor samples were processed utilizing the PACT methodology as described for rodent tissue, using 4% acrylamide solution (A4P0) to generate hydrogel support matrix for fixed tissue. Polymerized tissue-hydrogel matrices were then passively cleared for 2-7 days (i.e., depending on tissue thickness) in 8% SDS at 37° C. In general, a 3 mm thick human skin section could be rendered transparent within 3-4 days.

PACT-processed samples were immunolabeled with anti-pan-cytokeratin (AE1/AE3) Alexa Fluor 488 primary antibodies (eBiosciences) at 1:100 dilution for two days followed by a 1-day wash in PBS. All labeling and wash steps were performed at room temperature, and final PACT-processed biopsy samples were mounted in RIMS. Imaging was performed on a Zeiss 780 confocal microscope with a 20× long working distance objective as described above.

Despite testing a range of clearing times (2-7 days in 8% SDS) for tissue-hydrogel samples, the subcutaneous layer (consisting primarily of adipocytes) resisted consistent clearing (yellow tissue, FIG. 8A) due to incomplete micelle solvation of all the packed lipids in adipocytes.

Scanning Electron Microscopy

Samples were imaged on an FEI Quanta 200F environmental scanning electron microscope (ESEM) in ESEM mode. Thin slices of PACT-processed brain tissues were placed on the sample holder in the chamber and imaged at a voltage of 5 kV and working distance between 7.7-8.3 mm with a spot size of 3 or 4 using the gaseous secondary electron detector (GSED). Please note that stretching during cutting/SEM process will make the pores of tissue-hydrogel hybrid larger. The actual effective pore size of the SEM images should be smaller than what is presented here.

Quantification Methods

Mean nearest neighbor distance (NND): 1 mm thick coronal slices were stained with DAPI and imaged w/ the 10× 0.45N.A. plan-apo objective. 24 3 µm-thick images were taken from different regions of the cortex thalamus and striatum. A 30-pixel rolling ball radius subtraction filter was used to remove the background. All images are individually thresholded and converted into a binary image. A binary watershed segmentation was applied to divide cells that are clustered together. The resulting images were quantified with the analyzing particles option on Image J. The centroid of each cell was identified in the measurement the NND were calculated by applying the "nnd" plugin on imageJ.

GFP size quantification: 1 mm thick coronal slices of AAV9-eGFP IV injected mouse brain were imaged with the 5×0.25N.A. Fluar objective. A maximum projection of the Z-stack was used for quantification. The area of each GFP positive neuron was isolated and quantified with the analyzing particles option on ImageJ.

Both nearest neighbor distance measurements and GFP size calculations were performed for three brain regions: cortex, striatum, and thalamus; in uncleared, PARS cleared, and PARS cleared then post-fixed mouse brain slices (see FIG. 11A for representative brain slices and FIG. 11B for data results). The mean cell size and mean NND for all counted cells were computed for each region, and data were analyzed for statistically significant differences in cell size or in NND between regions.

Fluorescence Microscopy

Cleared tissue samples were incubated in RIMS solution for one day. The samples were then mounted in the respective solutions using 7.0 mm or 3.0 mm spacers (iSpacer, SunJin Lab Co.), or 0.5 mm or 2.5 mm spacers (Silicone Isolator, Electron Microscopy Sciences, PA) with coverglasses. Coverslipped samples were stored at room temperature and shielded from light prior to imaging. Of note, most fluorescent images and initial sample visualization were performed on a conventional microscope (Zeiss LSM 780) with either the Fluar 5×/0.25 M27 dry objective (working distance 12.5 mm), Plan-Apochromat 10×/0.45 M27 air objective (working distance 2.0 mm), LD SC Plan-Apochromat 20×/1.0 Corr M32 85 mm scale-immersion objective (working distance 5.6 mm), or LD LCI Plan-Apochromat 25×/0.8 Imm Corr DIC M27 multi-immersion objective (working distance 0.57 mm). The only exceptions were for smFISH experiments, which used a Nikon Ti Eclipse microscope with an Andor Ikon-M camera and a 60×/1.4 NA Plan Apo 1 objective, and for the acquisition of images presented in FIG. 3C, wherein the samples were imaged by Leica Microsystems using a Leica TCS SP8 two-photon microscope with the Leica HC FLUOTAR L 25×/1.00 IMM CORR objective (working distance 6.0 mm). Image reconstructions were performed using Imaris imaging software (Bitplane). After imaging, samples were embedded in RIMS at room temperature for storage.

Summary of the Objectives Used for all Confocal Imaging by-Figure:

FIG. 1: (F left) Fluar 5×/0.25 M27 dry objective; (F right; G; H; K) LD LCI Plan-Apochromat 25×/0.8 Imm Corr DIC M27 multi-immersion objective; (I, J) LD SC Plan-Apochromat 20×/1.0 Corr M32 85 mm scale-immersion objective. (L) Zeiss Plan-Apochromat 10×/0.45 air objective.

FIG. 2: (A-B) Samples imaged on a Nikon Ti Eclipse microscope with an Andor Ikon-M camera and a 60×/1.4 NA Plan Apo 1 objective with an additional 1.5× magnification. Images acquired as Z-stacks with a 0.5 µm step size over 30 µm. Samples were excited by a 640 nm Coherent Cube, and 532 nm (SDL-532-200TG) and 405 nm (SDL-405-LM-030) lasers.

FIG. 3: (C) Leica HC FLUOTAR L 25×/1.00 IMM CORR objective. FIG. 5: (A) Fluar 5×/0.25 M27 dry objective; (B) Leica HC FLUOTAR L 25×/1.00 IMM CORR objective working distance of 6.0 mm; (C) Top: Fluar 5×/0.25 M27 dry objective and Bottom (inset): LD LCI Plan-Apochromat 25×/0.8 Imm Corr DIC M27 multi-immersion objective; (D) Leica HC FLUOTAR L 25×/1.00 IMM CORR objective; (E) LD LCI Plan-Apochromat 25×/0.8 Imm Corr DIC M27 multi-immersion objective. FIT. 6: (A) Zeiss LSM 780 confocal microscope with the 10×0.45 N.A. Plan-Apochromat; (B) LD SC Plan-Apochromat 20×/1.0 Corr M32 85 mm scale-immersion objective (working distance 5.6 mm, Zeiss).

FIG. 8: (B-C) Zeiss 780 confocal microscope with the Zeiss 5×0.25 N.A Fluar objective and the LD LCI Plan-Apochromat 25×/0.8 N.A. multi-immersion objective. (D) smFISH Samples imaged on a Nikon Ti Eclipse microscope with an Andor Ikon-M camera and a 60×/1.4 NA Plan Apo 1 objective with an additional 1.5× magnification.

Figure 9:
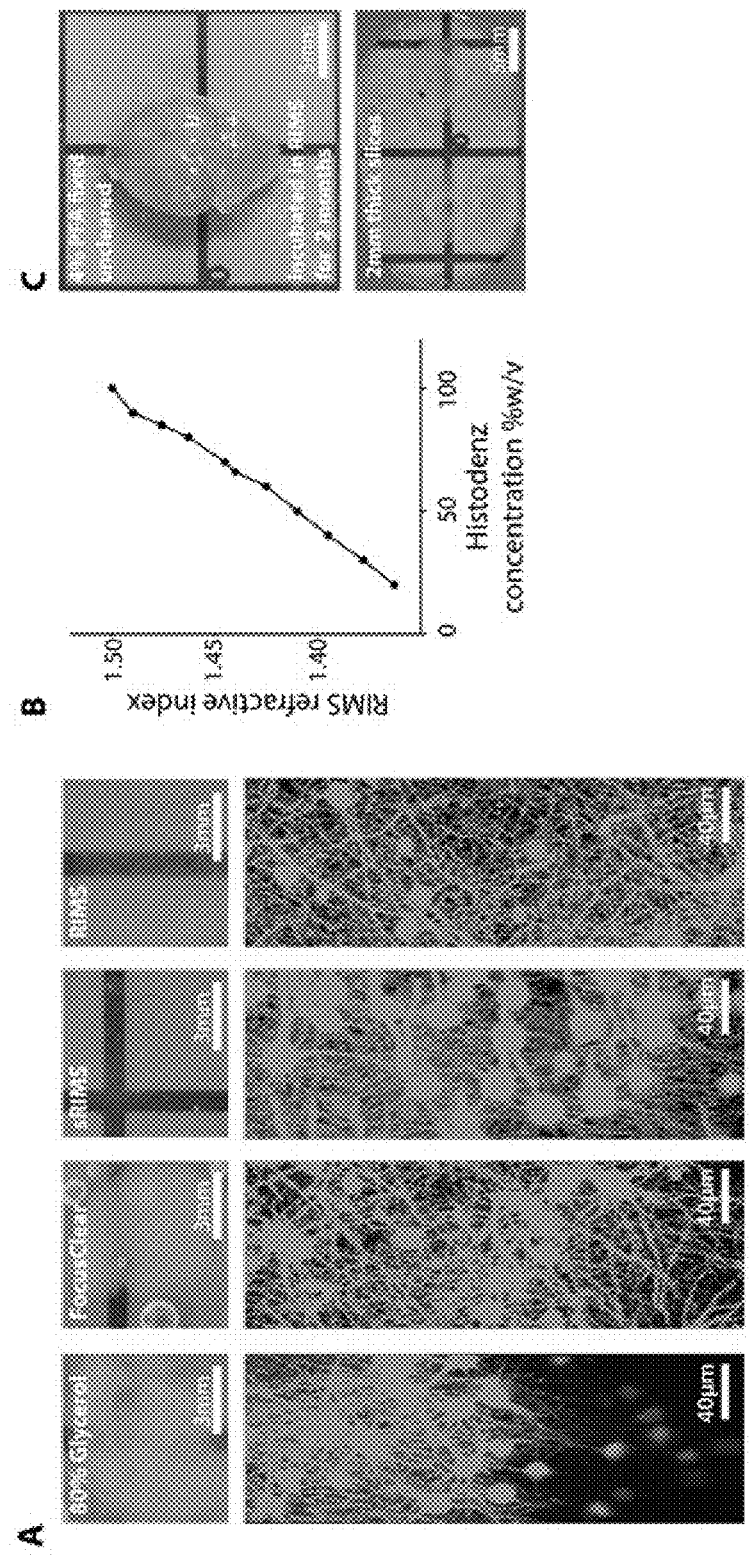
FIG. 9 demonstrates, in accordance with an embodiment of the invention (related to FIGS. 1 and 4; and Table 2), sRIMS and RIMS give better optical transparency by matching the refractive index of cleared tissue-hydrogel hybrid and allow for long-term storage and imaging. (A) Optical transparency (top, bright field camera) and confocal images (bottom) of PACT cleared 1 mm Thy1-eYFP mouse brain coronal slices mounted and stored for 2 weeks in different media. Whereas the optical transparency of samples mounted in 80% glycerol was very poor, RIMS and sRIMS, a sorbitol solution-based mounting media (see Methods), enhanced the optical transparency and imaging resolution depth of mounted samples. The inventors detected precipitation, perhaps of dissolved salts, in tissue that had been mounted in glycerol and FocusClear™ for more than 1 day. (B) The refractive index of RIMS prepared with various concentrations of Histodenz™ (diluted in phosphate buffer). (C) After a 2-month incubation in RIMS, uncleared whole-brain tissues become optically transparent in superficial, poorly myelinated regions. Thus, RIMS immersion offers a milder, albeit slower, alternative to more involved clearing protocols when superior resolution is desired for thick-sectioned (~50-300 μm) tissue slices. (D) Representative images (bright field camera) and the quantification of the percentage of tissue shrinkage of PACT cleared (3 days) 3 mm Thy1-eYFP mouse brain sagittal blocks after incubated in RIMS for 1 day (n=4 blocks) for A4P0 and A4P4 hydrogel-tissue hybrids. (E) A size comparison between uncleared Thy1-eYFP whole-brain and a PARS cleared Thy1-eYFP whole-brain mounted in RIMS for 3 months (bright field camera), and the eYFP fluorescence signal (z=1 mm) after long-term storage in RI 1.43 (60% Histodenz w/v) RIMS. For microscopy see Methods.
Figure 9:
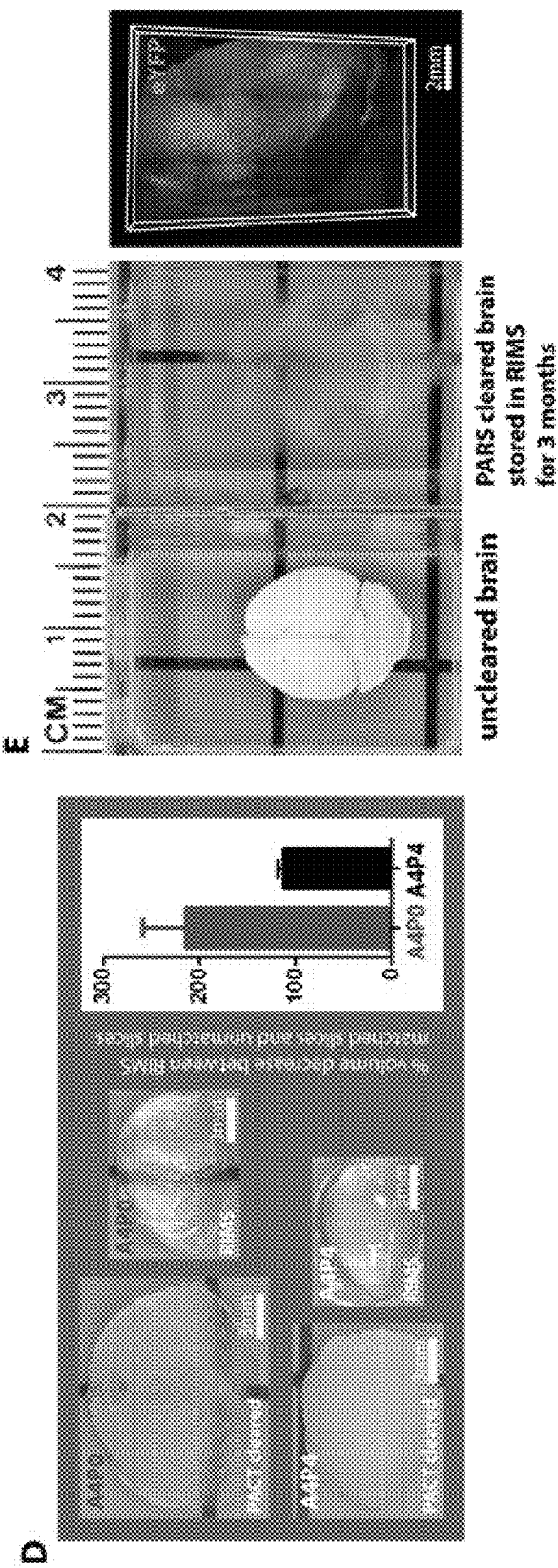

FIG. 9: (A) LD LCI Plan-Apochromat 25×/0.8 Imm Corr DIC M27 multi-immersion objective. (E) Fluar 5×/0.25 M27 dry objective.

Figure 10:
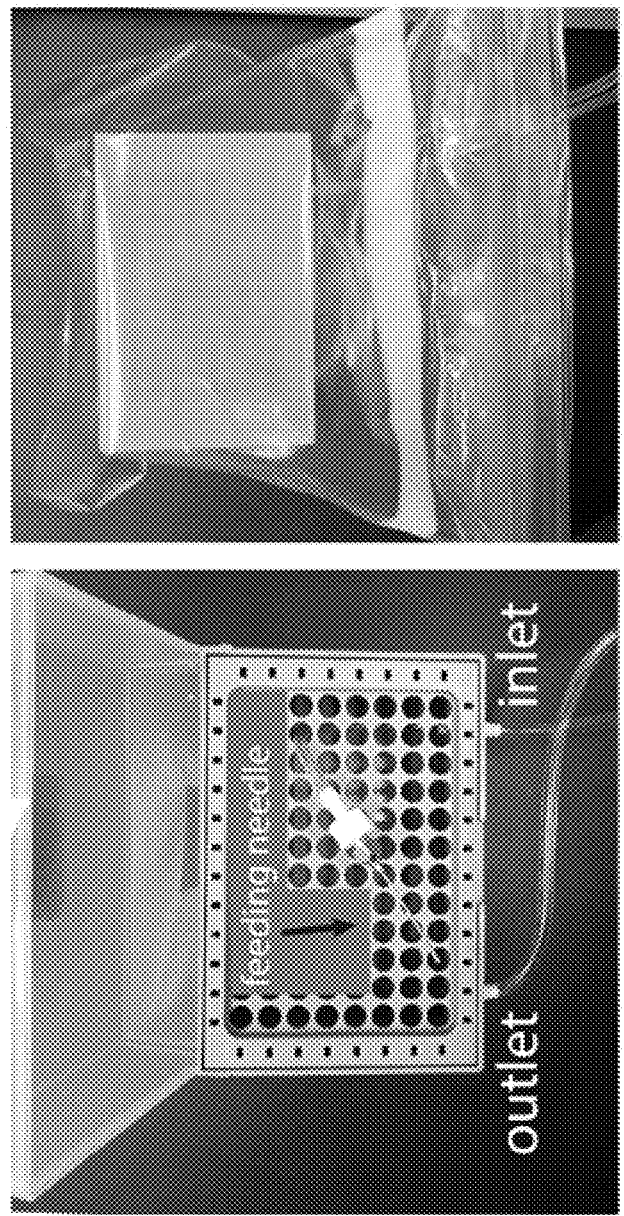
FIG. 10 demonstrates, in accordance with an embodiment of the invention (related to FIGS. 3 and 4), development of PARS System for whole-body clearing. (A) Left: PARS was conducted in custom-built perfusion chambers prepared from pipette boxes. Following perfusion-fixation with 4% PFA through a feeding needle that is affixed to the left ventricle or ascending aorta, the rodent is secured atop the pipette tip grating. To drain the pipette box as it fills with perfusate that exits the rodent body through a lesion in the right atrium, one end of a catheter tube is secured to the bottom of the pipette tip box. The tubing is then threaded through a peristaltic pump, and the opposite end is connected to the feeding needle. This allows perfusate to be siphoned out of the pipette box and recirculated back through the cardiac catheter, achieving continuous perfusion of hydrogel monomers, wash buffer, clearing detergents, and histological stains through the rodent vasculature. Of note, this PARS set-up may be applied to PARS-CSF (see FIG. 3A) by attaching catheter tubing to the intracranial cannula rather than feeding needle. Right: Immediately prior to hydrogel polymerization, the entire perfusion chamber (with catheter-connected subject) is sealed within a ziplock bag for tissue degassing, and the entire set-up is left within this bag throughout the rest of the PARS protocol. The bag allows the perfusion chamber to be placed in a shallow water bath-forming a barrier to prevent water from flooding the perfusion chamber, or from PARS reagents from contaminating the water bath. (B) Rodents were perfused with Atto 488-conjugated GFAP nanobody (left) and Alexa Fluor 647 conjugated anti-mouse IgG antibody (right) to investigate whole-body vasculature accessibility via the perfusion of PARS reagents. Specifically, PARS reagents must be able to circulate through both major blood vessels as well as tissue microvasculature in order to achieve uniform, rapid clearing and labeling of both central and peripheral organs, poorly- and well-vascularized tissues alike. Left: extensive populations of glial cells surrounding a major vessel in the cortex. Middle: high magnification volume rendering showing astrocytic end feet participating in the formation of the blood brain barrier. Right: well-preserved vasculature of a 1 mm mouse brain section (cortex) achieved via perfusion-based delivery of whole immunoglobulins into uncleared tissue. The extensive labeling of mouse vasculature suggests that the PARS pressure gradient can drive antibody solutions through major blood vessels. For microscopy see Methods.
Figure 10:
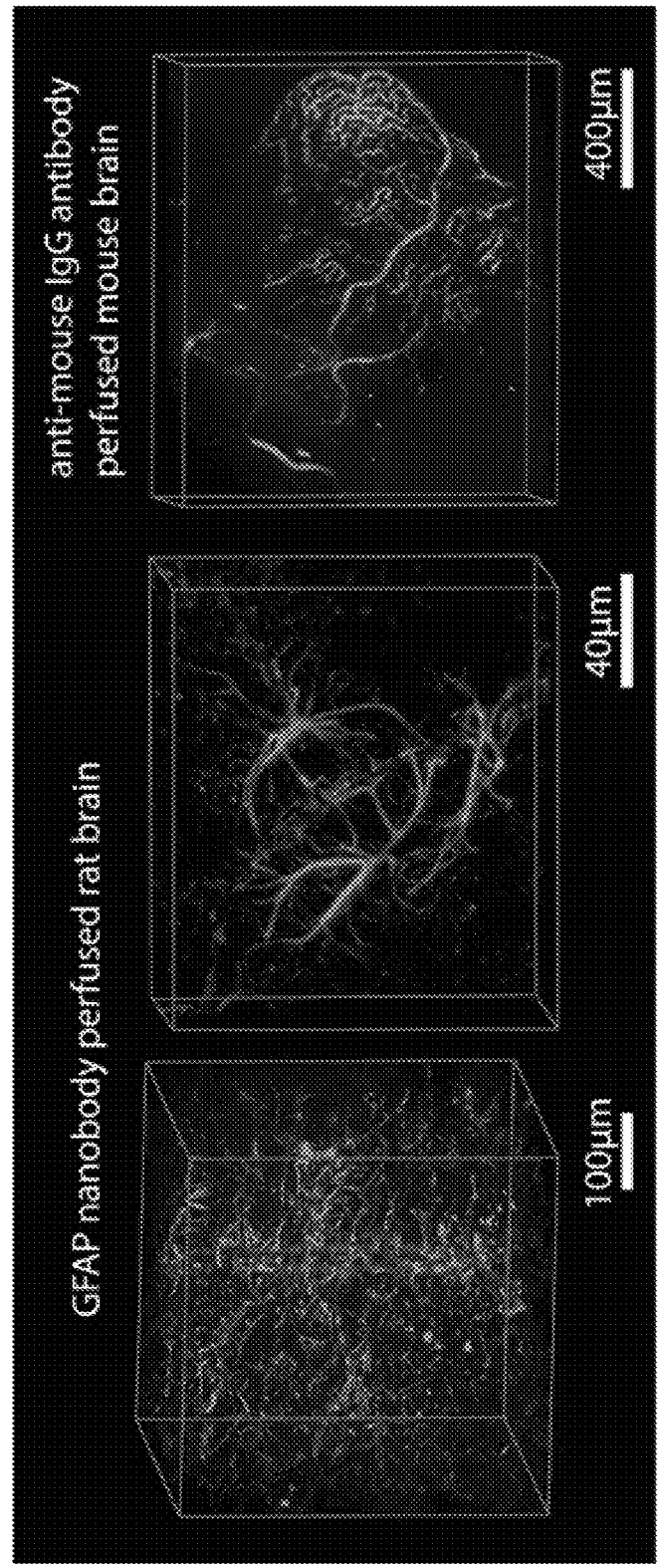

FIG. 10: (B) Left: LD LCI Plan-Apochromat 25×/0.8 Imm Corr DIC M27 multi-immersion objective; Right: Zeiss LSM 780 confocal microscope with the 10×0.45 N.A. Plan-Apochromat.

FIG. 12: Zeiss LSM 780 confocal microscope with the 10×0.45 N.A. Plan-Apochromat.

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

REFERENCES

Becker, K., Ja hrling, N., Saghafi, S., Weiler, R., and Dodt, H. U. (2012). Chemical clearing and dehydration of GFP expressing mouse brains. PLoS ONE 7, e33916.

Becker, K., Jahrling, N., Saghafi, S., and Dodt, H. U. (2013). Ultramicroscopy: light-sheet-based microscopy for imaging centimeter-sized objects with micrometer resolution. Cold Spring Harbor protocols 2013, 704-713.

Buxbaum, A. R., Wu, B., and Singer, R. H. (2014). Single b-actin mRNA detection in neurons reveals a mechanism for regulating its translatability. Science 343, 419-422.

Chung, K., and Deisseroth, K. (2013). CLARITY for mapping the nervous system. Nat. Methods 10, 508-513.

Chung, K., Wallace, J., Kim, S. Y., Kalyanasundaram, S., Andalman, A. S., Davidson, T. J., Mirzabekov, J. J., Zalocusky, K. A., Mattis, J., Denisin, A. K., et al. (2013). Structural and molecular interrogation of intact biological systems. Nature 497, 332-337.

Deisseroth, K. A., and Gradinaru, V. (2014). Functional Targeted Brain Endoskeletonization. U.S. patent US2014030192.

Dodt, H.-U., Leischner, U., Schierloh, A., Ja hrling, N., Mauch, C. P., Deininger, K., Deussing, J. M., Eder, M., Zieglga nsberger, W., and Becker, K. (2007). Ultramicroscopy: three-dimensional visualization of neuronal networks in the whole mouse brain. Nat. Methods 4, 331-336.

Ertu rk, A., and Bradke, F. (2013). High-resolution imaging of entire organs by 3-dimensional imaging of solvent cleared organs (3DISCO). Exp. Neurol. 242, 57-64.

Ertu rk, A., Becker, K., Ja hrling, N., Mauch, C. P., Hojer, C. D., Egen, J. G., Hellal, F., Bradke, F., Sheng, M., and Dodt, H.-U. (2012a). Three-dimensional imaging of solvent-cleared organs using 3DISCO. Nat. Protoc. 7, 1983-1995.

Famm, K., Litt, B., Tracey, K. J., Boyden, E. S., and Slaoui, M. (2013). Drug discovery: a jump-start for electroceuticals. Nature 496, 159-161.

Femino, A. M., Fay, F. S., Fogarty, K., and Singer, R. H. (1998). Visualization of single RNA transcripts in situ. Science 280, 585-590.

Gage, G. J., Kipke, D. R., and Shain, W. (2012). Whole animal perfusion fixation for rodents. J. Vis. Exp. 65, 3564.

George, M. S., Sackeim, H. A., Rush, A. J., Marangell, L. B., Nahas, Z., Husain, M. M., Lisanby, S., Burt, T., Goldman, J., and Ballenger, J. C. (2000). Vagus nerve stimulation: a new tool for brain research and therapy. Biol. Psychiatry 47, 287-295.

Hama, H., Kurokawa, H., Kawano, H., Ando, R., Shimogori, T., Noda, H., Fukami, K., Sakaue-Sawano, A., and Miyawaki, A. (2011). Scale: a chemical approach for fluorescence imaging and reconstruction of transparent mouse brain. Nat. Neurosci. 14, 1481-1488.

Harmsen, M. M., and De Haard, H. J. (2007). Properties, production, and applications of camelid single-domain antibody fragments. Appl. Microbiol. Biotechnol. 77, 13-22.

Hoffman, A. S. (2002). Hydrogels for biomedical applications. Adv. Drug Deliv. Rev. 54, 3-12.

Jonkers, B. W., Sterk, J. C., and Wouterlood, F. G. (1984). Transcardial perfusion fixation of the CNS by means of a compressed-air-driven device. J. Neurosci. Methods 12, 141-149.

Ke, M.-T., Fujimoto, S., and Imai, T. (2013). SeeDB: a simple and morphology preserving optical clearing agent for neuronal circuit reconstruction. Nat. Neurosci. 16, 1154-1161.

Kim, S. Y., Chung, K., and Deisseroth, K. (2013). Light microscopy mapping of connections in the intact brain. Trends Cogn. Sci. 17, 596-599.

Kuwajima, T., Sitko, A. A., Bhansali, P., Jurgens, C., Guido, W., and Mason, C. (2013). ClearT: a detergent- and solvent-free clearing method for neuronal and non-neuronal tissue. Development 140, 1364-1368.

Leong, S. K., and Ling, E. A. (1990). Labelling neurons with fluorescent dyes administered via intravenous, subcutaneous or intraperitoneal route. J. Neurosci. Methods 32, 15-23.

Li, T., Bourgeois, J. P., Celli, S., Glacial, F., Le Sourd, A. M., Mecheri, S., Weksler, B., Romero, I., Couraud, P. O., Rougeon, F., and Lafaye, P. (2012). Cellpenetrating anti-GFAP VHH and corresponding fluorescent fusion protein VHH-GFP spontaneously cross the blood-brain barrier and specifically recognize astrocytes: application to brain imaging. FASEB J. 26, 3969-3979.

Lock, M., Alvira, M., Vandenberghe, L. H., Samanta, A., Toelen, J., Debyser, Z., and Wilson, J. M. (2010). Rapid, simple, and versatile manufacturing of recombinant adeno-associated viral vectors at scale. Hum. Gene Ther. 21, 1259-1271.

Lyubimova, A., Itzkovitz, S., Junker, J. P., Fan, Z. P., Wu, X., and van Oudenaarden, A. (2013). Single-molecule mRNA detection and counting in mammalian tissue. Nat. Protoc. 8, 1743-1758.

Moy, A. J., Wiersma, M. P., and Choi, B. (2013). Optical histology: a method to visualize microvasculature in thick tissue sections of mouse brain. PLoS ONE 8, e53753.

Pulicherla, N., Shen, S., Yadav, S., Debbink, K., Govindasamy, L., Agbandje-McKenna, M., and Asokan, A. (2011). Engineering liver-detargeted AAV9 vectors for cardiac and musculoskeletal gene transfer. Mol. Ther. 19, 1070-1078.

Raj, A., van den Bogaard, P., Rifkin, S. A., van Oudenaarden, A., and Tyagi, S. (2008). Imaging individual mRNA molecules using multiple singly labeled probes. Nat. Methods 5, 877-879.

Spalteholz, W. (1914). U ber das Durchsichtigmachen von menschlichen und tierischen Pra paraten (Leipzig: S. Hierzel).

Steinke, H., and Wolff, W. (2001). A modified Spalteholz technique with preservation of the histology. Ann. Anat. 183, 91-95.

Susaki, E. A., Tainaka, K., Perrin, D., Kishino, F., Tawara, T., Watanabe, T. M., Yokoyama, C., Onoe, H., Eguchi, M., Yamaguchi, S., et al. (2014). Whole-brain imaging with single-cell resolution using chemical cocktails and computational analysis. Cell 157, 726-739.

Tomer, R., Ye, L., Hsueh, B., and Deisseroth, K. (2014). Advanced CLARITY for rapid and high-resolution imaging of intact tissues. Nat. Protoc. 9, 1682-1697.

Tseng, S. J., Lee, Y. H., Chen, Z. H., Lin, H. H., Lin, C. Y., and Tang, S. C. (2009). Integration of optical clearing and optical sectioning microscopy for three dimensional imaging of natural biomaterial scaffolds in thin sections. J. Biomed. Opt. 14, 044004.

Zhang, M. D., Tortoriello, G., Hsueh, B., Tomer, R., Ye, L., Mitsios, N., Borgius, L., Grant, G., Kiehn, O., Watanabe, M., et al. (2014). Neuronal calcium-binding proteins 1/2 localize to dorsal root ganglia and excitatory spinal neurons and are regulated by nerve injury. Proc. Natl. Acad. Sci. USA 111, E1149-E1158.

SUPPLEMENTAL REFERENCES

Becker, K., Jährling, N., Saghafi, S., Weiler, R., and Dodt, H.-U. (2012). Chemical clearing and dehydration of GFP expressing mouse brains. PloS one 7, e33916.

Chen, Y. H., Chang, M., and Davidson, B. L. (2009). Molecular signatures of disease brain endothelia provide new sites for CNS-directed enzyme therapy. Nature medicine 15, 1215-1218.

Chung, K., and Deisseroth, K. (2013). CLARITY for mapping the nervous system. Nature methods 10, 508-513.

Chung, K., Wallace, J., Kim, S. Y., Kalyanasundaram, S., Andalman, A. S., Davidson, T. J., Mirzabekov, J. J., Zalocusky, K. A., Mattis, J., Denisin, A. K., et al. (2013). Structural and molecular interrogation of intact biological systems. Nature 497, 332-337.

Dodt, H.-U., Leischner, U., Schierloh, A., Jahrling, N., Mauch, C. P., Deininger, K., Deussing, J. M., Eder, M., Zieglgansberger, W., and Becker, K. (2007). Ultramicroscopy: three-dimensional visualization of neuronal networks in the whole mouse brain. Nature methods 4, 331-336.

Ertürk, A., Becker, K., Jahrling, N., Mauch, C. P., Hojer, C. D., Egen, J. G., Hellal, F., Bradke, F., Sheng, M., and Dodt, H.-U. (2012). Three-dimensional imaging of solvent-cleared organs using 3DISCO. Nature protocols 7, 1983-1995.

Ertürk, A., and Bradke, F. (2013). High-resolution imaging of entire organs by 3-dimensional imaging of solvent cleared organs (3DISCO). Experimental neurology 242, 57-64.

Erturk, A., Mauch, C. P., Hellal, F., Forstner, F., Keck, T., Becker, K., Jahrling, N., Steffens, H., Richter, M., Hubener, M., et al. (2012). Three-dimensional imaging of the unsectioned adult spinal cord to assess axon regeneration and glial responses after injury. Nature medicine 18, 166-171.

Gage, G. J., Kipke, D. R., and Shain, W. (2012). Whole animal perfusion fixation for rodents. Journal of visualized experiments: JoVE.

Hama, H., Kurokawa, H., Kawano, H., Ando, R., Shimogori, T., Noda, H., Fukami, K., Sakaue-Sawano, A., and Miyawaki, A. (2011). Scale: a chemical approach for fluorescence imaging and reconstruction of transparent mouse brain. Nature neuroscience 14, 1481-1488.

Jonkers, B., Sterk, J., and Wouterlood, F. (1984). Transcardial perfusion fixation of the CNS by means of a compressed-air-driven device. Journal of neuroscience methods 12, 141-149.

Jung, Y., Ng, J. H., Keating, C. P., Senthil-Kumar, P., Zhao, J., Randolph, M. A., Winograd, J. M., and Evans, C. L. (2014). Comprehensive Evaluation of Peripheral Nerve Regeneration in the Acute Healing Phase Using Tissue Clearing and Optical Microscopy in a Rodent Model. PLoS ONE 9, e94054.

Ke, M.-T., Fujimoto, S., and Imai, T. (2013). SeeDB: a simple and morphology-preserving optical clearing agent for neuronal circuit reconstruction. Nature neuroscience 16, 1154-1161.

Ke, M. T., and Imai, T. (2014). Optical clearing of fixed brain samples using SeeDB. Current protocols in neuroscience/editorial board, Jacqueline N Crawley [et al] 66, Unit 2.22.

Kim, S. Y., Chung, K., and Deisseroth, K. (2013). Light microscopy mapping of connections in the intact brain. Trends in Cognitive Sciences 17, 596-599.

Kuwajima, T., Sitko, A. A., Bhansali, P., Jurgens, C., Guido, W., and Mason, C. (2013). ClearT: a detergent- and solvent-free clearing method for neuronal and non-neuronal tissue. Development 140, 1364-1368.

Li, T., Bourgeois, J. P., Celli, S., Glacial, F., Le Sourd, A. M., Mecheri, S., Weksler, B., Romero, I., Couraud, P. O., Rougeon, F., et al. (2012). Cell-penetrating anti-GFAP VHH and corresponding fluorescent fusion protein VHH-GFP spontaneously cross the blood-brain barrier and specifically recognize astrocytes: application to brain imaging. FASEB journal: official publication of the Federation of American Societies for Experimental Biology 26, 3969-3979.

Lock, M., Alvira, M., Vandenberghe, L. H., Samanta, A., Toelen, J., Debyser, Z., and Wilson, J. M. (2010). Rapid, simple, and versatile manufacturing of recombinant adeno-associated viral vectors at scale. Hum Gene Ther 21, 1259-1271.

Lubeck, E., Coskun, A. F., Zhiyentayev, T., Ahmad, M., and Cai, L. (2014). Single-cell in situ RNA profiling by sequential hybridization. Nat Meth 11, 360-361.

Perruchini, C., Pecorari, F., Bourgeois, J. P., Duyckaerts, C., Rougeon, F., and Lafaye, P. (2009).

Llama VHH antibody fragments against GFAP: better diffusion in fixed tissues than classical monoclonal antibodies. Acta neuropathologica 118, 685-695.

Pulicherla, N., Shen, S., Yadav, S., Debbink, K., Govindasamy, L., Agbandje-McKenna, M., and Asokan, A. (2011). Engineering liver-detargeted AAV9 vectors for cardiac and musculoskeletal gene transfer. Molecular therapy: the journal of the American Society of Gene Therapy 19, 1070-1078.

Susaki, E. A., Tainaka, K., Perrin, D., Kishino, F., Tawara, T., Watanabe, T. M., Yokoyama, C., Onoe, H., Eguchi, M., and Yamaguchi, S. (2014). Whole-Brain Imaging with Single-Cell Resolution Using Chemical Cocktails and Computational Analysis. Cell.

Tomer, R., Ye, L., Hsueh, B., and Deisseroth, K. (2014). Advanced CLARITY for rapid and high-resolution imaging of intact tissues. Nature protocols 9, 1682-1697.

Zhang, M. D., Tortoriello, G., Hsueh, B., Tomer, R., Ye, L., Mitsios, N., Borgius, L., Grant, G., Kiehn, O., Watanabe, M., et al. (2014). Neuronal calcium-binding proteins 1/2 localize to dorsal root ganglia and excitatory spinal neurons and are regulated by nerve injury. Proceedings of the National Academy of Sciences of the United States of America 111, E1149-1158.

What is claimed is:

1. A method for modifying the structural and/or optical characteristics of tissue in situ, comprising:
   introducing a fixing solution comprising paraformaldehyde (PFA) into one or more of the vascular system, cerebrospinal fluid and ventricular system and lymphatic system of a subject, thereby forming fixed tissue within the subject;
   introducing a hydrogel monomer solution comprising acrylamide into the one or more of the vascular system, cerebrospinal fluid and ventricular system and lymphatic system of the subject, thereby forming hydrogel-treated tissue within the subject;
   initiating polymerization of hydrogel monomers;
   introducing a detergent solution into the one or more of the vascular system, cerebrospinal fluid and ventricular system and lymphatic system of the subject.

2. The method of claim 1 wherein the hydrogel monomer solution comprises from 1% to 20% acrylamide.

3. The method of claim 2, further comprising introducing a solution comprising PBS into the one or more of the vascular system, cerebrospinal fluid and ventricular system and lymphatic system of the subject, thereby forming PBS-washed tissue.

4. The method of claim 3, further comprising:
   placing the subject into a substantially air tight chamber, and
   introducing nitrogen into the chamber, thereby forming a de-gassed subject.

5. The method of claim 4, further comprising introducing a photoinitiator solution comprising 2,2'-Azobis[2-(2-imidazolin-2-yl)propane]dihydrochloride into the one or more of the vascular system, cerebrospinal fluid and ventricular system and lymphatic system of the de-gassed subject.

6. The method of claim 1, wherein the detergent solution comprises approximately 1% to 30% SDS.

7. The method of claim 6, further comprising introducing PBS into the one or more of the vascular system, cerebrospinal fluid and ventricular system and lymphatic system of the subject, thereby forming cleared and washed tissue within the subject.

8. The method of claim 7, further comprising introducing imaging media into the one or more of the subject's vascular system, cerebrospinal fluid and ventricular system and lymphatic system, wherein the imaging media comprises: (1) 1-N,3-N-bis(2,3-dihydroxypropyl)-5-[N-(2,3-dihydroxypropyl)acetamido]-2,4,6-triiodobenzene-1,3-dicarboxamide or 5-(N-2,3-Dihydroxypropylacetamido)-2,4,6-triiodo-N,N'-bis(2,3-dihydroxypropyl)isophthalamide, (2) phosphate buffer; (3) tween-20; (4) sodium azide; and optionally (5) sodium hydroxide.

9. The method of claim 8, wherein the concentration of 1-N,3-N-bis(2,3-dihydroxypropyl)-5-[N-(2,3-dihydroxypropyl)acetamido]-2,4,6-triiodobenzene-1,3-dicarboxamide or 5-(N-2,3 Dihydroxypropylacetamido)-2,4,6-triiodo-N,N'-bis(2,3-dihydroxypropyl)isophthalamide is from 10 to 100% w/v.

10. The method of claim 9, wherein (1) one or more of the solutions is introduced into the one or more of the subject's vascular system, cerebrospinal fluid and ventricular system and lymphatic system through a first tube connected to a pump; (2) one or more of the solutions are removed from the subject's circulatory system through a second tube which is in fluid communication with a reservoir into which one or more solutions are collected; and optionally (3) the pump draws the one or more collected solutions from the reservoir and introduces the one or more solutions into the one or more of the subject's vascular system, cerebrospinal fluid and ventricular system and lymphatic system through the first tube.

11. A method for immunostaining a tissue in situ, comprising:
   introducing a solution comprising a primary antibody into the one or more of the vascular system, cerebrospinal fluid and ventricular system and lymphatic system of a subject upon which the method of claim 7 has been applied.

12. The method of claim 11, further comprising introducing a buffer solution into the one or more of the vascular system, cerebrospinal fluid and ventricular system and lymphatic system of the subject.

13. The method of claim 12, further comprising introducing a solution comprising a secondary antibody into the one or more of the vascular system, cerebrospinal fluid and ventricular system and lymphatic system of the subject, wherein the secondary antibody is labeled with a visualizable marker.

14. The method of claim 13, wherein the visualizable marker is fluorescent.

15. The method of claim 11, wherein the primary antibody is labeled with a visualizable marker.

16. The method of claim 14, wherein the visualizable marker is fluorescent.

17. A method for visualizing immunostained tissue, in situ, comprising:
utilizing a microscope to visualize a marker that has been associated with tissue prepared according to the method of claim 13.

18. A composition, comprising: (1) 1-N,3-N-bis(2,3-dihydroxypropyl)-5-[N-(2,3-dihydroxypropyl)acetamido]-2,4,6-triiodobenzene-1,3-dicarboxamide or 5-(N-2,3-Dihydroxypropylacetamido)-2,4,6-triiodo-N,N'-bis(2,3-dihydroxypropyl)isophthalamide, (2) phosphate buffer; (3) tween-20; (4) sodium azide; and optionally (5) sodium hydroxide.

19. The composition of claim 18, wherein the concentration of 1-N,3-N-bis(2,3-dihydroxypropyl)-5-[N-(2,3-dihydroxypropyl)acetamido]-2,4,6-triiodobenzene-1,3-dicarboxamide or 5-(N-2,3-Dihydroxypropylacetamido)-2,4,6-triiodo-N,N'-bis(2,3-dihydroxypropyl)isophthalamide is from 10 to 100% w/v.

20. The method of claim 18, wherein introducing a fixing solution, introducing a hydrogel monomer solution and introducing a detergent solution each comprise introduction into the vascular system.

21. The method of claim 18, wherein introducing a fixing solution, introducing a hydrogel monomer solution and introducing a detergent solution each comprise introduction into cerebrospinal fluid and ventricular system.

22. The method of claim 1, wherein introducing a fixing solution, introducing a hydrogel monomer solution and introducing a detergent solution each comprise introduction into the lymphatic system.

* * * * *